US009469646B2

(12) United States Patent
Albrecht et al.

(10) Patent No.: US 9,469,646 B2
(45) Date of Patent: Oct. 18, 2016

(54) MODULATORS OF METHYL MODIFYING ENZYMES, COMPOSITIONS AND USES THEREOF

(71) Applicant: Constellation Pharmaceuticals, Inc., Cambridge, MA (US)

(72) Inventors: Brian K. Albrecht, Cambridge, MA (US); James Edmund Audia, Cambridge, MA (US); Les A. Dakin, Natick, MA (US); Victor S. Gehling, Somerville, MA (US); Jean-Christophe Harmange, Andover, MA (US); Christopher G. Nasveschuk, Stoneham, MA (US); Rishi G. Vaswani, Lexington, MA (US)

(73) Assignee: Constellation Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 14/839,273

(22) Filed: Aug. 28, 2015

(65) Prior Publication Data

US 2015/0368229 A1 Dec. 24, 2015

Related U.S. Application Data

(63) Continuation of application No. 14/766,632, filed as application No. PCT/US2014/015706 on Feb. 11, 2014, now abandoned.

(30) Foreign Application Priority Data

Feb. 11, 2013 (WO) ................ PCT/US2013/025639

(51) Int. Cl.
| | | |
|---|---|---|
| *C07D 401/12* | (2006.01) | |
| *C07D 401/14* | (2006.01) | |
| *C07D 487/04* | (2006.01) | |
| *C07D 417/04* | (2006.01) | |
| *C07D 417/14* | (2006.01) | |
| *C07D 405/14* | (2006.01) | |
| *C07D 409/06* | (2006.01) | |
| *C07D 471/04* | (2006.01) | |

(52) U.S. Cl.
CPC ........... *C07D 487/04* (2013.01); *C07D 401/12* (2013.01); *C07D 401/14* (2013.01); *C07D 405/14* (2013.01); *C07D 409/06* (2013.01); *C07D 417/04* (2013.01); *C07D 417/14* (2013.01); *C07D 471/04* (2013.01)

(58) Field of Classification Search
CPC ................ C07D 401/12; C07D 401/14
USPC ............. 514/318; 546/193, 194, 113, 278.1; 544/331
See application file for complete search history.

(56) References Cited

U.S. PATENT DOCUMENTS

| | | | |
|---|---|---|---|
| 4,738,971 A | 4/1988 | Eriksoo et al. | |
| 5,308,854 A | 5/1994 | Hoffman, Jr. et al. | |
| 7,838,520 B2 | 11/2010 | Delorme et al. | |
| 8,410,088 B2 | 4/2013 | Kuntz et al. | |
| 8,536,179 B2* | 9/2013 | Miller .................. | A61K 31/405 514/252.13 |
| 8,846,935 B2* | 9/2014 | Duquenne ............ | C07D 401/12 546/256 |
| 9,051,269 B2 | 6/2015 | Albrecht et al. | |
| 9,085,583 B2* | 7/2015 | Albrecht .............. | C07D 401/14 |
| 2003/0207875 A1 | 11/2003 | Gymer et al. | |
| 2003/0229081 A1 | 12/2003 | Maduskuie | |
| 2005/0266473 A1 | 12/2005 | Zhang et al. | |
| 2006/0035938 A1 | 2/2006 | Bladh et al. | |
| 2007/0155744 A1 | 7/2007 | Jones et al. | |
| 2008/0027050 A1 | 1/2008 | Terauchi et al. | |
| 2008/0227826 A1 | 9/2008 | Frechette et al. | |
| 2008/0280917 A1 | 11/2008 | Albrecht et al. | |
| 2009/0029991 A1 | 1/2009 | Stokes et al. | |
| 2009/0075833 A1 | 3/2009 | Chinnaiyan et al. | |
| 2009/0270361 A1 | 10/2009 | Ito et al. | |
| 2010/0069630 A1 | 3/2010 | Lee et al. | |
| 2010/0222420 A1 | 9/2010 | Chinnaiyan et al. | |
| 2010/0261743 A1 | 10/2010 | Londregan et al. | |
| 2010/0298270 A1 | 11/2010 | Keana et al. | |
| 2011/0105509 A1 | 5/2011 | Kaila et al. | |
| 2011/0212946 A1 | 9/2011 | Barrow et al. | |
| 2012/0071418 A1 | 3/2012 | Copeland et al. | |
| 2013/0040906 A1 | 2/2013 | Kuntz et al. | |
| 2013/0230511 A1 | 9/2013 | Heymach et al. | |
| 2014/0107122 A1 | 4/2014 | Kuntz et al. | |
| 2015/0259351 A1 | 9/2015 | Albrecht et al. | |

FOREIGN PATENT DOCUMENTS

| | | |
|---|---|---|
| WO | 03/020722 A1 | 3/2003 |
| WO | 03/079986 A2 | 10/2003 |
| WO | 2007/011626 A2 | 1/2007 |
| WO | 2007/014838 A1 | 2/2007 |
| WO | 2007/067968 A2 | 6/2007 |
| WO | 2009/006577 A2 | 1/2009 |
| WO | 2009/087285 A1 | 7/2009 |
| WO | 2009/153721 A1 | 12/2009 |

(Continued)

OTHER PUBLICATIONS

CAS Registry No. 1061629-12-6, (2015).
CAS Registry No. 1100242-53-2, (2015).
CAS Registry No. 1118826-71-3, (2015).
CAS Registry No. 1269034-31-2, (2015).
CAS Registry No. 1269036-62-4, (2015).
CAS Registry No. 1278089-62-5, (2015).
CAS Registry No. 1290560-58-5, (2015).
Copending U.S. Appl. No. 14/766,632, filed Aug. 7, 2015, entitled "Modulators of Methyl Modifying Enzymes, Compositions and Uses Thereof".

(Continued)

*Primary Examiner* — Celia Chang
(74) *Attorney, Agent, or Firm* — McCarter & English, LLP; Steven G. Davis; Michael J. DeGrazia

(57) ABSTRACT

Agents for modulating methyl modifying enzymes, compositions and uses thereof are provided herein.

4 Claims, 45 Drawing Sheets

(56) References Cited

FOREIGN PATENT DOCUMENTS

| WO | 2011/131741 A1 | 10/2011 |
|---|---|---|
| WO | 2011/140324 A1 | 11/2011 |
| WO | 2011/140325 A1 | 11/2011 |
| WO | 2012/005805 A1 | 1/2012 |
| WO | 2012/024543 A1 | 2/2012 |
| WO | 2012/051492 A2 | 4/2012 |
| WO | 2012/068589 A2 | 5/2012 |
| WO | 2012/075080 A1 | 6/2012 |
| WO | 2012/115885 A1 | 8/2012 |
| WO | 2012/118812 A2 | 9/2012 |
| WO | 2013/039988 A1 | 3/2013 |
| WO | 2013/049770 A2 | 4/2013 |
| WO | 2013/067296 A1 | 5/2013 |
| WO | 2013/067300 A1 | 5/2013 |
| WO | 2013/067302 A1 | 5/2013 |
| WO | 2013/075083 A1 | 5/2013 |
| WO | 2013/075084 A1 | 5/2013 |
| WO | 2013/078320 A1 | 5/2013 |
| WO | 2013/120104 A2 | 8/2013 |
| WO | 2013/138361 A1 | 9/2013 |
| WO | 2013/155317 A1 | 10/2013 |
| WO | 2013/155464 A1 | 10/2013 |
| WO | 2013/173441 A2 | 11/2013 |
| WO | 2014/049488 A1 | 4/2014 |
| WO | 2014/062720 A2 | 4/2014 |
| WO | 2014/062733 A2 | 4/2014 |
| WO | 2014/071109 A1 | 5/2014 |
| WO | 2014/077784 A1 | 5/2014 |
| WO | 2014/085666 A1 | 6/2014 |
| WO | 2014/092905 A1 | 6/2014 |
| WO | 2014/097041 A1 | 6/2014 |
| WO | 2014/100080 A1 | 6/2014 |
| WO | 2015-200650 | * 12/2015 |

OTHER PUBLICATIONS

Copending U.S. Appl. No. 14/661,797, filed Mar. 18, 2015, entitled "Modulators of Methyl Modifying Enzymes, Compositions and Uses Thereof".
U.S. Appl. No. 14/661,797, filed Mar. 18, 2015.
Alexei Vazquez, "Optimization of Personalized Therapies for Anticancer Treatment," BMC Systems Biology, 2013, 7:31, 11 pages, http://www.biomedcentral.com/1752-0509/7/31.
Amatangelo et al., "Three-Dimensional Culture Sensitizes Epithelial Ovarian Cancer Cells to EZH2 Methyltransferase Inhibition," Cell Cycle, 12(13), 2013, 2113-2119.
Extended European Search Report issued in European Application No. 13746186.9, dated Aug. 5, 2015. 6 pages.
Fiskus, et al., "Combined Epigenetic Therapy with the Histone Methyltransferase EZH2 Inhibitor 3-Deazaneplanocin A and the Histone Deacetylase Inhibitor Panobinostat Against Human AML Cells," Blood, Sep. 24, 2009, 114:13, pp. 2733-2743.
Fiskus, et al., "Histone Deacetylase Inhibitors Deplete Enhancer of Zeste 2 and Associated Polycomb Repressive complex 2 Proteins in Human Acute Leukemia Cells," Molecular Cancer Therapeutics, 2006;5:3096-3104.

International Search Report, International Application No. PCT/US2013/025639, International Filing Date Feb. 11, 2013, Mailed May 8, 2013, 9 pages.
Knutson et al., "Selective Inhibition of EZH2 by EPZ-6438 Leads to Potent Antitumor Activity in EZH2-Mutant Non-Hodgkin Lymphoma," Molecular Cancer Therapeutics, 13(4), 2014, 842-854.
Knutson, et al., "A Selective Inhibitor of EZH2 Blocks H3K27 Methylation and Kills Mutant Lymphoma Cells," Nature Chemical Biology, 8(11), 2012, 890-896.
Knutson, et al., "Durable Tumor Regression in Genetically Altered Malignant Rhabdoid Tumors by Inhibition of Methyltransferase EZH2," Proceedings of the National Academy of Sciences of the United States of America, 110(19), 2013, 7922-7927.
Konze, et al., "An Orally Bioavailable Chemical Probe of the Lysine Methyltransferases EZH2 and EZH1," ACS Chemical Biology, (2013), 8(6), 1324-1334, CAPLUS, DOI: 10.1021/cb400133j.
McCabe, et al., "EZH2 Inhibition as a Therapeutic Strategy for Lymphoma with EZH2-Activating Mutations," Nature, 492(7427), 2012, 108-112.
PubChem Compound Summary for CID 40170690, May 30, 2009, 2 pages.
PubChem Compound Summary for CID 50961558, Mar. 29, 2011, 2 pages.
PubChem Compound Summary for CID 6918837, Jul. 28, 2006, 2 pages.
PubChem Compound Summary for CID 73087, Aug. 1, 2005, 2 pages.
Qi, et al., "Selective Inhibition of Ezh2 by a Small Molecule Inhibitor Blocks Tumor Cells Proliferation," Proceedings of the National Academy of Sciences of the United States of America, 109(52), 2012, 21360-21365.
Spannhoff, et al., "The Emerging Therapeutic Potential of Histone Methyltransferase and Demethylase Inhibitors," Chem Med Chem, 2009, 4:1568-1582.
Van Aller, et al., "Long Residence Time Inhibition of EZH2 in Activated Polycomb Repressive Complex 2," ACS Chem. Biol., 9(3), 2014, 622-629.
Verma, et al., "Identification of Potent, Selective, Cell-Active Inhibitors of the Histone Lysine Methyltransferase EZH2," ACS Medicinal Chemistry Letters, 3(12), 2012, 1091-1096.
Woo, et al., "Biological Evaluation of Tanshindiols as EZH2 Histone Methyltransferase Inhibitors," Bioorganic & Medicinal Chemistry Letters, 24(11), 2014, 2486-2492.
Yap, et al., "Somatic mutations at EZH2 Y641 act dominantly through a mechanism of selectively altered PRC2 catalytic activity, to increase H3K27 trimethylation," Blood, vol. 117, No. 8, Feb. 24, 2011, pp. 2451-2459.
Registry, Sep. 29, 2011, RN: 1333889-30-7.
Registry, Sep. 7, 2011, RN 1329352-49-9.
Registry, Sep. 7, 2011, RN: 1329234-68-5.
Registry, Sep. 6, 2011, RN: 1328976-87-9.
Registry, Sep. 5, 2011, RN: 1328462-28-7.
Registry, Sep. 4, 2011, RN: 1328132-30-4.
Registry, Sep. 2, 2011, RN: 1327055-57-1.
Registry, Sep. 1, 2011, RN: 1326727-17-6.
Registry, May 25, 2011, RN: 1300453-83-1.

* cited by examiner

152

153

159

160

183

204

211

212

217

218

219

223

224

229

230

231

234

235

236

240

241

243

252

253

256

257

261

266

267

270

273

275

277

280

284

288

290

293

294

298

299

300

302

304

306

307

308

310

313

314

316

317

321

327

335

336

337

341

342

343

344

345

346

347

352

355

356

357

358

359

360

362

363

364

365

366

367

368

369

370

373

375

376

377

378

380

381

382

401

402

403

404

405

406

407

408

409

410

411

412

416

417

418

419

420

421

422

423

424

425

426

427

428

429

430

431

432

433

434

435

436

437

440

442

MODULATORS OF METHYL MODIFYING ENZYMES, COMPOSITIONS AND USES THEREOF

CROSS-REFERENCE TO RELATED APPLICATIONS

This application is a continuation of U.S. application Ser. No. 14/766,632, filed Aug. 7, 2015, which is a 35 U.S.C. §371 national stage filing of International Application No. PCT/US2014/015706, filed Feb. 11, 2014, which claims priority to International Application No. PCT/US2013/025639, filed Feb. 11, 2013.

BACKGROUND OF THE INVENTION

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

SUMMARY OF THE INVENTION

The present disclosure encompasses the recognition that methyl modifying enzymes are an attractive target for modulation, given their role in the regulation of diverse biological processes. It has now been found that compounds of this invention, and pharmaceutically acceptable compositions thereof, are effective as agents that stimulate activity of histone methyl modifying enzymes, including histone methylases and histone demethylases. Such compounds have the general formula II:

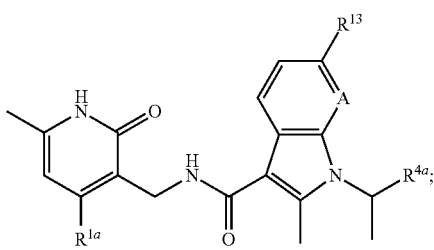

or a pharmaceutically acceptable salt thereof, wherein each variable is as defined herein.

Compounds of the present invention, and pharmaceutically acceptable compositions thereof, are useful for treating a variety of diseases, disorders or conditions, associated with a methyl modifying enzyme. Such diseases, disorders, or conditions include those described herein.

Compounds provided by this invention are also useful for the study of methyl modifying enzymes in biological and pathological phenomena; the study of intracellular signal transduction pathways mediated by methyl modifying enzymes and the comparative evaluation of new methyl modifying enzyme modulators.

DETAILED DESCRIPTION OF CERTAIN EMBODIMENTS

Figure 1:
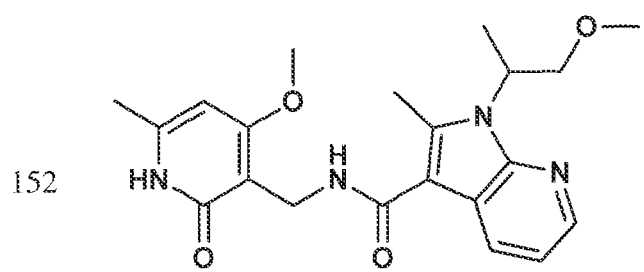
FIG. 1. Exemplary compounds of Formula II.
Figure 1:
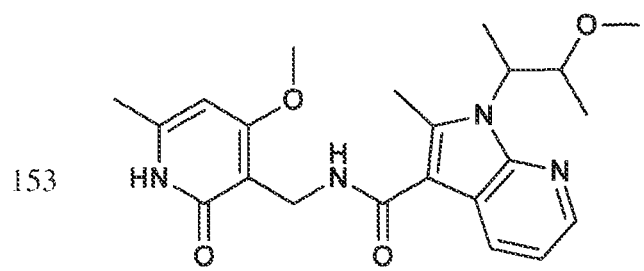
Figure 1:
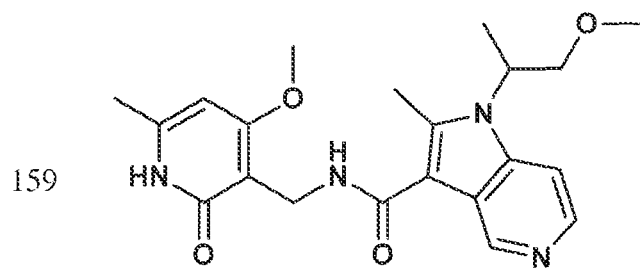
Figure 1:
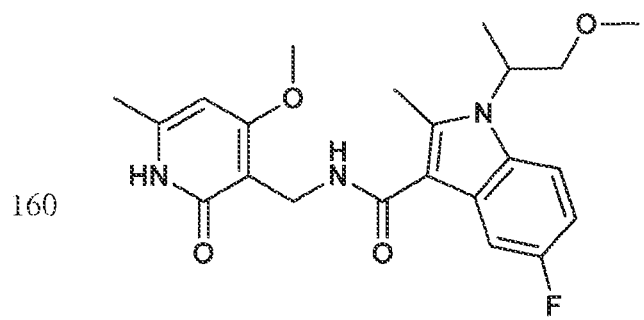
Figure 1:
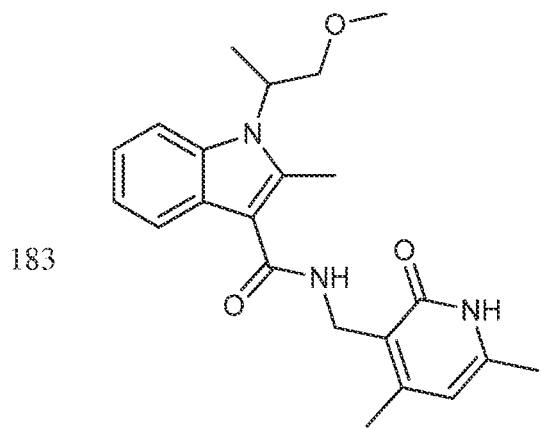
Figure 1:
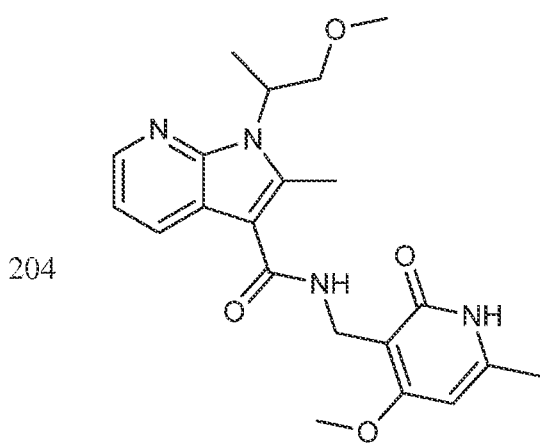
Figure 1:
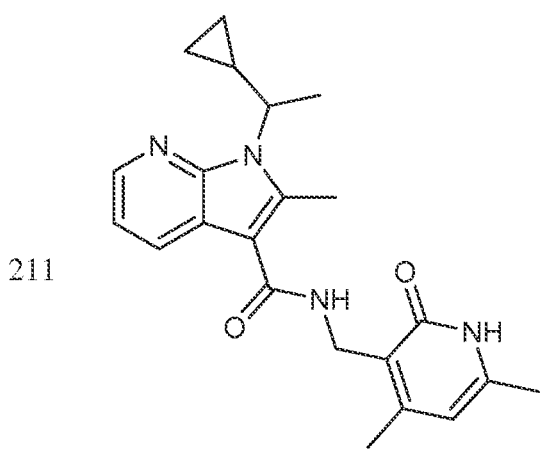
Figure 1:
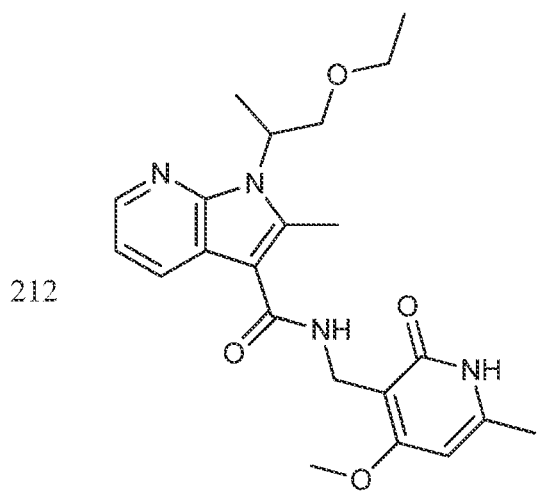
Figure 1:
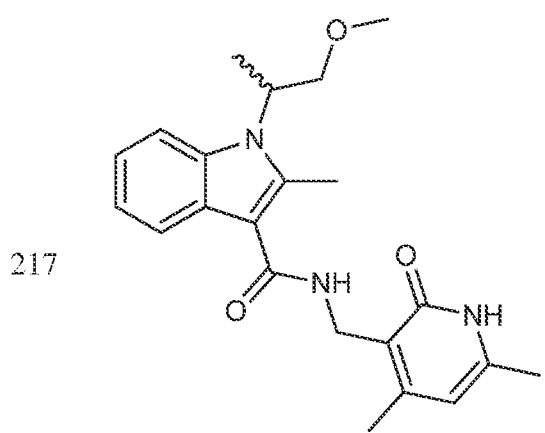
Figure 1:
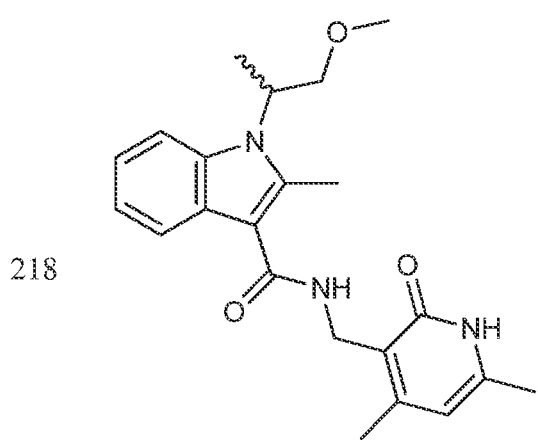
Figure 1:
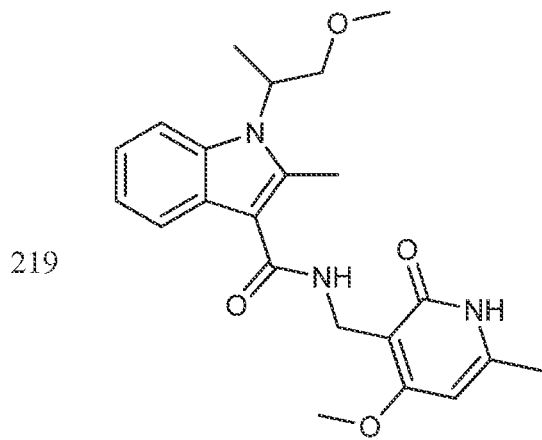
Figure 1:
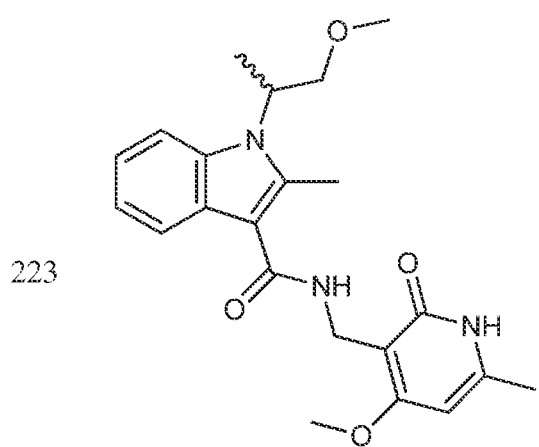
Figure 1:
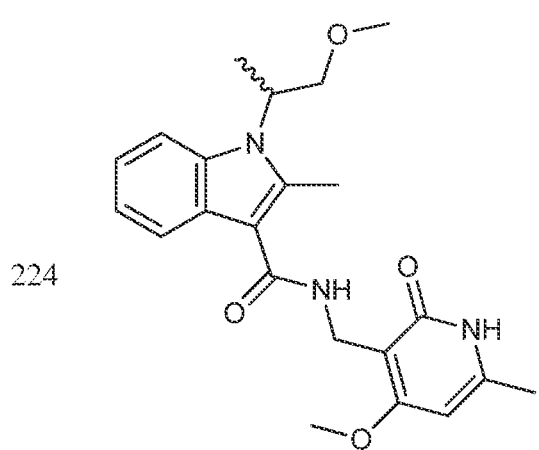
Figure 1:
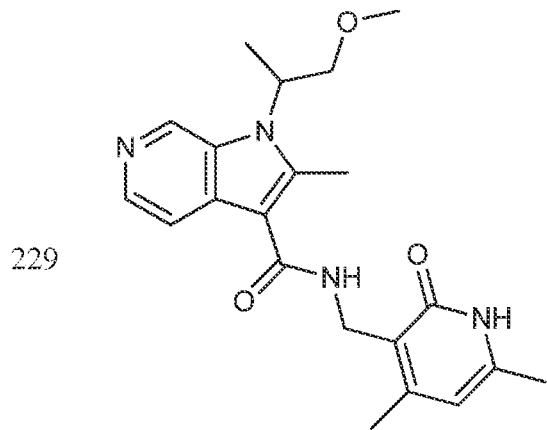
Figure 1:
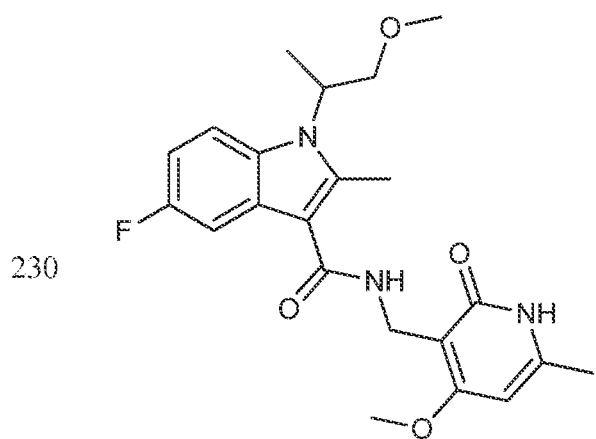
Figure 1:
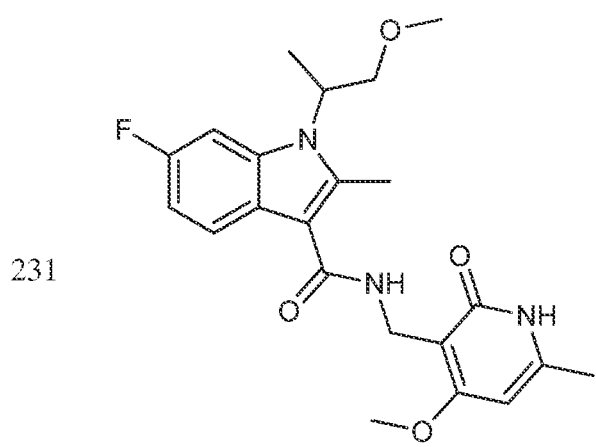
Figure 1:
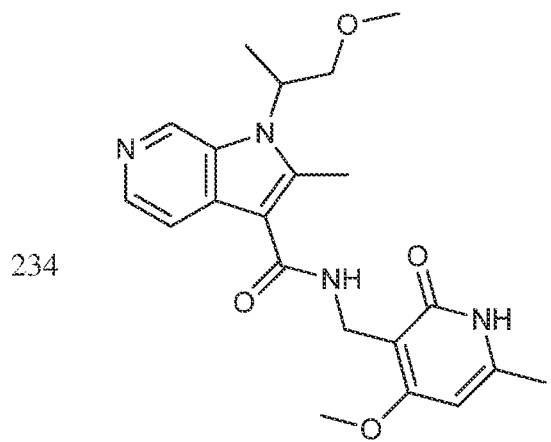
Figure 1:
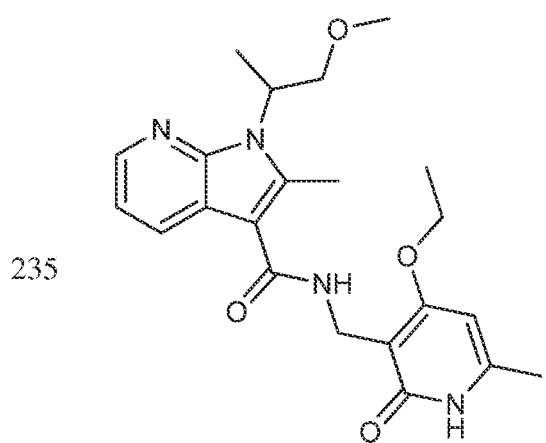
Figure 1:
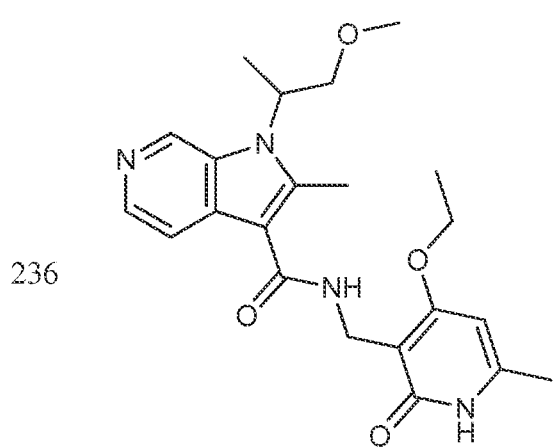
Figure 1:
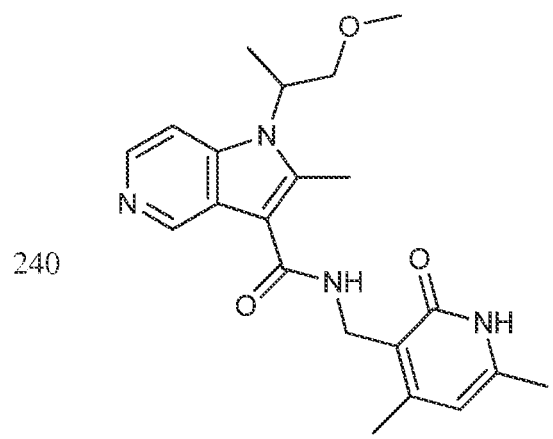
Figure 1:
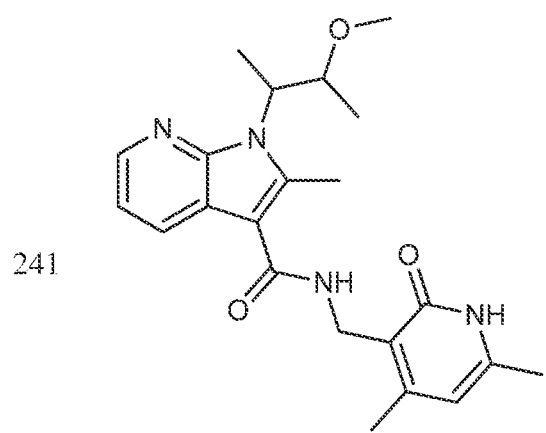
Figure 1:
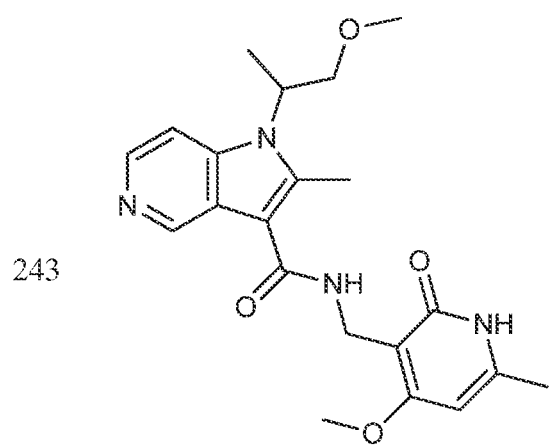
Figure 1:
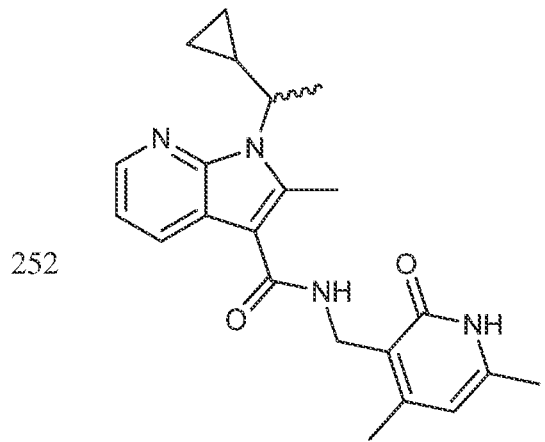
Figure 1:
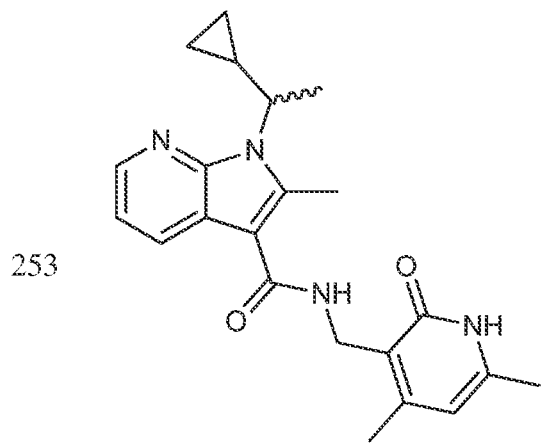
Figure 1:
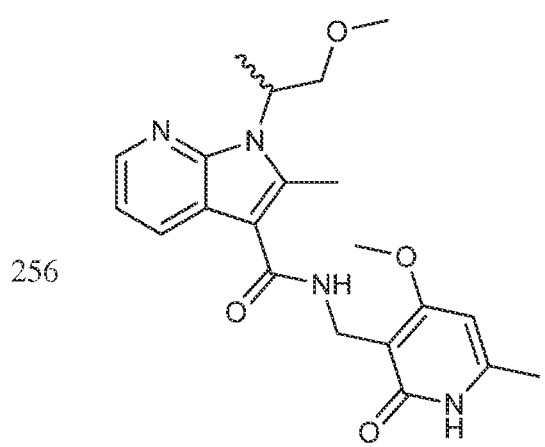
Figure 1:
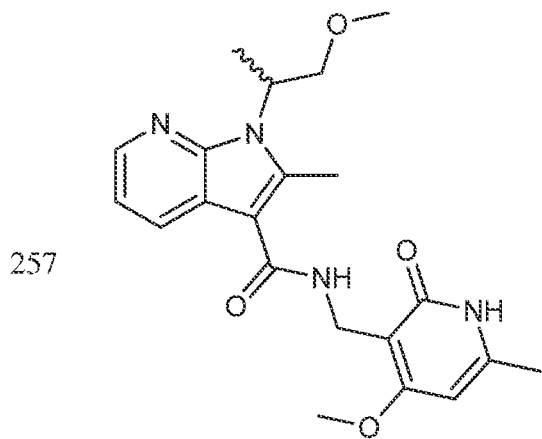
Figure 1:
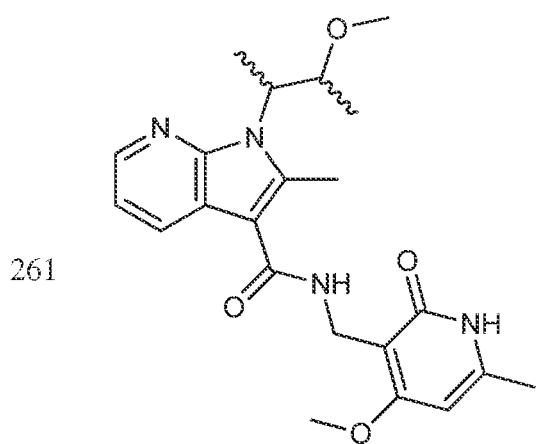
Figure 1:
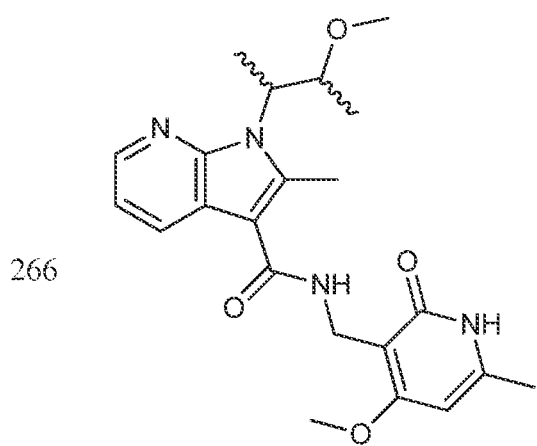
Figure 1:
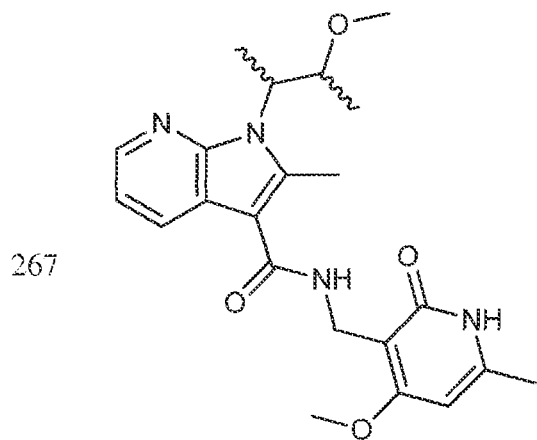
Figure 1:
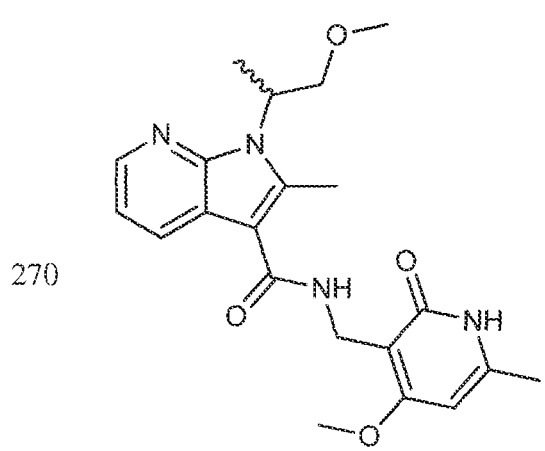
Figure 1:
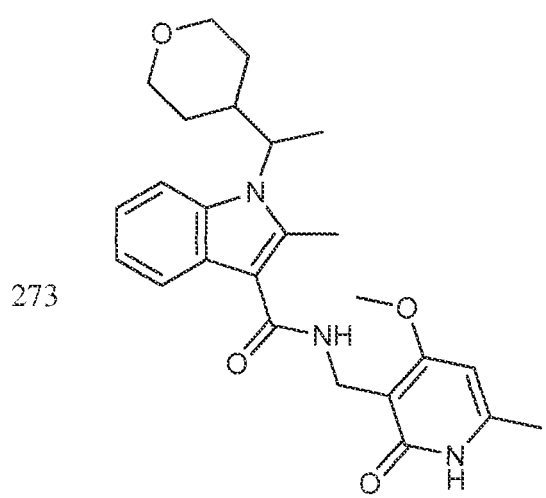
Figure 1:
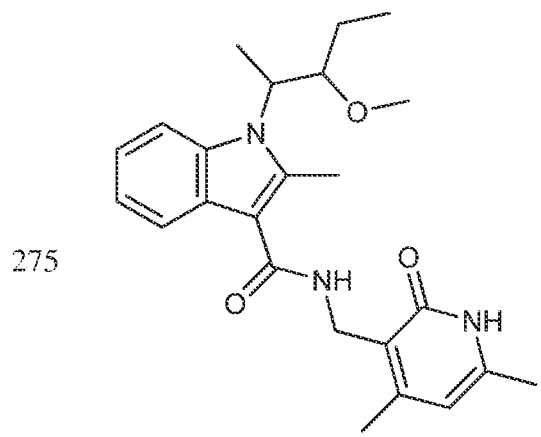
Figure 1:
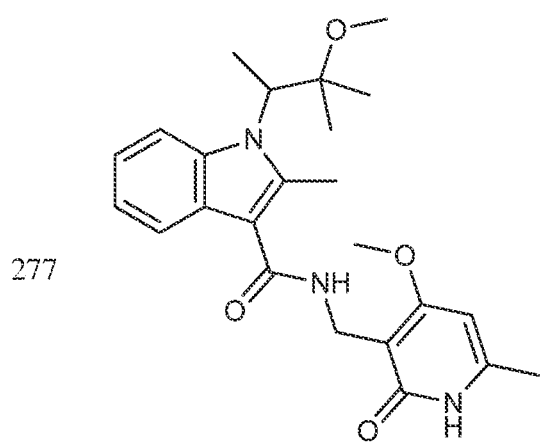
Figure 1:
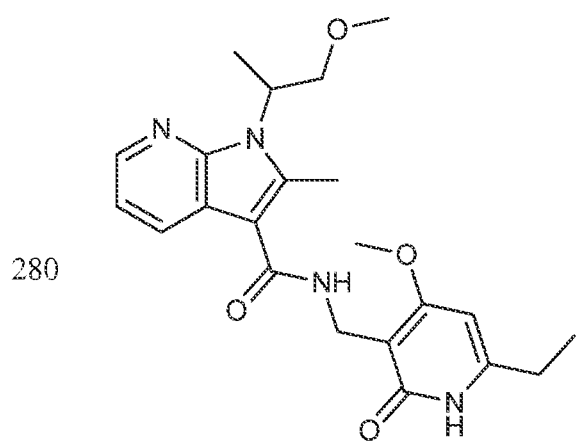
Figure 1:
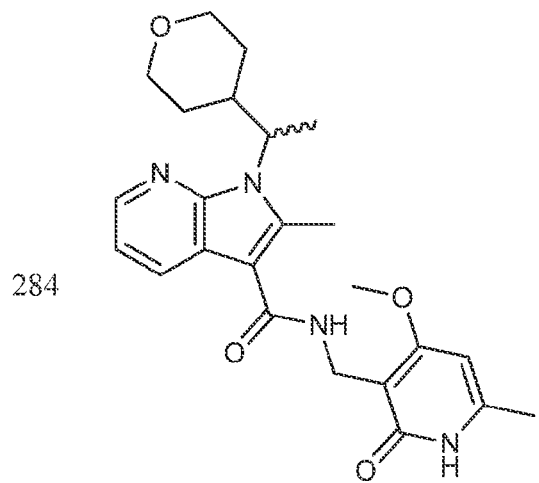
Figure 1:
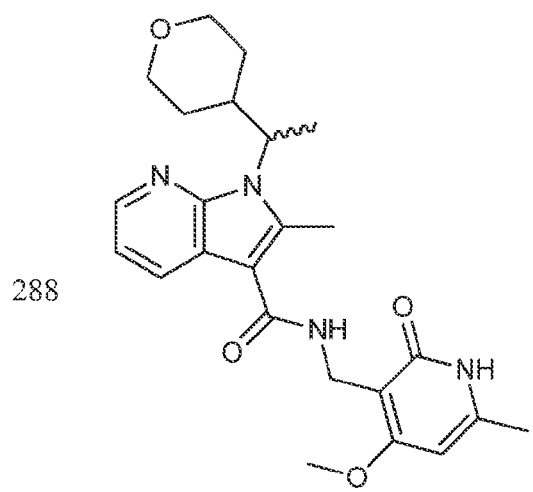
Figure 1:
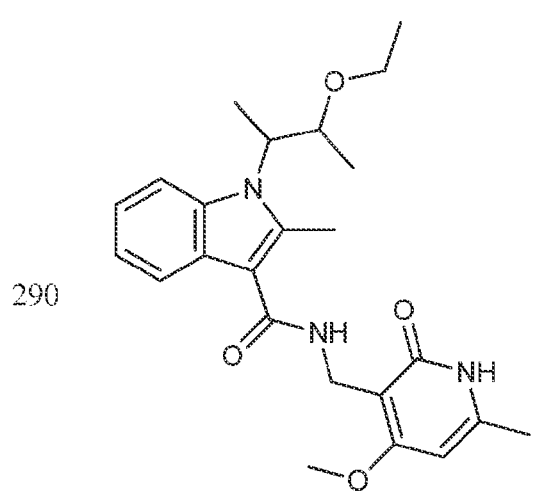
Figure 1:
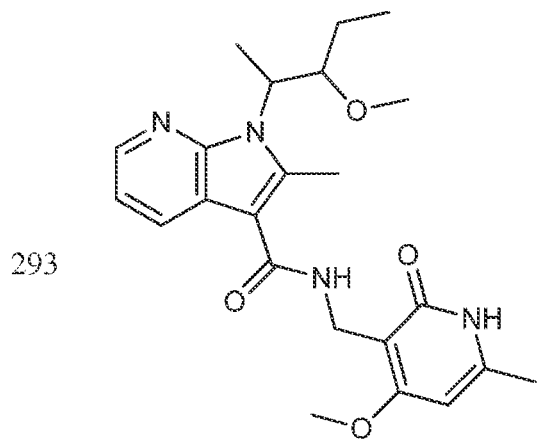
Figure 1:
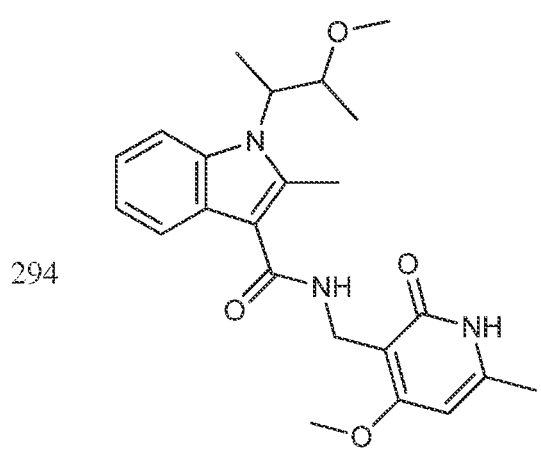
Figure 1:
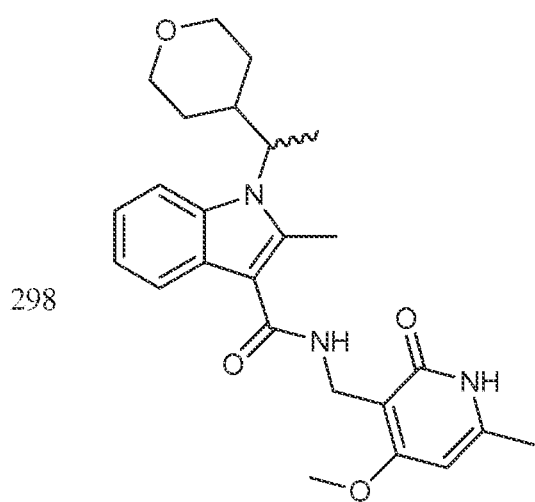
Figure 1:
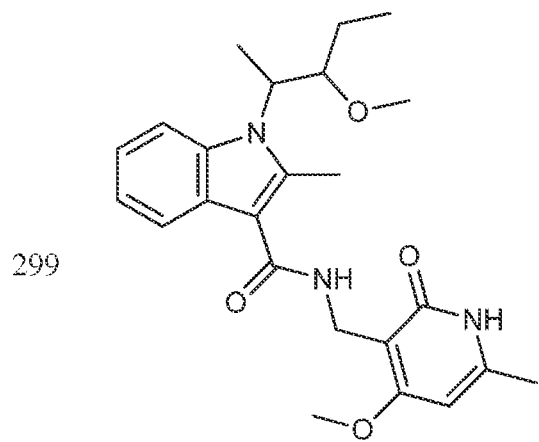
Figure 1:
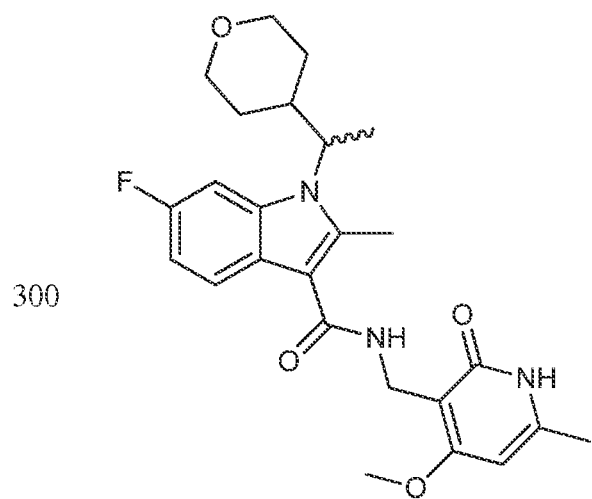
Figure 1:
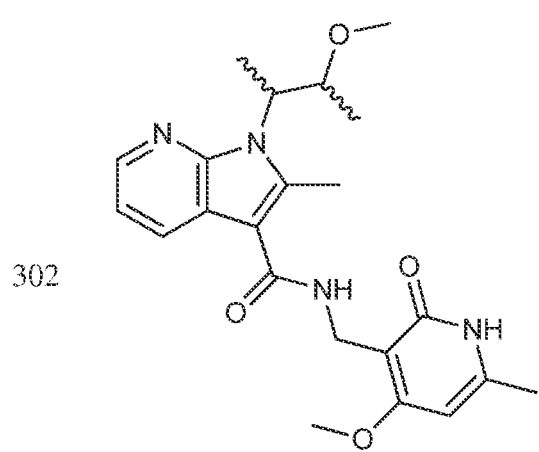
Figure 1:
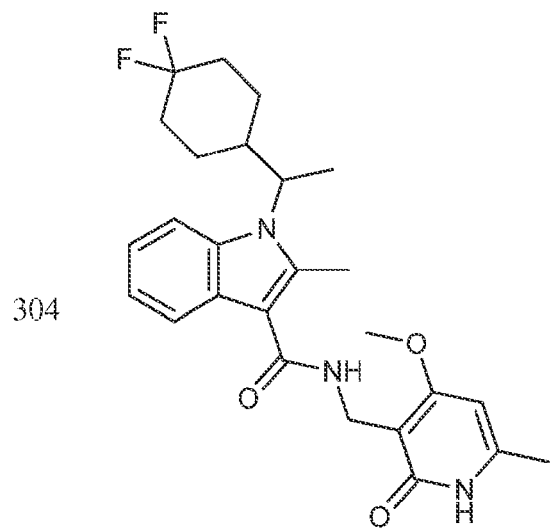
Figure 1:
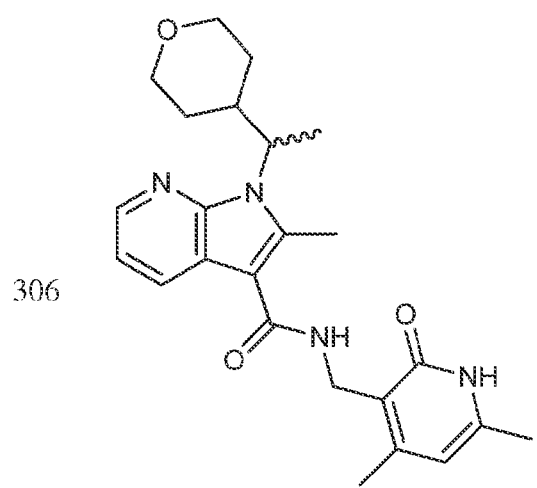
Figure 1:
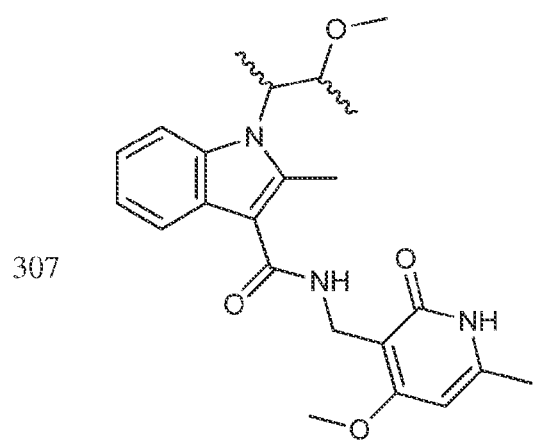
Figure 1:
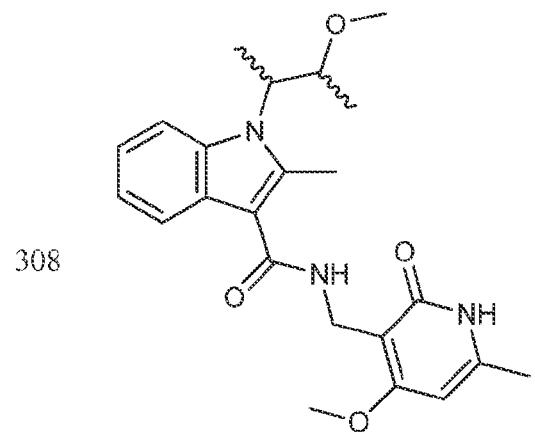
Figure 1:
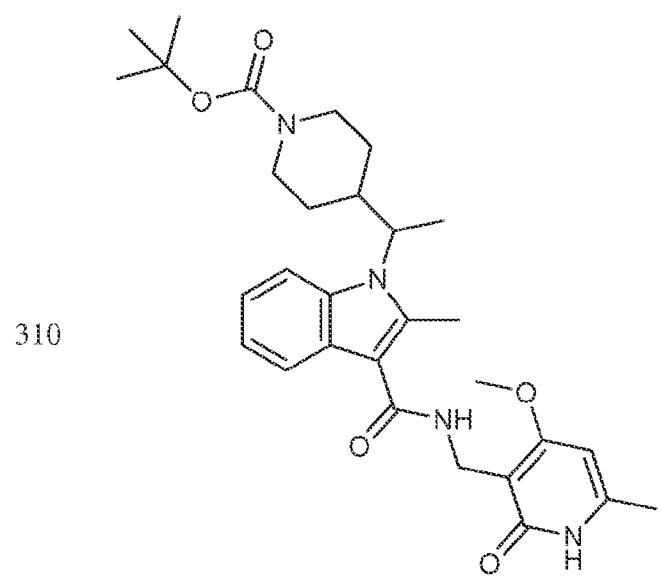
Figure 1:
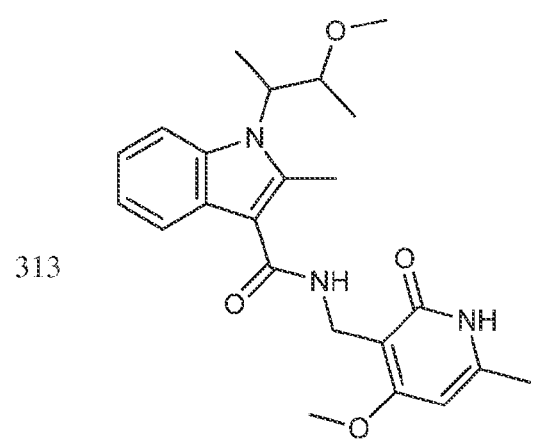
Figure 1:
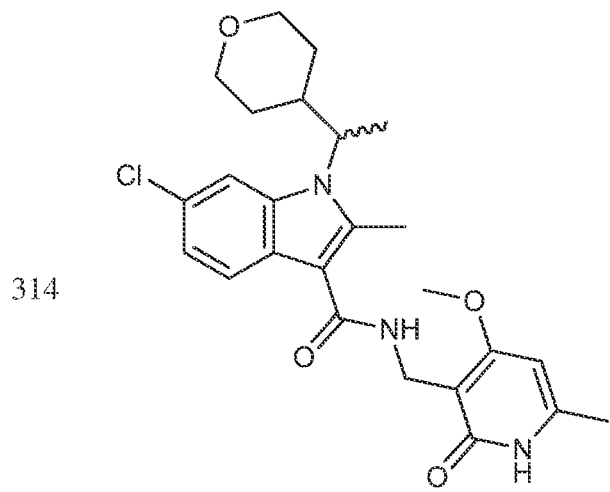
Figure 1:
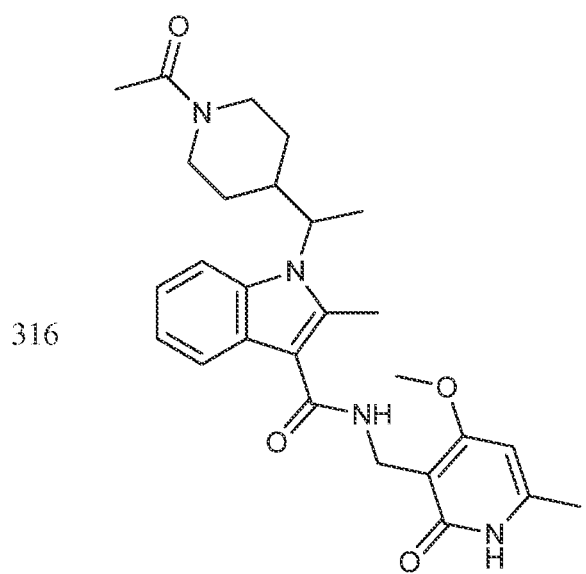
Figure 1:
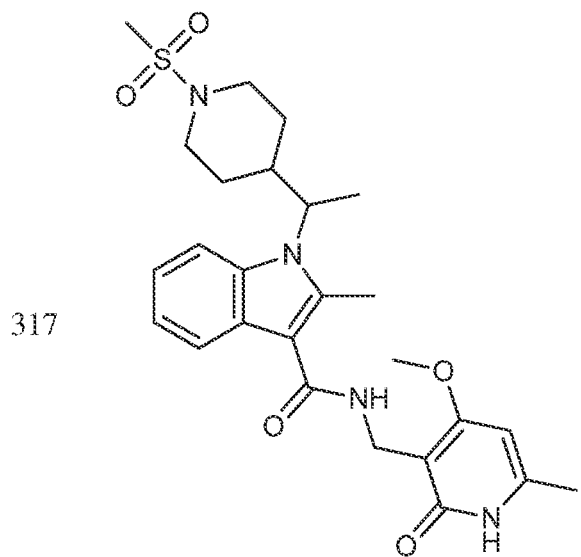
Figure 1:
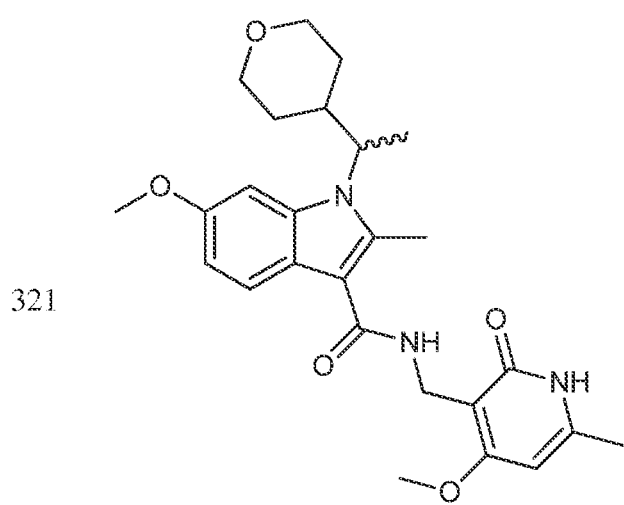
Figure 1:
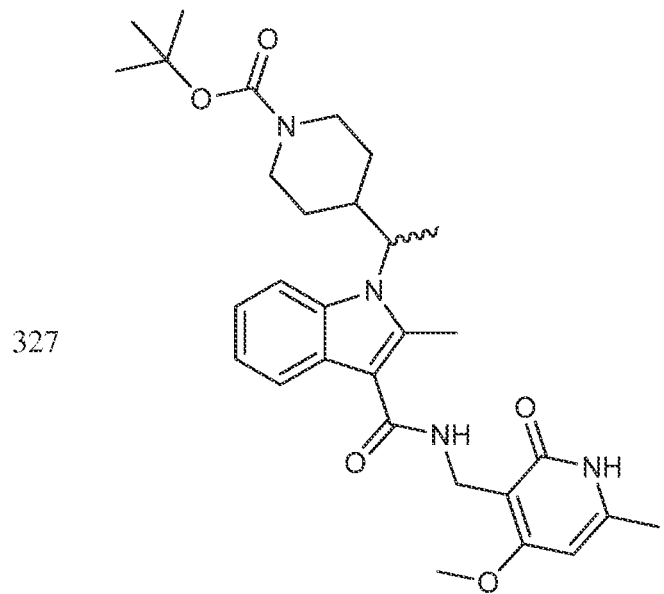
Figure 1:
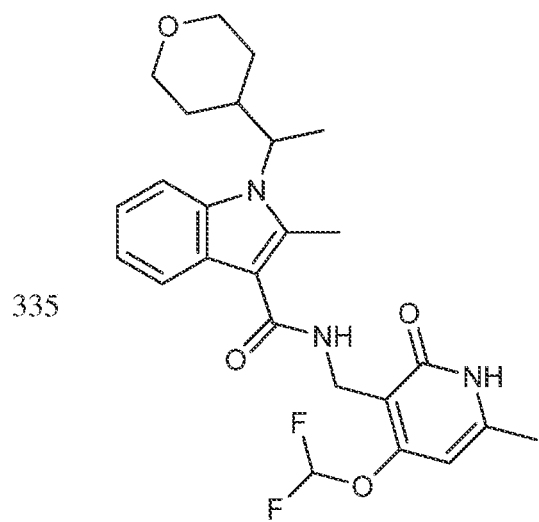
Figure 1:
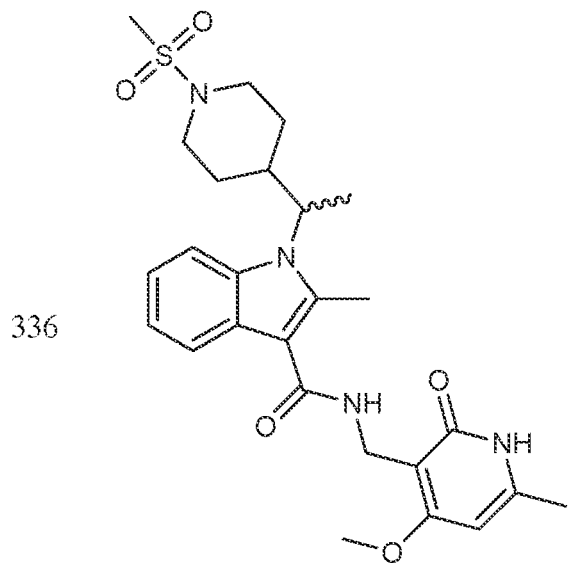
Figure 1:
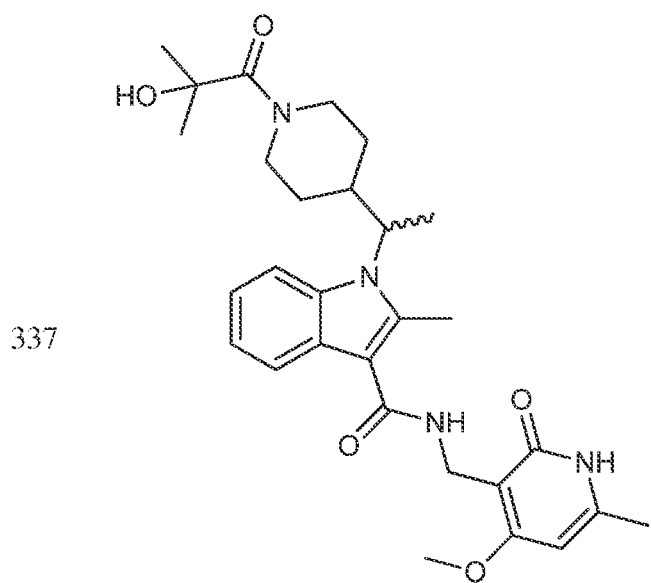
Figure 1:
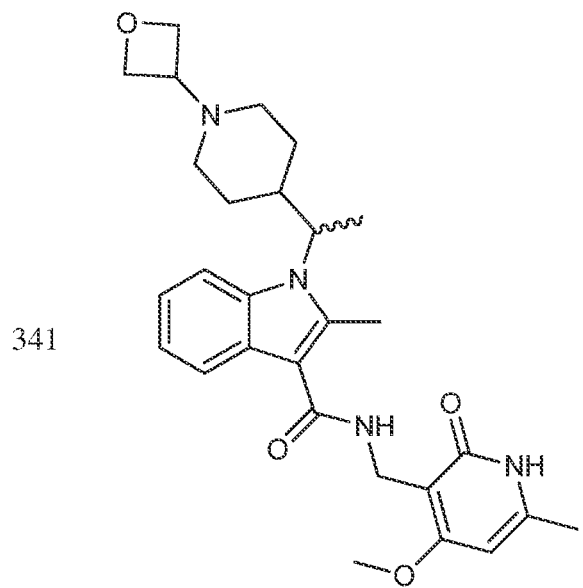
Figure 1:
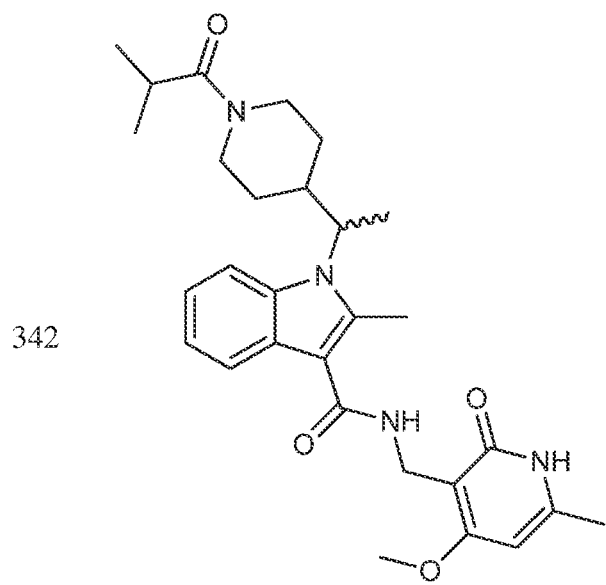
Figure 1:
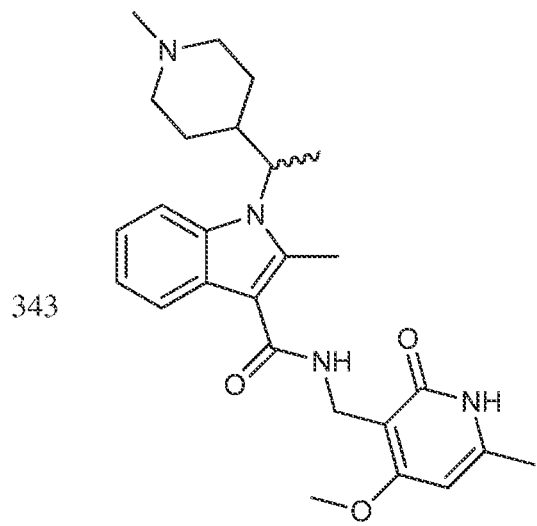
Figure 1:
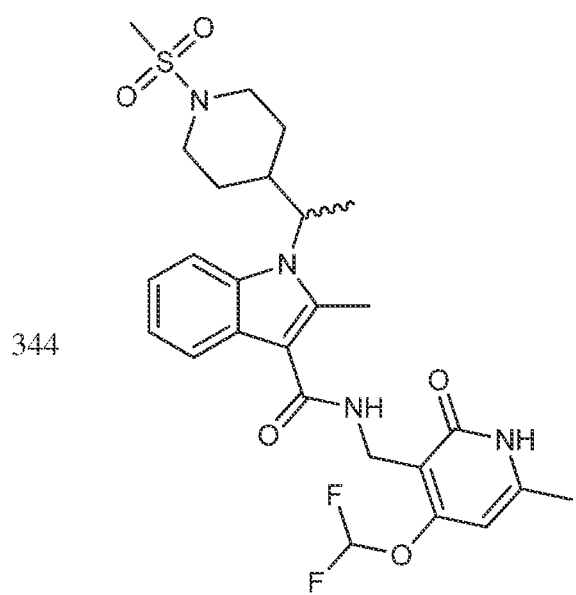
Figure 1:
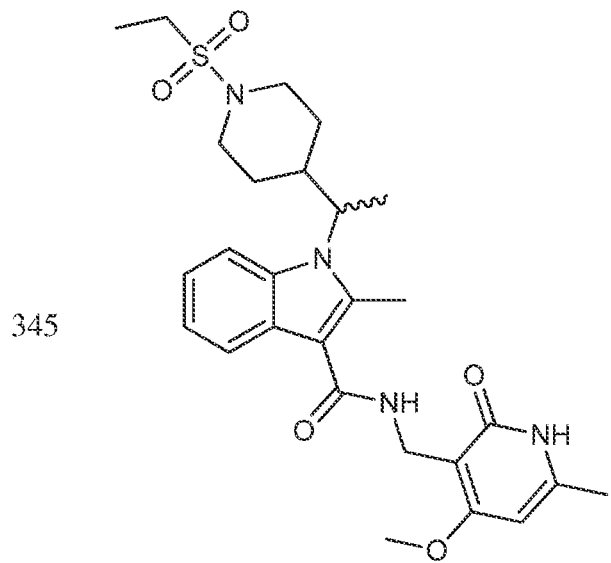
Figure 1:
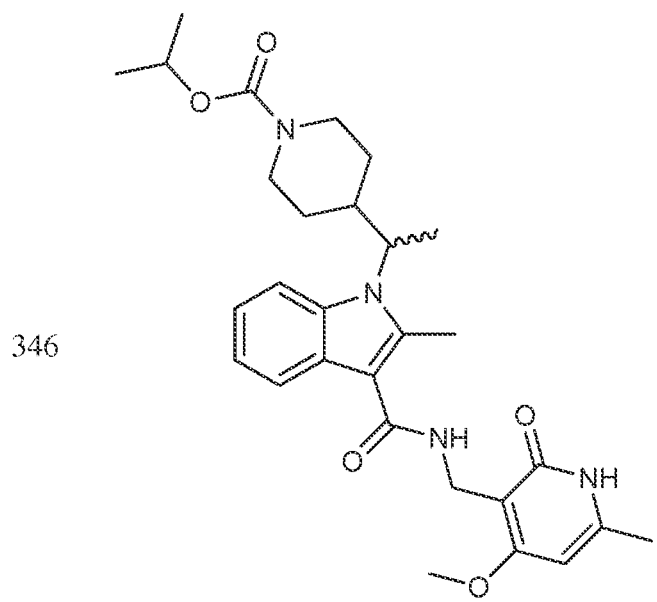
Figure 1:
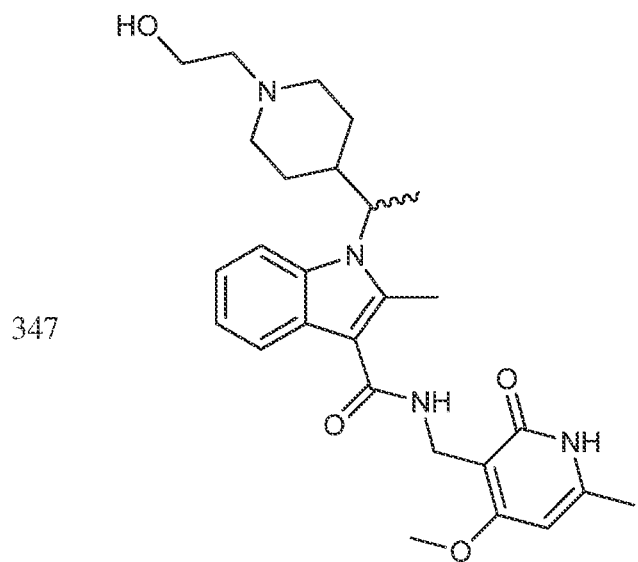
Figure 1:
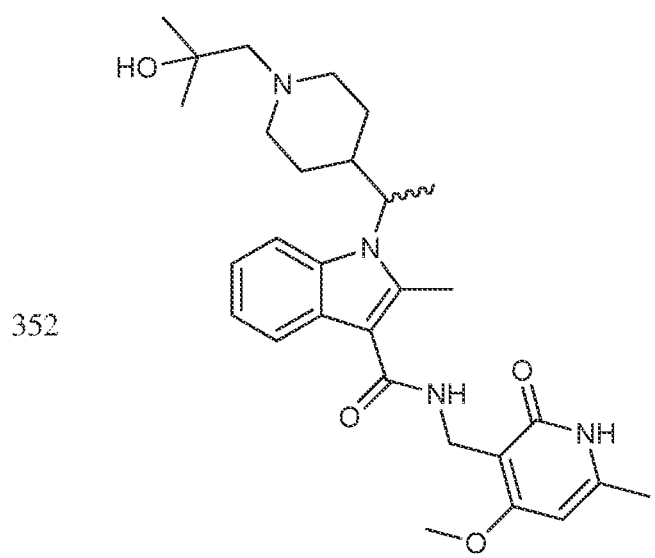
Figure 1:
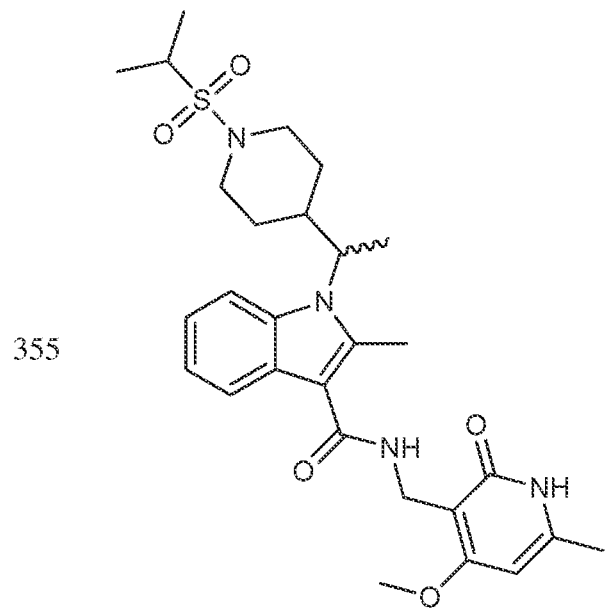
Figure 1:
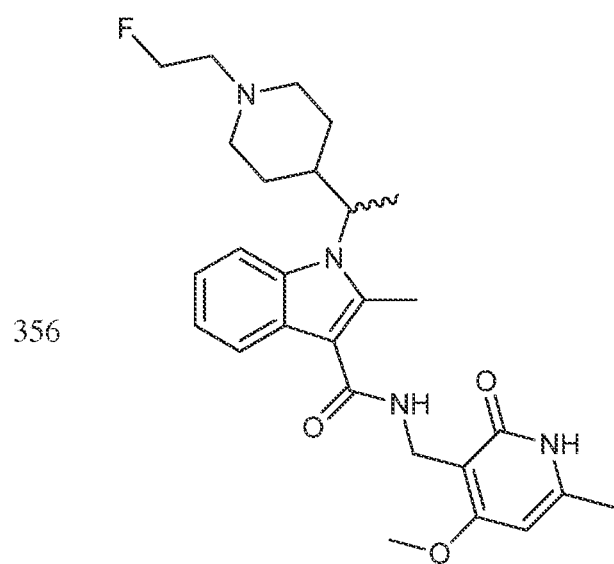
Figure 1:
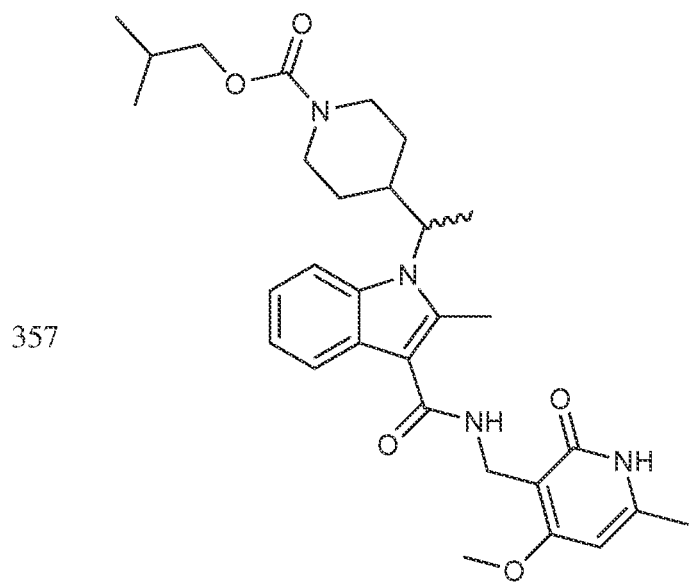
Figure 1:
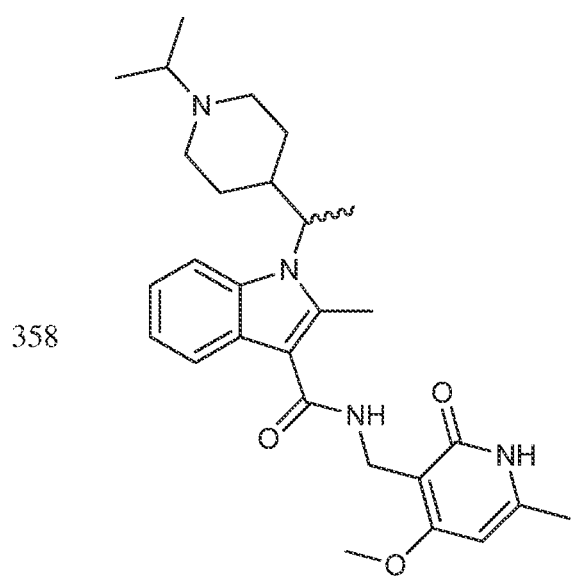
Figure 1:
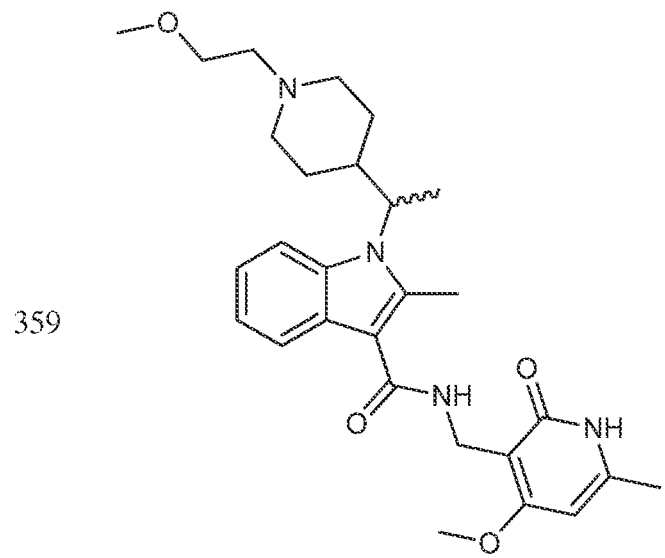
Figure 1:
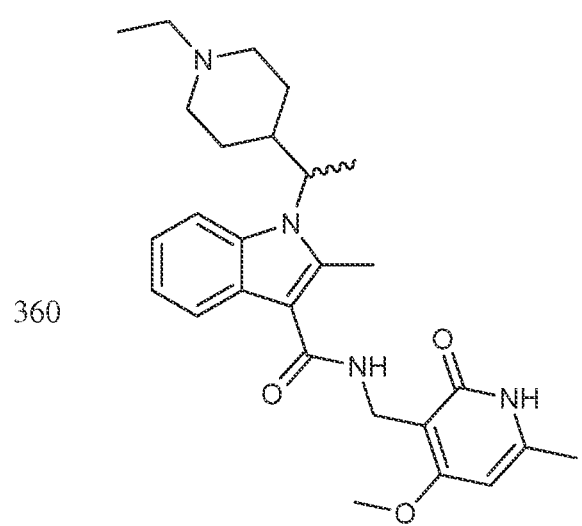
Figure 1:
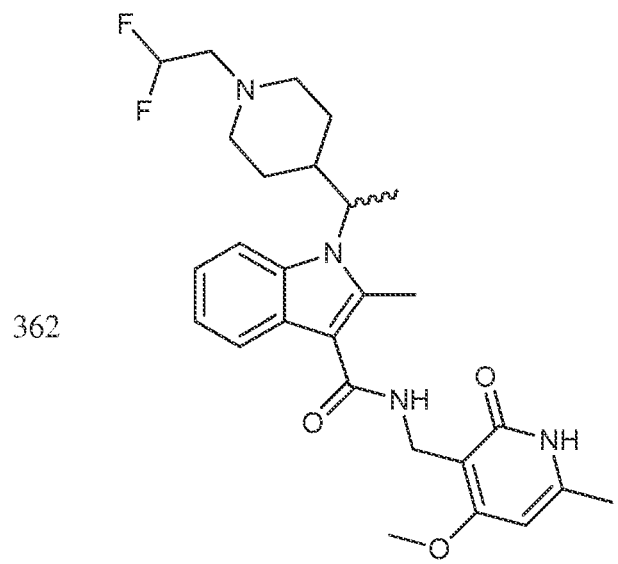
Figure 1:
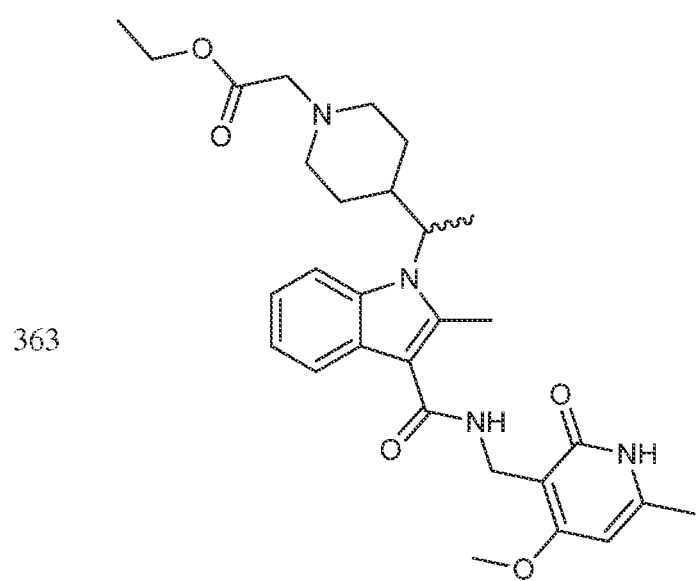
Figure 1:
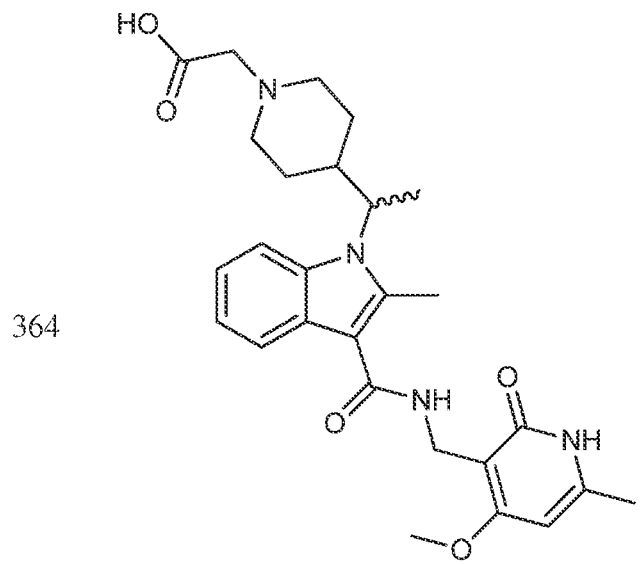
Figure 1:
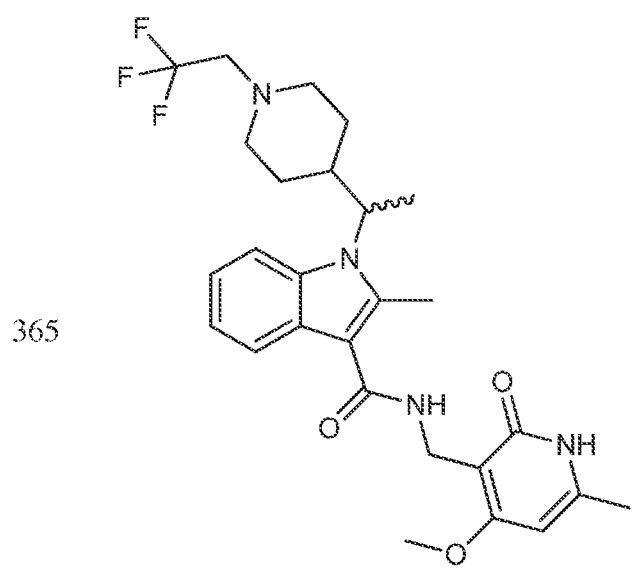
Figure 1:
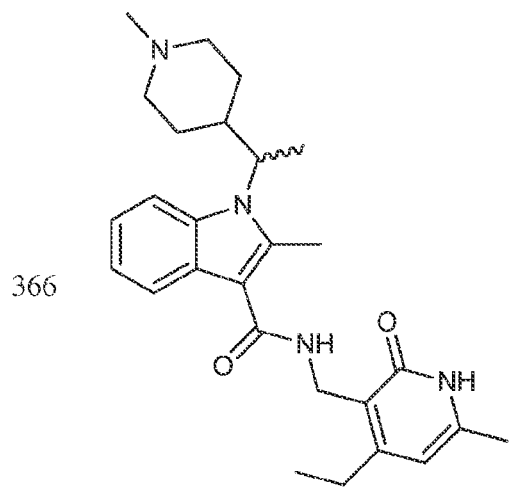
Figure 1:
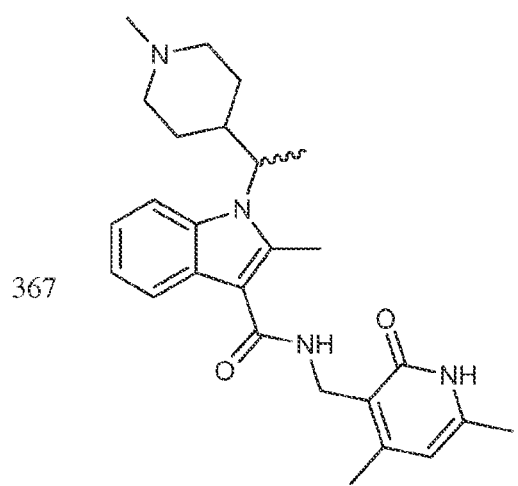
Figure 1:
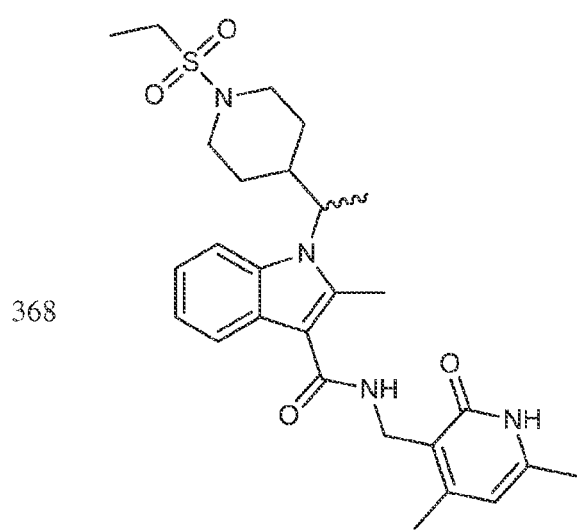
Figure 1:
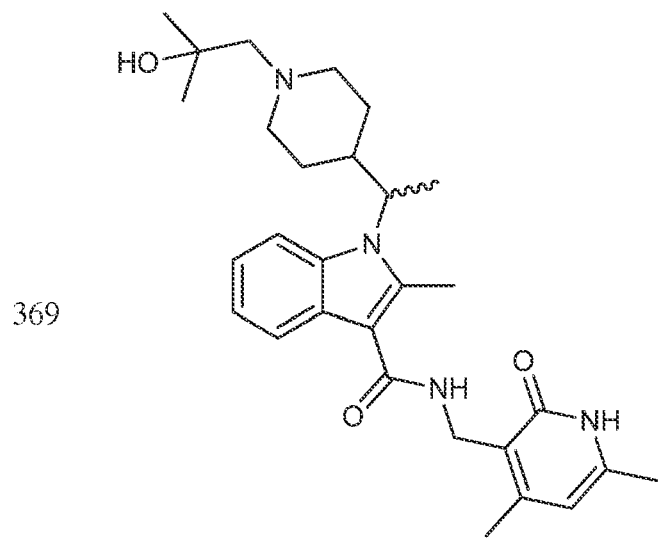
Figure 1:
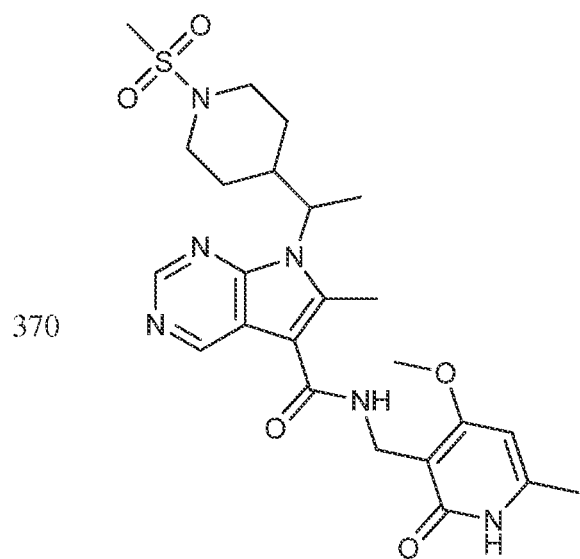
Figure 1:
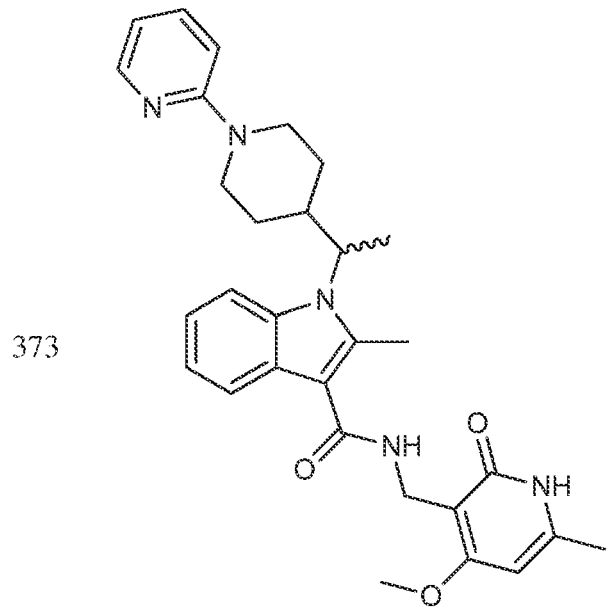
Figure 1:
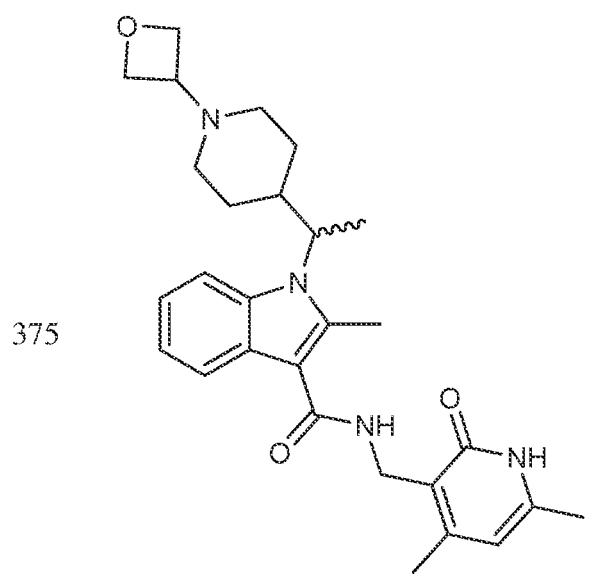
Figure 1:
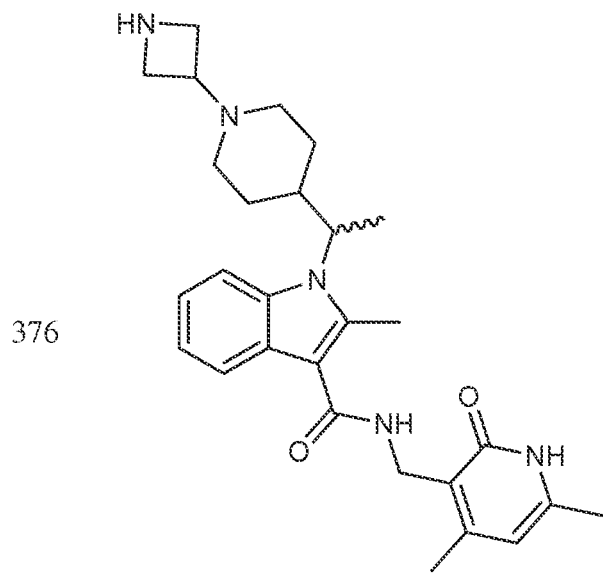
Figure 1:
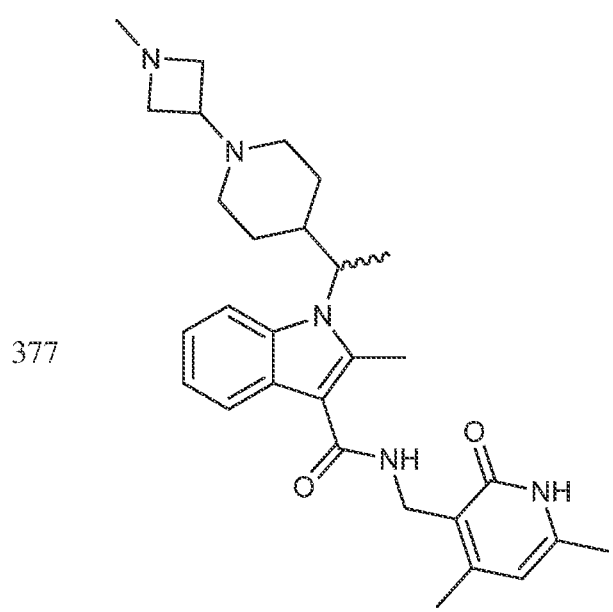
Figure 1:
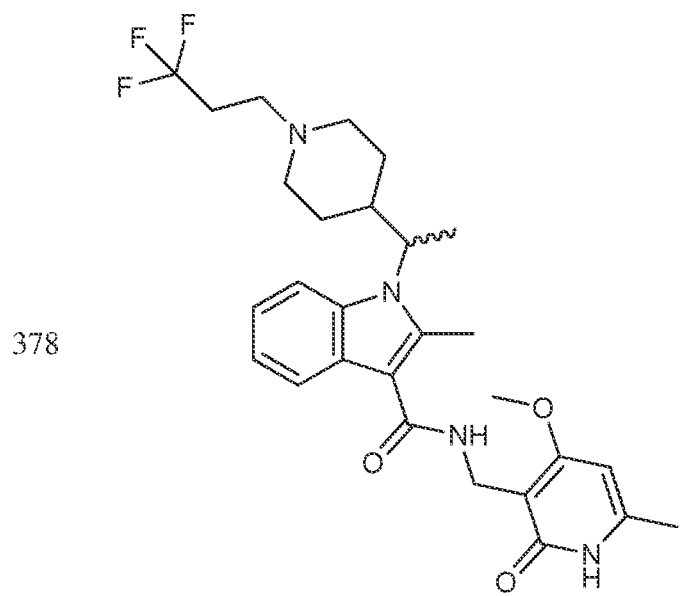
Figure 1:
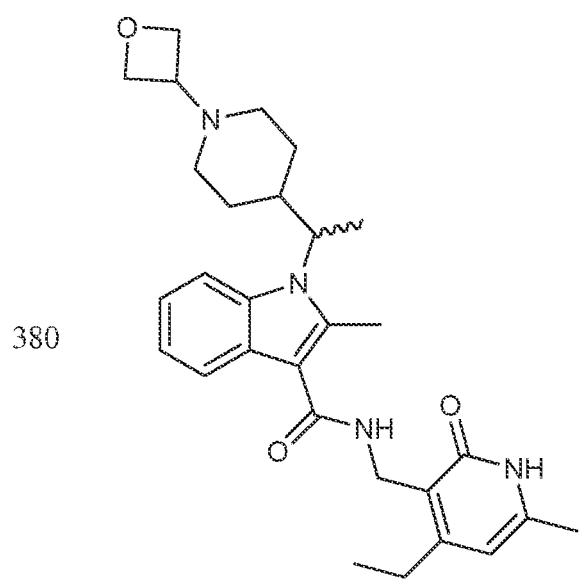
Figure 1:
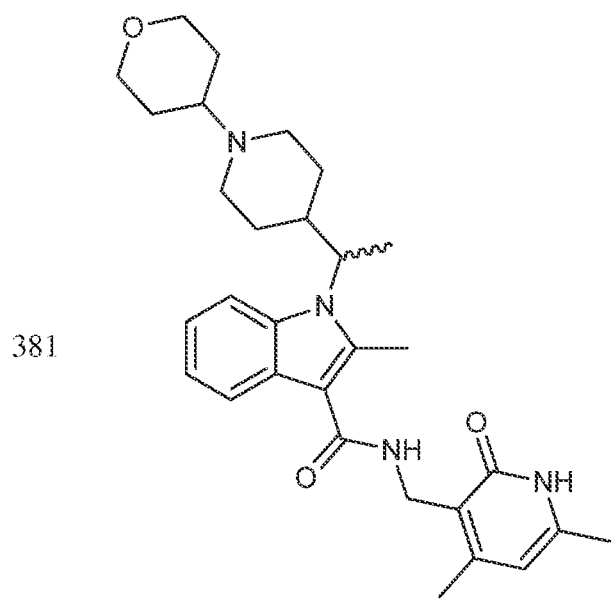
Figure 1:
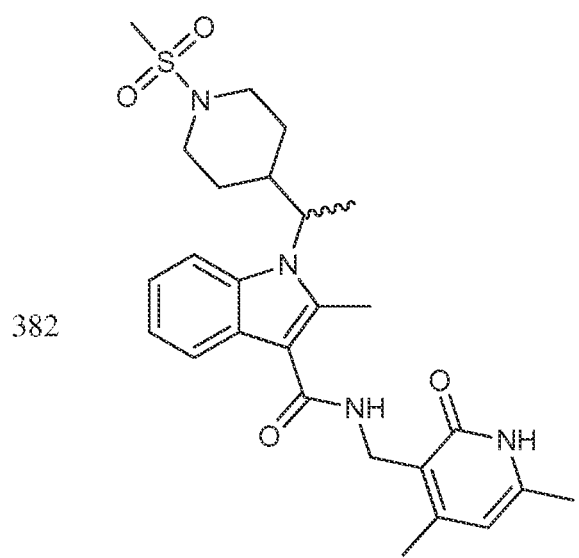
Figure 1:
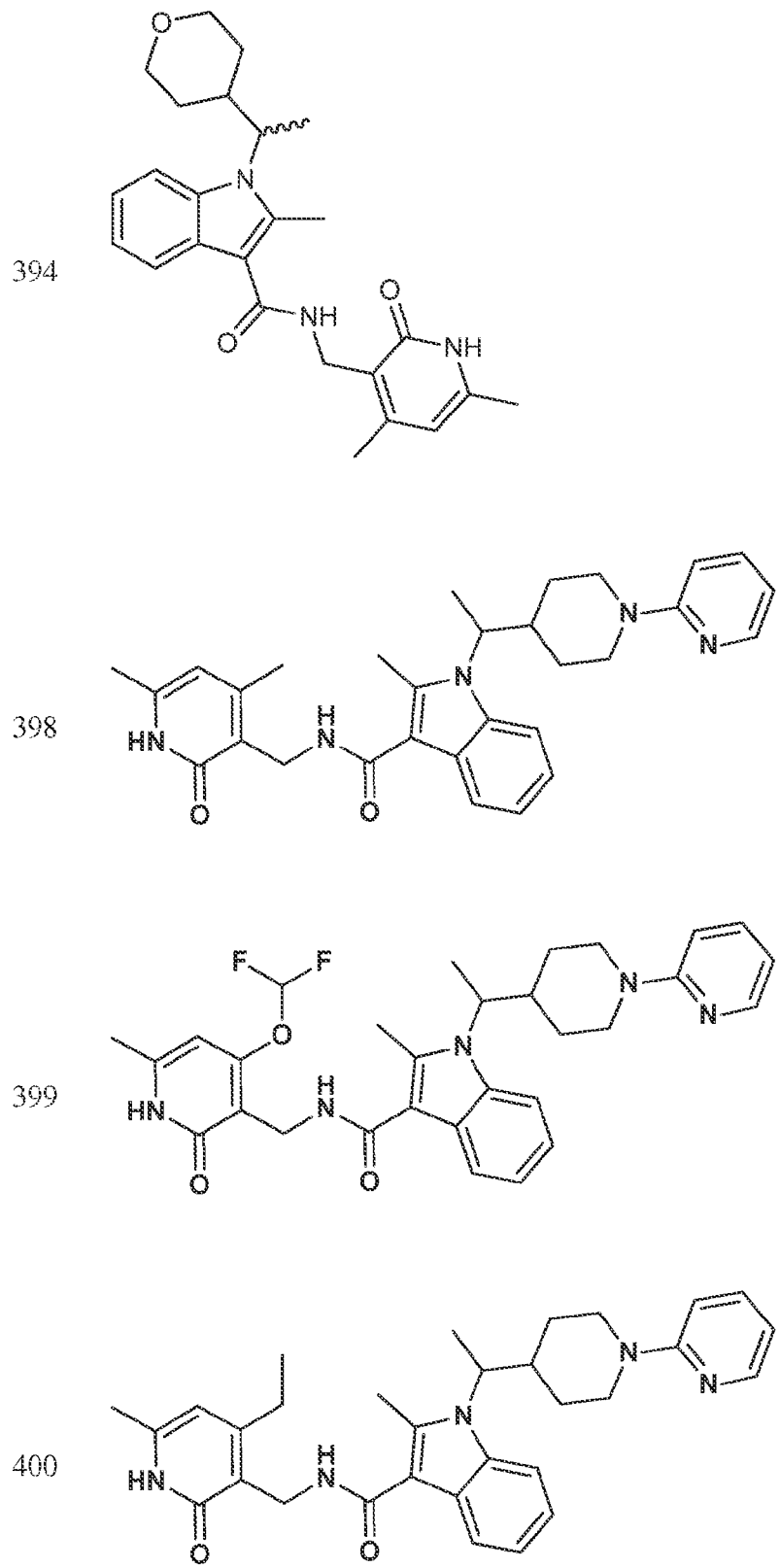
Figure 1:
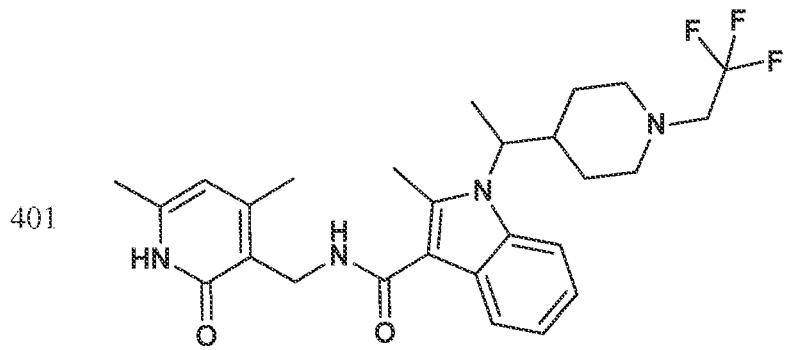
Figure 1:
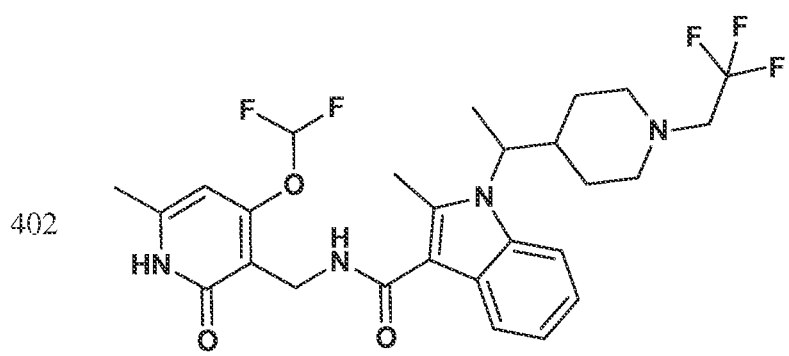
Figure 1:
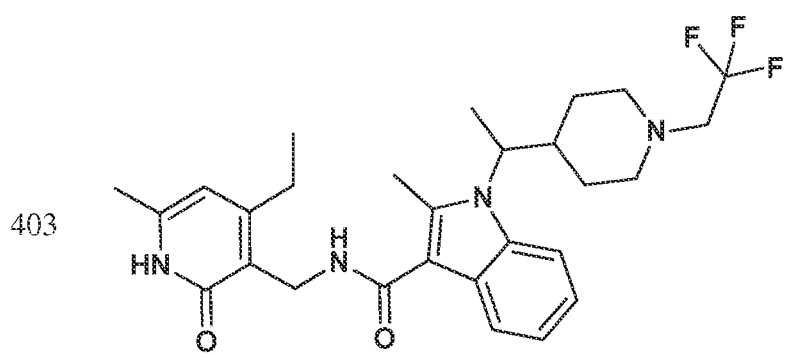
Figure 1:
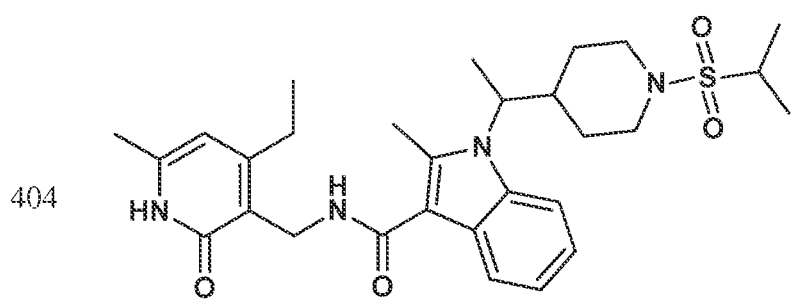
Figure 1:
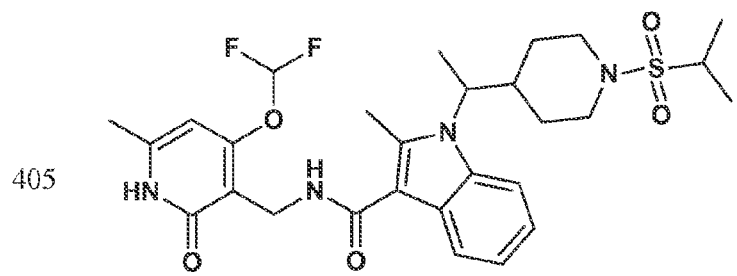
Figure 1:
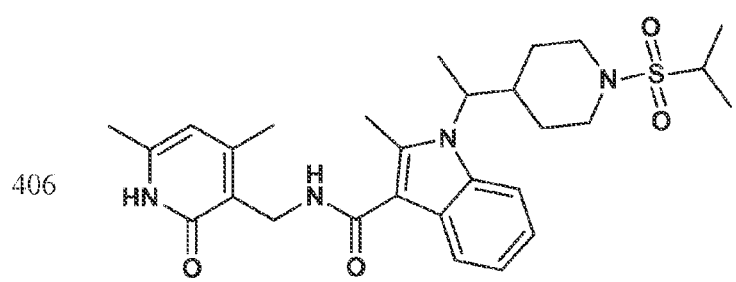
Figure 1:
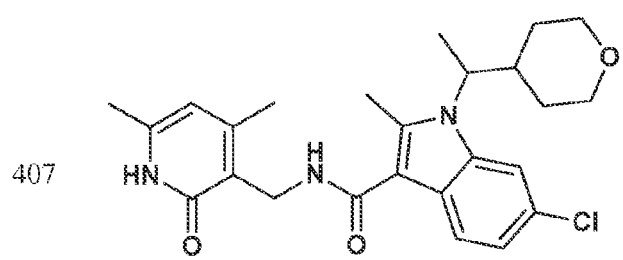
Figure 1:
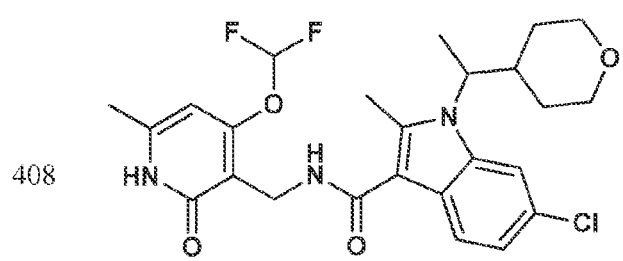
Figure 1:
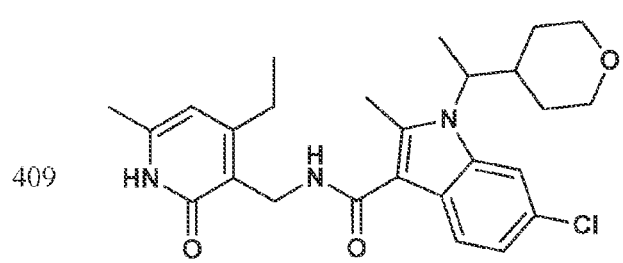
Figure 1:
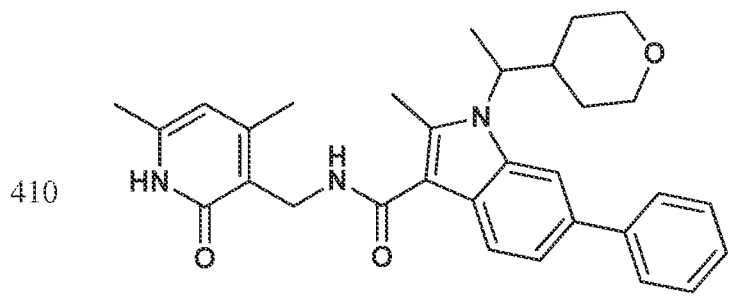
Figure 1:
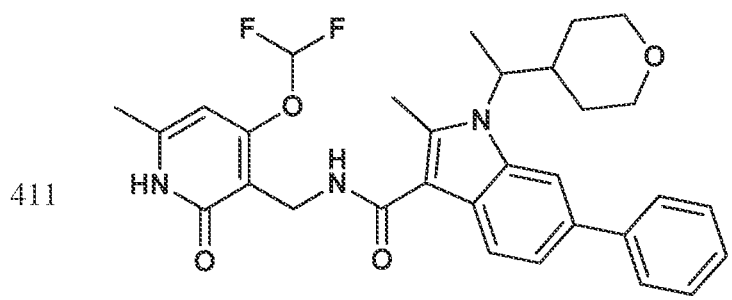
Figure 1:
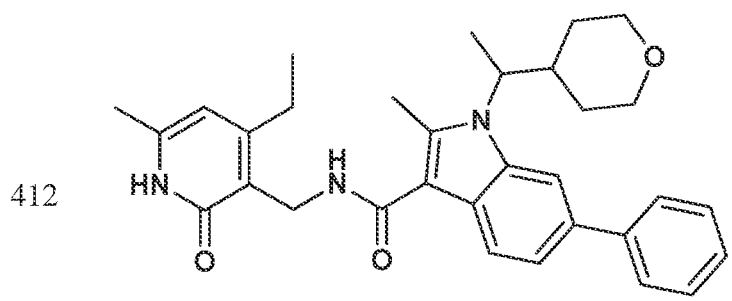
Figure 1:
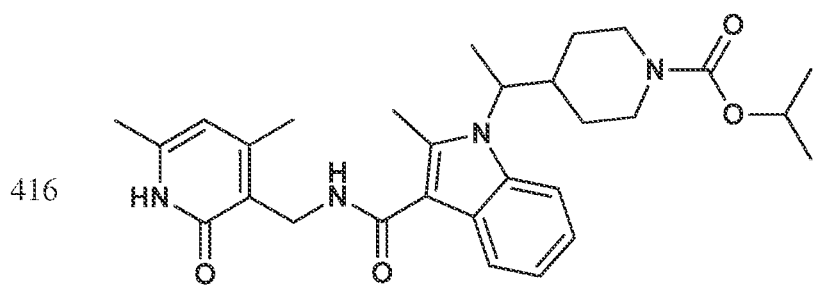
Figure 1:
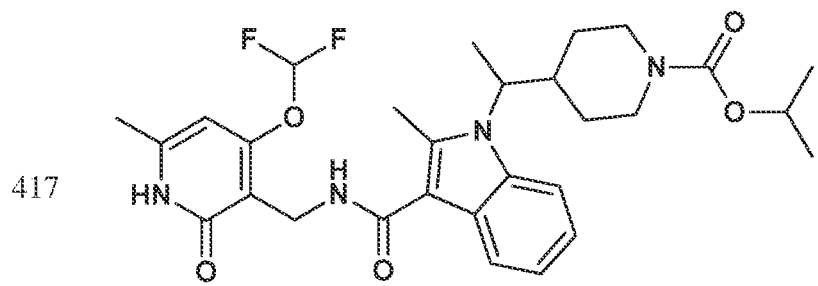
Figure 1:
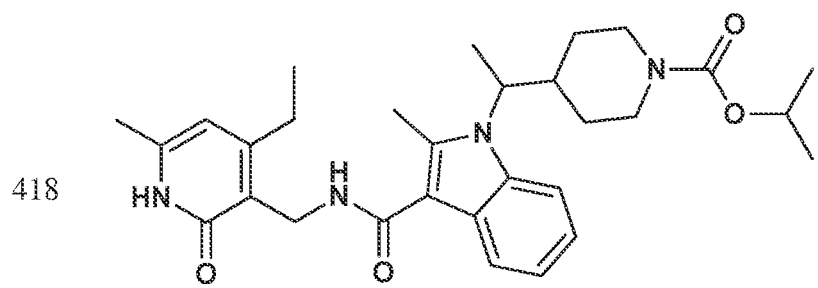
Figure 1:
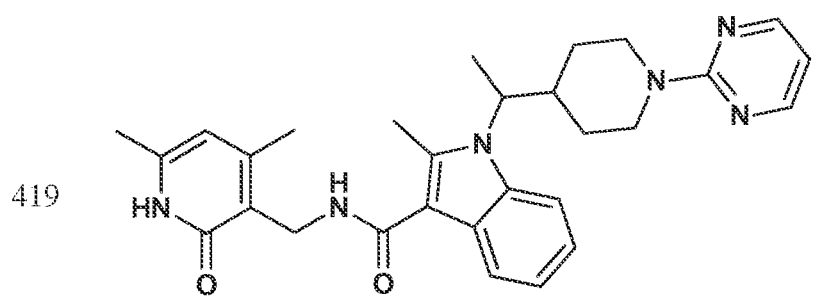
Figure 1:
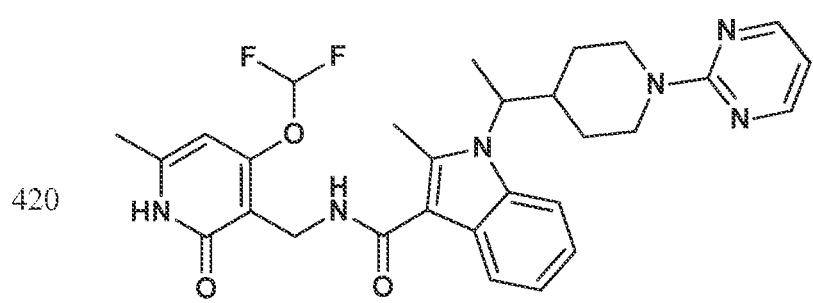
Figure 1:
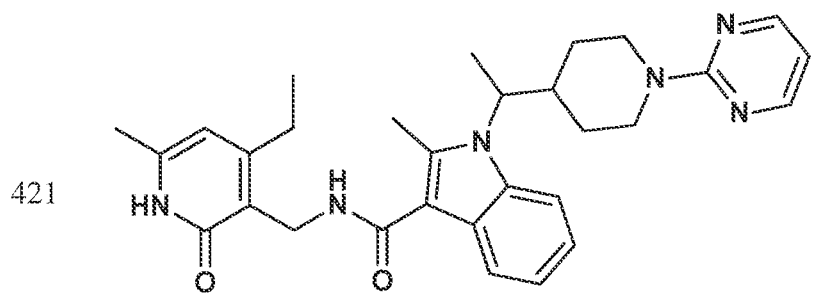
Figure 1:
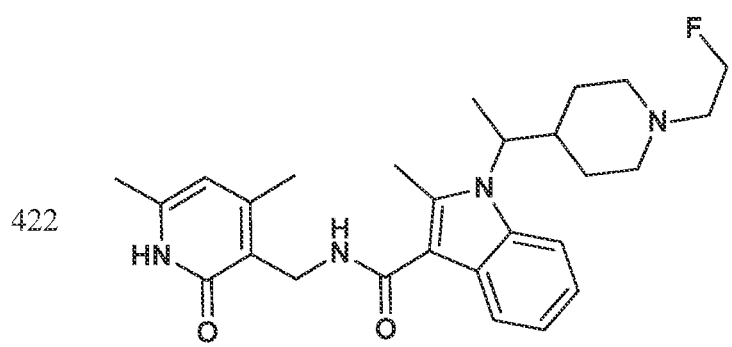
Figure 1:
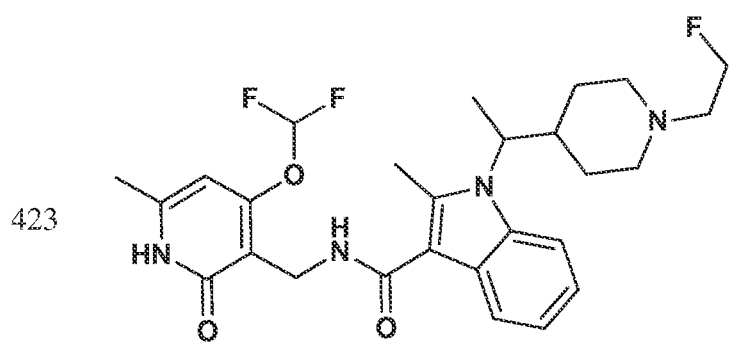
Figure 1:
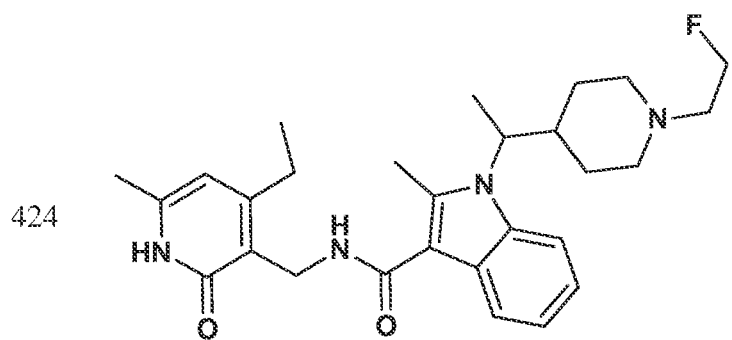
Figure 1:
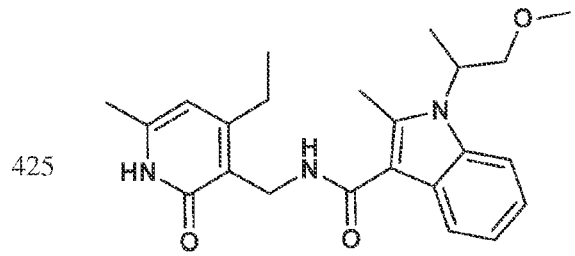
Figure 1:
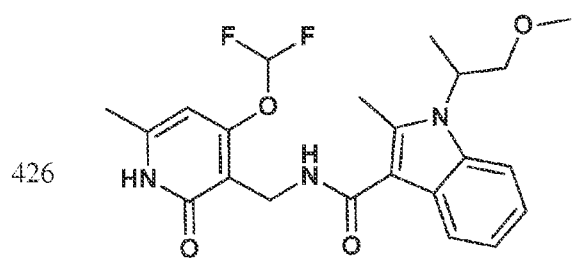
Figure 1:
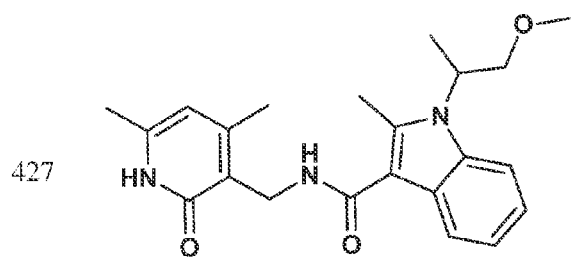
Figure 1:
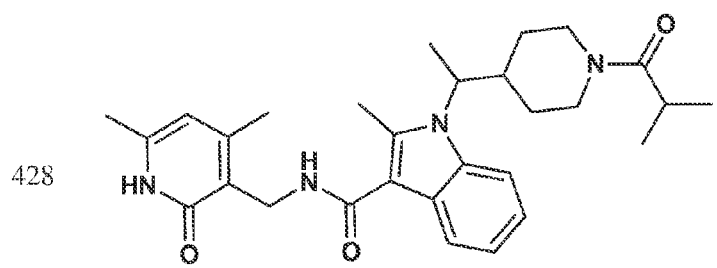
Figure 1:
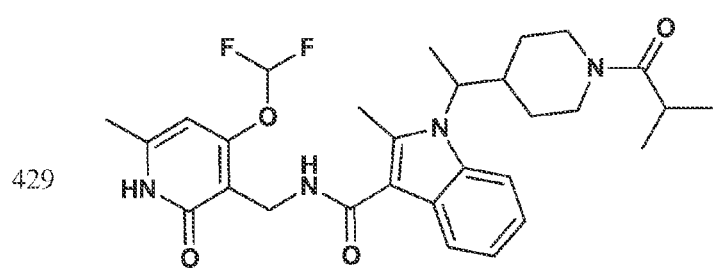
Figure 1:
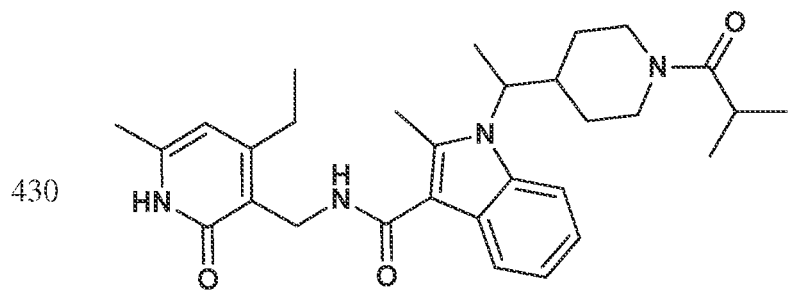
Figure 1:
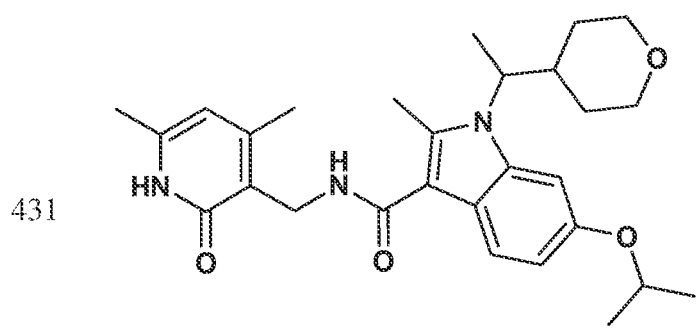
Figure 1:
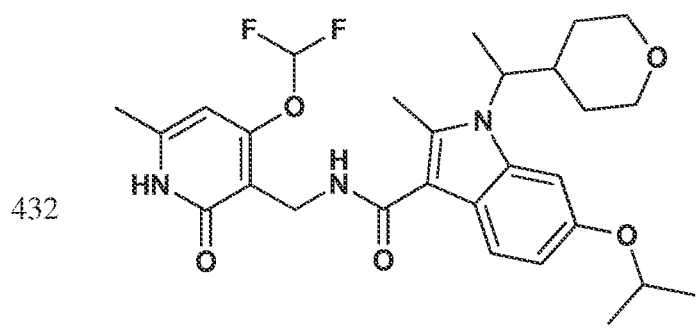
Figure 1:
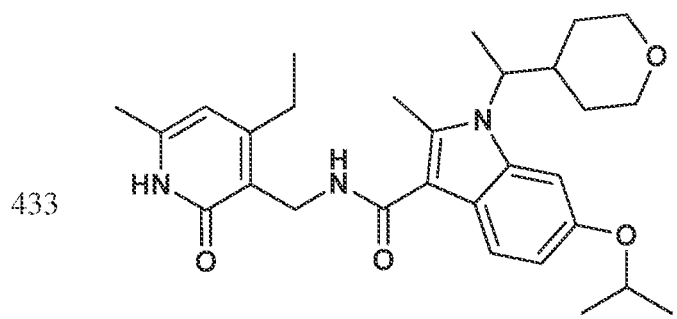
Figure 1:
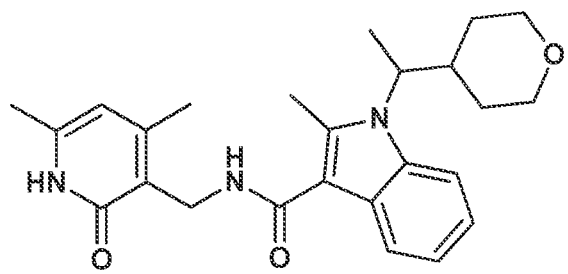
Figure 1:
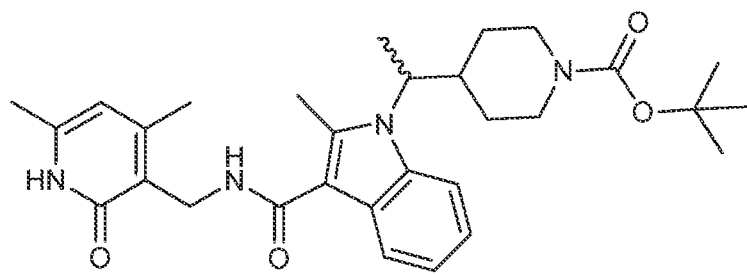
Figure 1:
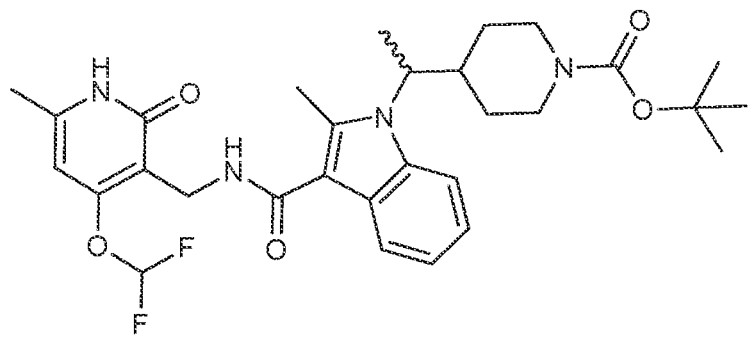
Figure 1:
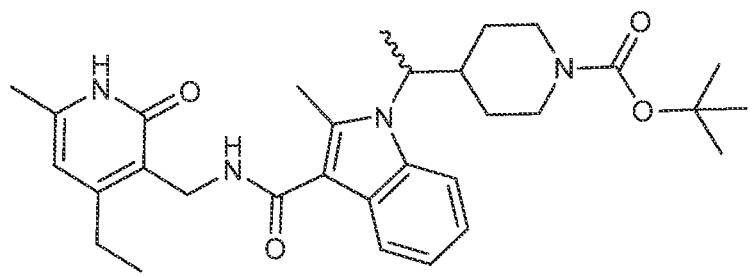
Figure 1:
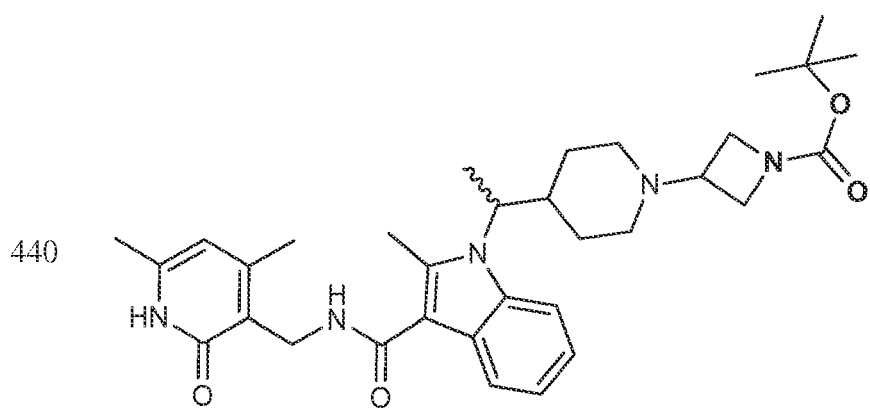
Figure 1:
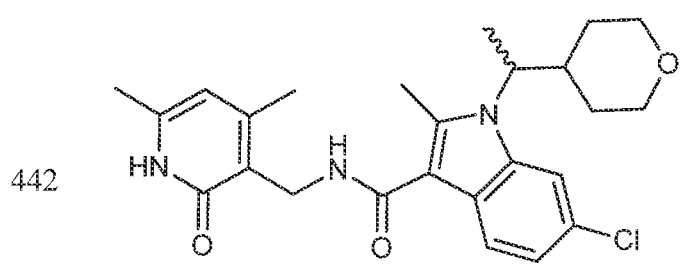

1. General Description of Compounds of the Invention

In certain embodiments, the present invention provides a compound of Formula II:

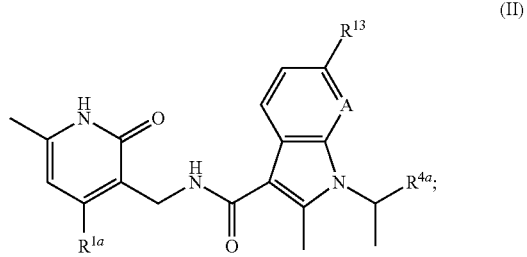

or a pharmaceutically acceptable salt thereof, wherein:
A is CH or N;
$R^{1a}$ is selected from $-C_1$-$C_2$ alkyl and $-O-(C_1$-$C_2$ alkyl), wherein $R^{1a}$ is optionally substituted with one or more fluoro;
$R^{4a}$ is selected from $-(C_1$-$C_4$ alkylene)-O-$(C_1$-$C_3$ alkyl), 1-substituted-piperidin-4-yl, $C_3$-$C_6$ cycloalkyl optionally substituted with one or more fluoro, and tetrahydropyranyl; and
$R^{13}$ is selected from hydrogen, halo, phenyl, pyridinyl, and $-O-(C_1$-$C_4$ alkyl).

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

A wavy bond ( ~~~ ) at a chiral center in a chemical structure is used to denote compounds of the invention that are optically pure, but whose optical rotation has not been determined. A straight bond at a chiral center indicates a racemic mixture although, as stated above, the invention also includes all possible isomeric forms of the racemate.

The terms "halo" and "halogen" as used herein refer to an atom selected from fluorine (fluoro, —F), chlorine (chloro, —Cl), bromine (bromo, —Br), and iodine (iodo, —I).

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—; —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; —$SiR^\circ_3$; —$(C_{1-4}$ straight or branched)alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R*, -(halo R*), —OH, —OR*, —O(halo R*), —CN, —C(O)OH, —C(O)O R*, —NH$_2$, —NHR*, —NR*$_2$, or —NO$_2$, wherein each R* is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits a target S-adenosylmethionine (SAM) utilizing enzyme with measurable affinity. In certain embodiments, an inhibitor has an IC$_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in activity of at least one SAM utilizing enzyme between a sample comprising a provided compound, or composition thereof, and at least one SAM dependent enzyme, and an equivalent sample comprising at least one SAM dependent enzyme, in the absence of said compound, or composition thereof.

3. Description of Exemplary Compounds

In some embodiments of Formula II, $R^{1a}$ is selected from —OCH$_3$, —CH$_3$, —OCHF$_2$, and —CH$_2$CH$_3$.

In some embodiments of Formula II, $R^{4a}$ is selected from —CH$_2$OCH$_3$, —CH(CH$_3$)OCH$_3$, 4,4-difluorocyclohexyl, cyclopropyl, tetrayhyrdopyran-4-yl, 1-(t-butoxycarbonyl)-piperidin-4-yl, 1-(isobutoxycarbonyl)-piperidin-4-yl, 1-(isopropoxycarbonyl)-piperidin-4-yl, 1-(2-fluoroethyl)-piperidin-4-yl, 1-(2,2-difluoroethyl)-piperidin-4-yl, 1-(2,2,2-trifluoroethyl)-piperidin-4-yl, 1-(2-hydroxyisobutyl)-piperidin-4-yl, 1-(hydroxyisopropylcarbonyl)-piperidin-4-yl, 1-(ethoxycarbonylmethyl)-piperidin-4-yl, 1-(isopropylcarbonyl)-piperidin-4-yl, 1-methylpiperidin-4-yl, 1-(methylsulfonyl)-piperidin-4-yl, 1-(ethylsulfonyl)-piperidin-4-yl, 1-(isopropylsulfonyl)-piperidin-4-yl, 1-(phenyl)-piperidin-4-yl, 1-(oxetan-3-yl)piperidin-4-yl, 1-(pyridin-2-yl)-piperidin-4-yl, and 1-(pyrimidin-2-yl)-piperidin-4-yl.

In some embodiments of Formula II, $R^{13}$ is selected from hydrogen, chloro, fluoro, —OCH(CH$_3$)$_2$, phenyl, and pyridin-2-yl.

Exemplary compounds of Formula II are set forth in FIG. 1. In some cases two (or more) of the compounds in FIG. 1 having one (or more) wavy bonds will have the exact same structure. Because the wavy bond represents a chiral center of undetermined optical rotation, such compounds will be understood to be separate and distinct optical isomers of one another. FIG. 1 is annotated to indicate those sets of two or more compounds that have the same depicted structure, but are of different stereochemistry.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate a histone methyl modifying enzyme, or a mutant thereof, in a biological sample or in a patient. In certain embodiments, the amount of compound in compositions of this invention is such that is effective to measurably modulate a histone methyl modifying enzyme, or a mutant thereof, in a biological sample or in a patient.

In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulating of activity of one or more enzymes involved in epigenetic regulation.

Epigenetics is the study of heritable changes in gene expression caused by mechanisms other than changes in the underlying DNA sequence. Molecular mechanisms that play a role in epigenetic regulation include DNA methylation and chromatin/histone modifications. Histone methylation, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation, sumoylation, ubiquitination, citrullination, deimination, and biotinylation. The core of histones H2A and H3 can also be modified. Histone modifications are integral to diverse biological processes such as gene regulation, DNA repair, and chromosome condensation.

The present disclosure provides compounds and compositions for modulating activity of histone methyl modifying enzymes. Histone methyl modifying enzymes are key regulators of cellular and developmental processes. Histone methyl modifying enzymes may be characterized as either histone methyl transferases or histone demethylases. Histone demethylase enzymes have modules that mediate binding to methylated residues. For example, multiple demethylases contain a Tudor domain (e.g., JMJD2C/GASC1) or a PHD domain (e.g., JARID1C/SMCX, PHF8).

The lysine specificities of many histone methyltransferases have been characterized. For example SET7/9, SMYD3, and MLL1-5 are specific for H3K4. SUV39H1, DIM-5, and G9a are specific for H3K9. SET8 is specific for H4K20.

DOT1 is an example of a non-SET domain containing histone methylase. DOT1 methylates H3 on lysine 79.

Just as histone methylases have been shown to regulate transcriptional activity, chromatin structure, and gene silencing, demethylases have also been discovered which impact gene expression. LSD1 was the first histone lysine demethylase to be characterized. This enzyme displays homology to FAD-dependent amine oxidases and acts as a transcriptional corepressor of neuronal genes (Shi et al., Cell 119:941-953, 2004). Additional demethylases defining separate demethylase families have been discovered, including JHDM1 (or KDM2), JHDM2 (or KDM3), JMJD2 (or KDM4), JARID (or KDM5), JMJD3 (or KDM6), and JMJD6 families (Lan et al., Curr. Opin. Cell Biol. 20(3):316-325, 2008).

Demethylases act on specific lysine residues within substrate sequences and discriminate between the degree of methylation present on a given residue. For example, LSD1 removes mono- or dimethyl-groups from H3K4. Members of the JARID1A-D family remove trimethyl groups from H3K4. UTX and JMJD3 demethylate H3K27, counteracting effects of EZH2 methylase activity. Substrate specificities of other demethylases have been characterized (see Shi, Nat. Rev. 8:829-833, 2007).

One class of histone methylases is characterized by the presence of a SET domain, named after proteins that share the domain, Su(var)3-9, enhancer of zeste [E(Z)], and trithorax. A SET domain includes about 130 amino acids. SET domain-containing methylase families include SUV39H1, SET1, SET2, EZH2, RIZ1, SMYD3, SUV4-20H1, SET7/9, and PR-SET7/SET8 families (reviewed in Dillon et al., Genome Biol. 6:227, 2005). Members of a family typically include similar sequence motifs in the vicinity of and within the SET domain. The human genome encodes over 50 SET domain-containing histone protein methylases, any of which can be used in an assay described herein.

EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to tri-methylate histone H3 at lysine 27 (Cao and Zhang, Mol. Cell 15:57-67, 2004). PRC2 complexes can also include RBAP46 and RBAP48 subunits.

The oncogenic activities of EZH2 have been shown by a number of studies. In cell line experiments, over-expression of EZH2 induces cell invasion, growth in soft agar, and motility while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor supressors, including E-cadherin, DAB2IP and RUNX3 among others. In xenograft models, EZH2 knockdown inhibits tumor growth and metastasis. Recently, it has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

In some embodiments, compounds of the present invention modulate the activity of one or more enzymes involved in epigenetic regulation. In some embodiments, compounds of the present invention modulate the activity of a histone methyl modifying enzyme, or a mutant thereof. In some embodiments, compounds of the present invention modulate EZH2 activity. In some embodiments, compounds of the present invention down-regulate or suppress the activity of EZH2. In some embodiments, compounds of the present invention are antagonists of EZH2 activity.

In some embodiments, compounds and compositions of the present invention are useful in treating diseases and/or disorders associated with a histone methyl modifying enzyme. Accordingly, in some embodiments, the present invention provides a method of modulating a disease and/or disorder associated with a histone methyl modifying enzyme. In some embodiments, the present invention provides a method of treating a subject suffering from a disease and/or disorder associated with a histone methyl modifying enzyme comprising the step of administering a compound or composition of Formula II.

In some embodiments, compounds and compositions of the present invention are useful in treating diseases and/or disorders associated with overexpression of EZH2. In some embodiments, the present invention provides a method of treating a subject suffering from a disease and/or disorder associated with overexpression of EZH2 comprising the step of administering a compound or composition of Formula II. In some embodiments, the above method additionally comprises the preliminary step of determining if the subject is overexpressing EZH2.

In some embodiments, compounds and compositions of the present invention are useful in treating diseases and/or disorders associated with cellular proliferation. In some embodiments, compounds and compositions of the present invention are useful in treating diseases and/or disorders associated with misregulation of cell cycle or DNA repair. In some embodiments, compounds and compositions of the present invention are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 August; 42(8):665-7). Accordingly, in some embodiments, compounds and compositions of the present invention are useful in treating diseases and/or disorders associated with the presence of a mutant form of EZH2. In some embodiments, compounds and compositions of the present invention are useful in treating diseases and/or disorders associated with the presence of Y641N EZH2. In some embodiment, the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions of the present invention are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Proceedings of the National Academy of Sciences, PNAS Early Edition published ahead of print on Nov. 15, 2010.

In some embodiments, the present invention provides a method of reducing the activity of EZH2 in a subject comprising the step of administering a compound or composition of Formula II. In some embodiments, the present invention provides a method of reducing the activity of wide-type EZH2 in a subject comprising the step of administering a compound or composition of Formula II. In some embodiments, the present invention provides a method of reducing the activity of a mutant form of EZH2 in a subject comprising the step of administering a compound or composition of Formula II. In some embodiments, the present invention provides a method of reducing the activity of a mutant form of EZH2 in a subject comprising the step of administering a compound or composition of Formula II, wherein the mutant form of EZH2 is Y641N EZH2. In some embodiments, the present invention provides a method of treating a subject suffering from a disease and/or disorder associated with EZH2 comprising the step of administering a compound or composition of Formula II. In some embodiments, the present invention provides a method of treating a subject suffering from a disease and/or disorder associated with wide-type EZH2 comprising the step of administering a compound or composition of Formula II. In some embodiments, the present invention provides a method of treating a subject suffering from a disease and/or disorder associated with a mutant form of EZH2 comprising the step of administering a compound or composition of Formula II. In some embodiments, the present invention provides a method of treating a subject suffering from a disease and/or disorder associated with a mutant form of EZH2 comprising the step of administering a compound or composition of Formula II, wherein the mutant form of EZH2 is Y641N EZH2. In some embodiments, the above method additionally comprises the preliminary step of determining if the subject is expressing a mutant form of EZH2, such as Y641N EZH2 In some embodiments, the present invention provides a method of reducing the activity of a mutant form of EZH2, such as Y641N EZH2, in a subject in need thereof comprising the step of administering a compound or composition of Formula II. In some embodiments, the present invention provides a method of treating a subject suffering from a disease and/or disorder associated with a mutant form of EZH2 comprising the step of administering a compound or composition of Formula II. In some embodiments, the above method additionally comprises the preliminary step of determining if the subject is expressing a mutant form of EZH2, such as Y641N EZH2. In some embodiments, that determination is made by determining if the subject has increased levels of histone H3 Lys-27-specific trimethylation (H3K27me3), as compared to a subject known not to express a mutant form of EZH2.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

It will be appreciated that for compound preparations described herein, when reverse phase HPLC is used to purify a compound, a compound may exist as an acid addition salt. In some embodiments, a compound may exist as a formic acid or mono-, di-, or tri-trifluoroacetic acid salt.

It will further be appreciated that the present invention contemplates individual compounds described herein. Where individual compounds exemplified are isolated and/or characterized as a salt, for example, as a trifluoroacetic acid salt, the present invention contemplates a free base of the salt, as well as other pharmaceutically acceptable salts of the free base.

The following examples contain important additional information, exemplification and guidance that can be adapted to the practice of this invention in its various embodiments and the equivalents thereof.

Procedures for preparing the compounds exemplified below, as well as additional compounds/intermediates in the synthetic schemes can be found in International Application No. PCT/US2013/025639, the contents of which are incorporated herein by reference.

EXAMPLES

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Unless otherwise noted, all solvents, chemicals, and reagents were obtained commercially and used without purification. The $^1$H NMR spectra were obtained in CDCl$_3$, d$_6$-DMSO, CD$_3$OD, or d$_6$-acetone at 25° C. at 300 MHz on an OXFORD (Varian) with chemical shift ($\delta$, ppm) reported relative to TMS as an internal standard. HPLC-MS chromatograms and spectra were obtained with Shimadzu LC-MS-2020 system. Chiral analysis and purification were obtained with Yilite P270.

Example 1

Synthesis of Compounds 327 and 346 and Related Compounds and Intermediates

The title compounds of this Example and other related compounds were prepared according to the following general scheme. In addition, where indicated, modifications of this scheme are disclosed for the synthesis of still additional related compounds of the invention and intermediates thereof.

13
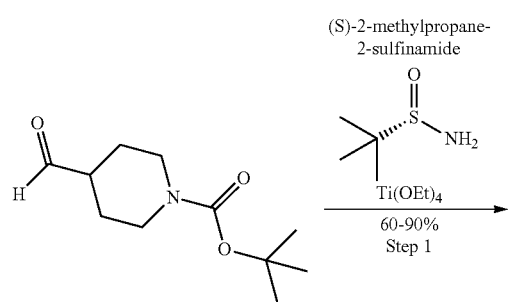
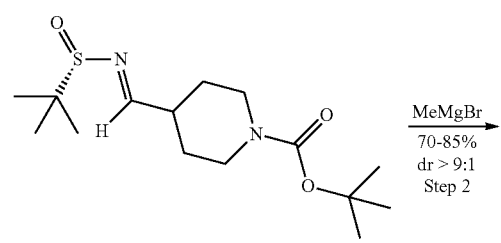
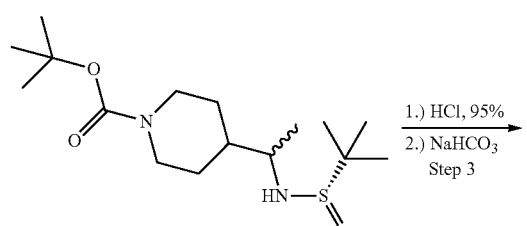
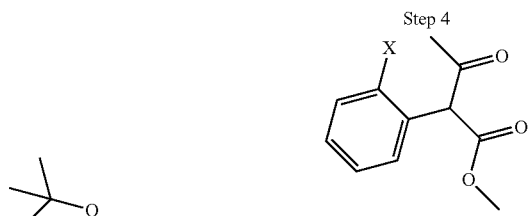
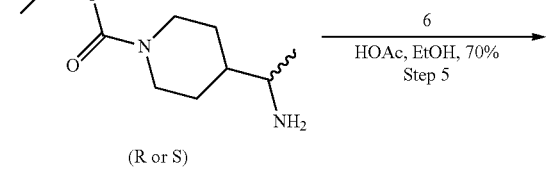
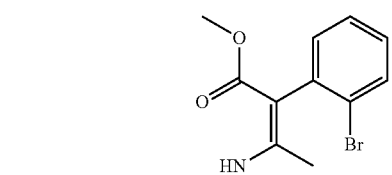
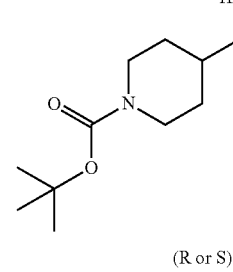
14
-continued
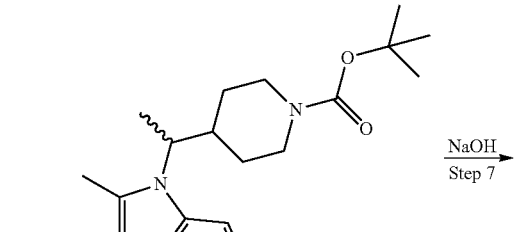
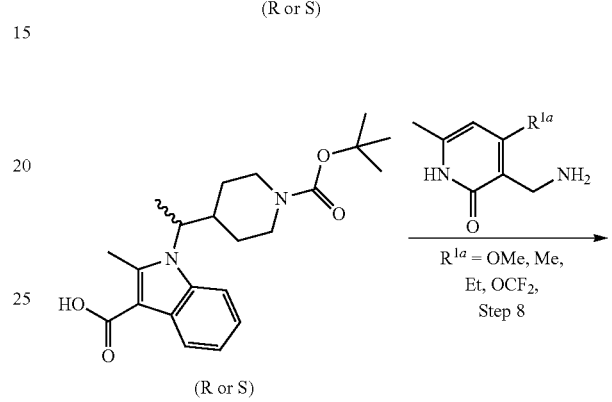
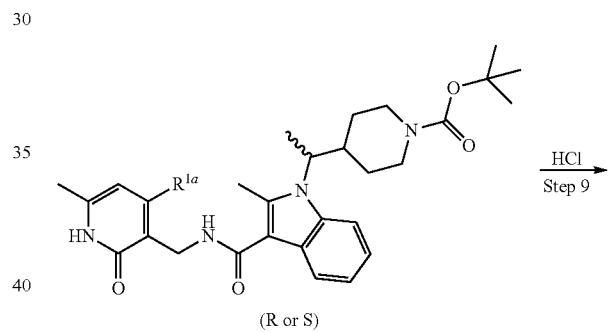
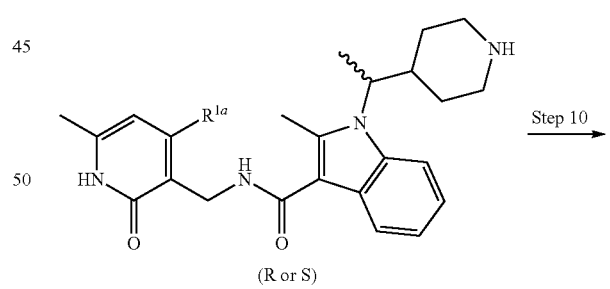
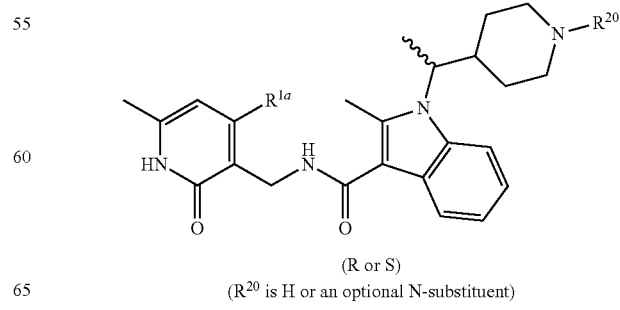

Step 1: (S,E)-tert-butyl 4-(((tert-butylsulfinyl)imino)methyl)piperidine-1-carboxylate

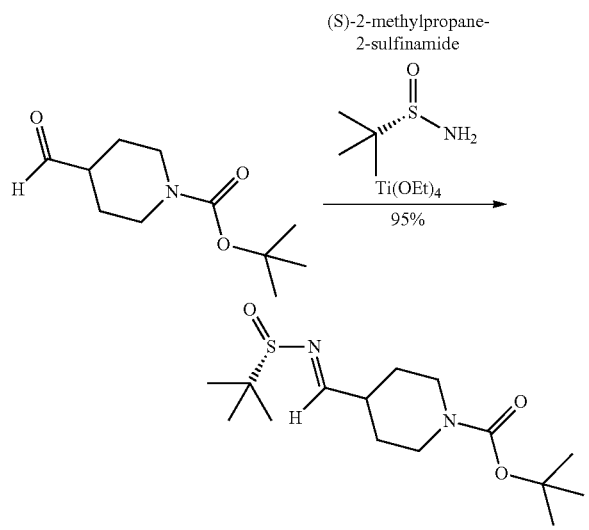

To a round bottomed flask charged with a magnetic stir bar was added (S)-2-methylpropane-2-sulfinamide (20.46 g, 169 mmol), tert-butyl 4-formylpiperidine-1-carboxylate (30 g, 141 mmol), DCM (300 mL), and Ti(OEt)₄ (59.0 ml, 281 mmol). The solution was stirred at room temperature for 3 h before it was quenched with brine (80 mL). The solution was stirred for 30 minutes before filtering. The filter cake was washed with DCM and the filtrate was placed in a separatory funnel and washed with water. The organics layer was dried over Na₂SO₄, filtered, and concentrated in vacuo. The crude residue solidified to the title compound (29 g, 92 mmol, 65.1% yield) m/z 217.

The intermediate shown in the following table was prepared according to the general procedure outlined in Step 1 using the appropriate starting materials and modifications.

| Name | Structure | m/z |
|---|---|---|
| (S,E)-2-methyl-N-((tetrahydro-2H-pyran-4-yl)methylene)propane-2-sulfinamide | 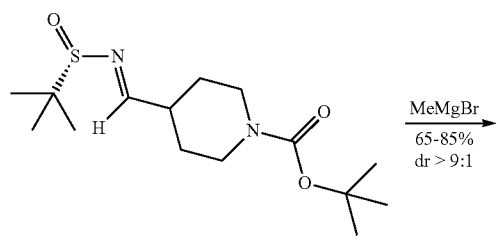 | |

Step 2: Tert-butyl 4-((S)-1-((R or S)-1,1-dimethylethylsulfinamido)ethyl) piperidine-1-carboxylate

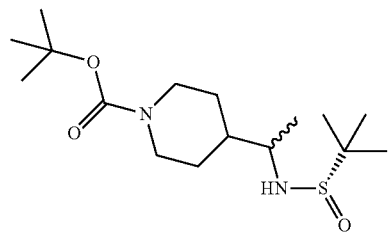

To a round bottomed flask charged with a magnetic stir bar was added (S,E)-tert-butyl 4-((tert-butylsulfinylimino)methyl)piperidine-1-carboxylate (36.4 g, 115 mmol), DCM (400 mL), and the solution was cooled to 0° C. in an ice bath with stirring. To this solution was added MeMgBr (77 ml, 230 mmol) (3M in diethyl ether) and the reaction stirred for 4 h while warming to room temperature. The reaction was carefully quenched via the addition of saturated aqueous NH₄Cl. The solid were broken up by the addition of 1N HCl. The layers were separated and the aqueous phase was extracted with DCM. The combined organics phase was dried over Na₂SO₄, filtered, and concentrated in vacuo to afford the title compound (29 g, >9:1 dr) which is used without further purification in the next step.

The intermediate shown in the following table was prepared according to the general procedure outlined in Step 2 using the appropriate starting materials and modifications.

| Name | Structure | m/z |
|---|---|---|
| (S)-2-methyl-N-((R or S)-1-(tetrahydro-2H-pyran-4-yl)ethyl)propane-2-sulfinamide | 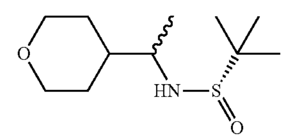 | 234 |

Step 3: (R or S)-tert-butyl 4-(1-aminoethyl)piperidine-1-carboxylate

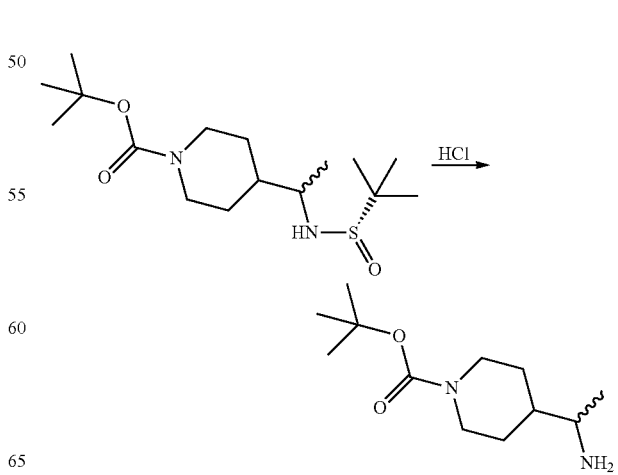

To a 1 L round bottomed flask charged with a magnetic stir bar was added crude tert-butyl 4-((S)-1-((S)-1,1-dimethylethylsulfinamido)ethyl)piperidine-1-carboxylate (29 g) was taken up in MeOH (200 mL) before addition of a 4 N solution of HCl in 1,4-dioxane (24.06 ml, 96 mmol). The resulting solution was then stirred at room temperature for 1 h at rt. The methanol was then removed in vacuo to afford viscous oil which was treated with sat'd aqueous NaHCO$_3$ (~500 mL) and extracted with ethyl acetate (2×500 mL). This organic phase was combined, dried with MgSO$_4$, filtered, and solvent was then removed in vacuo affording the title compound (22 g) which was used without further purification.

The intermediate shown in the following table was prepared according to the general procedure outlined in Step 3 using the appropriate starting materials.

| Name | Structure | m/z |
|---|---|---|
| (R or S)-1-(tetrahydro-2H-pyran-4-yl)ethanamine | 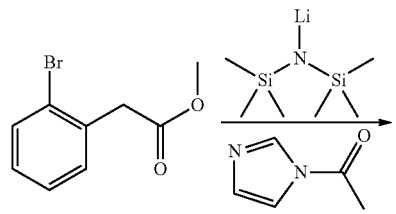 | 130 |

Step 4: Methyl 2-(2-bromophenyl)-3-oxobutanoate

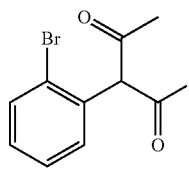

A round bottomed flask was charged with a magnetic stir bar and methyl 2-(2-bromophenyl)acetate (25 g, 109 mmol) and THF (50 mL). This solution was cooled to −78° C. before drop wise addition of a 1M solution of LiHMDS in THF (218 ml, 218 mmol). The reaction was stirred for 30 min at −78° C. before addition of 1-(1H-imidazol-1-yl)ethanone (14.42 g, 131 mmol) dissolved in a mixture of THF:DMF (112 mL THF, 24 mL DMF). The solution was stirred for 1 h before quenching with sat'd aqueous NH$_4$Cl (~250 mL) and diluting with EtOAc. The layers were separated and the aqueous phase was extracted with EtOAc (~2×250 mL). The combined organic extract was washed with brine, dried over Na$_2$SO$_4$, filtered, and concentrated in vacuo. The crude residue was purified via silica gel chromatography using an eluent of ethyl acetate/hexanes (10:1) to afford methyl 2-(2-bromophenyl)-3-oxobutanoate (32.5 g, 102 mmol, 93% yield).

The intermediates shown in the following table were prepared according to the general procedure outlined in Step 4 using the appropriate starting materials.

| Name | Structure | m/z |
|---|---|---|
| methyl 2-(2-bromo-4-chlorophenyl)-3-oxobutanoate | 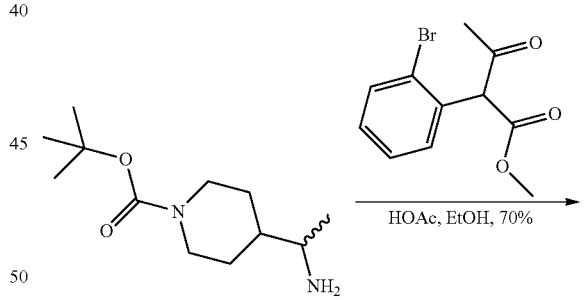 | 304 |
| methyl 2-(2-bromo-4-methoxyphenyl)-3-oxobutanoate | 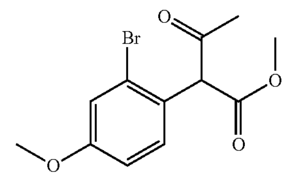 | 302 |
| methyl 2-(2-bromo-4-fluorophenyl)-3-oxobutanoate | 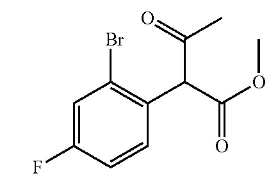 | 289 |

Step 5: (R or S, E and Z)-tert-butyl 4-(1-(3-(2-bromophenyl)-4-methoxy-4-oxobut-2-en-2-ylamino)ethyl)piperidine-1-carboxylate

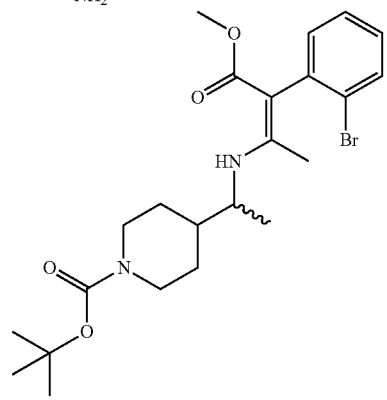

To a round bottomed flask was added (R or S)-tert-butyl 4-(1-aminoethyl)piperidine-1-carboxylate (9.35 g, 40.9 mmol), EtOH (75 mL), and methyl 2-(2-bromophenyl)-3-oxobutanoate (7.40 g, 27.3 mmol) (from Step 4). To this solution was added AcOH (1.563 ml, 27.3 mmol) and the reaction was heated overnight at 85° C. before cooling to room temperature and concentrating. The crude residue was purified via silica gel chromatography (330 g, 100% hexanes to 25% EA in hexanes) to afford the title compound (6.45 g, 13.40 mmol, 49.1% yield).

The intermediates shown in the following table were prepared according to the general procedure outlined in Step 5 using the appropriate starting materials.

| Name | Structure | m/z |
|---|---|---|
| (R or S,Z)-methyl 2-(2-bromophenyl)-3-((1-(tetrahydro-2H-pyran-4-yl)ethyl)amino)but-2-enoate | 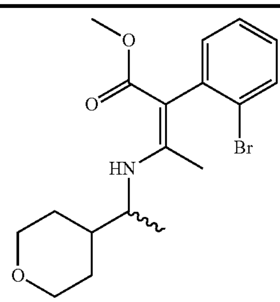 | 383 |
| (R or S,Z)-methyl 2-(2-bromo-4-chlorophenyl)-3-((1-(tetrahydro-2H-pyran-4-yl)ethyl)amino)but-2-enoate | | 417 |
| (R or S,Z)-methyl 2-(2-bromo-4-chlorophenyl)-3-((1-(tetrahydro-2H-pyran-4-yl)ethyl)amino)but-2-enoate | | 417 |
| (R or S,Z)-methyl 2-(2-bromo-4-fluorophenyl)-3-((1-(tetrahydro-2H-pyran-4-yl)ethyl)amino)but-2-enoate | | 401 |

Step 6: (R or S)-methyl 1-(1-(1-(tert-butoxycarbonyl)piperidin-4-yl)ethyl)-2-methyl-1H-indole-3-carboxylate

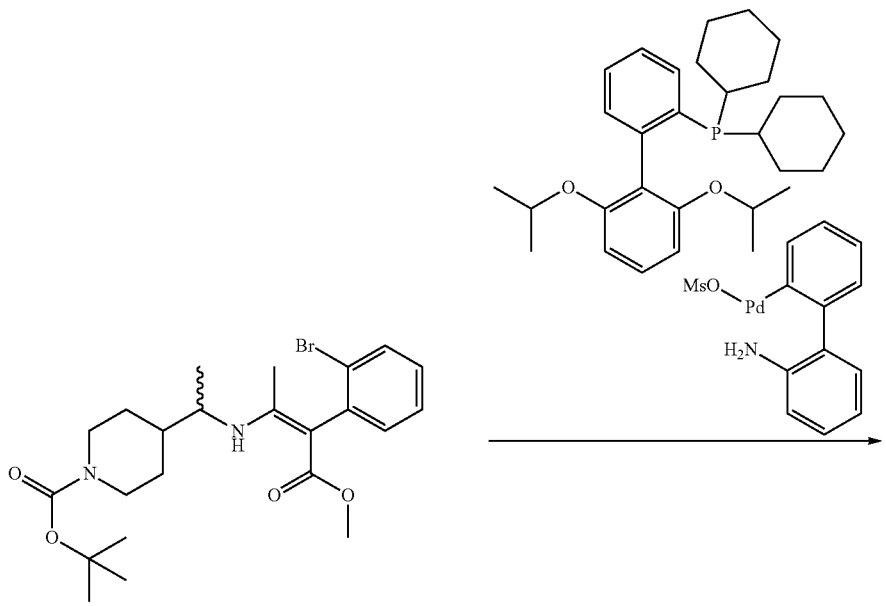

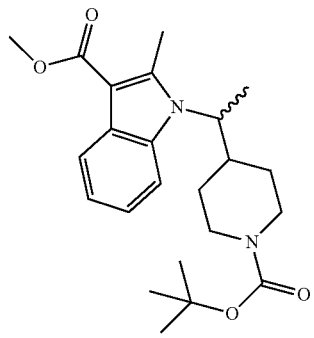

A 250 mL round bottom flask was charged with a magnetic stir bar, (R or S,Z)-tert-butyl 4-(1-(3-(2-bromophenyl)-4-methoxy-4-oxobut-2-en-2-ylamino)ethyl)piperidine-1-carboxylate (3.33 g, 6.92 mmol), RuPhos Pre-catalyst II (Methanesulfonato(2-dicyclohexylphosphino-2',6'-di-i-propoxy-1,1'-biphenyl)(2-amino-1,1'-biphenyl-2-yl) palladium(II)) (0.463 g, 0.553 mmol), dicyclohexyl(2',6'-diisopropoxybiphenyl-2-yl)phosphine (0.387 g, 0.830 mmol), anhydrous 1,4-dioxane (27.7 ml, 6.92 mmol), and sodium methoxide (0.561 g, 10.38 mmol). The reaction mixture was purged and back-filled with nitrogen and heated to 100° C. with stirring overnight before being allowed to cool to rt. The reaction was diluted with ethyl acetate (~100 ml) and the mixture was filtered through a bed of diatomaceous earth. The filtrate was pre-absorbed onto silica gel (~30 g) and purified via silica gel chromatography (120 g) using ethyl acetate/hexanes (1:1) as eluent to afford the title compound (2.01 g, 4.77 mmol, 68.9% yield).

The intermediates shown in the following table were prepared according to the general procedure outlined in Step 6 using the appropriate starting materials.

| Name | Structure | m/z |
|---|---|---|
| (R or S)-methyl 2-methyl-1-(1-(tetrahydro-2H-pyran-4-yl)ethyl)-1H-indole-3-carboxylate | 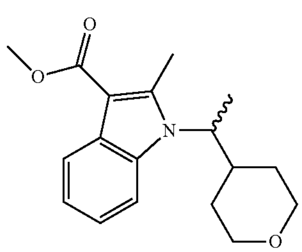 [SMILES: COC(=O)c1c(C)n(C(C)C2CCOCC2)c2ccccc12] | 302 |
| (R or S)-methyl 6-chloro-2-methyl-1-(1-(tetrahydro-2H-pyran-4-yl)ethyl)-1H-indole-3-carboxylate | 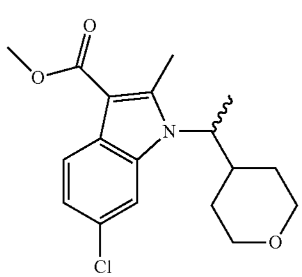 [SMILES: COC(=O)c1c(C)n(C(C)C2CCOCC2)c2cc(Cl)ccc12] | 337 |
| (R or S)-methyl 6-methoxy-2-methyl-1-(1-(tetrahydro-2H-pyran-4-yl)ethyl)-1H-indole-3-carboxylate | | 332 |
| (R or S)-methyl 6-fluoro-2-methyl-1-(1-(tetrahydro-2H-pyran-4-yl)ethyl)-1H-indole-3-carboxylate | | 320 |

Step 7: (R or S)-2-methyl-1-(1-(tetrahydro-2H-pyran-4-yl)ethyl)-1H-indole-3-carboxylic acid

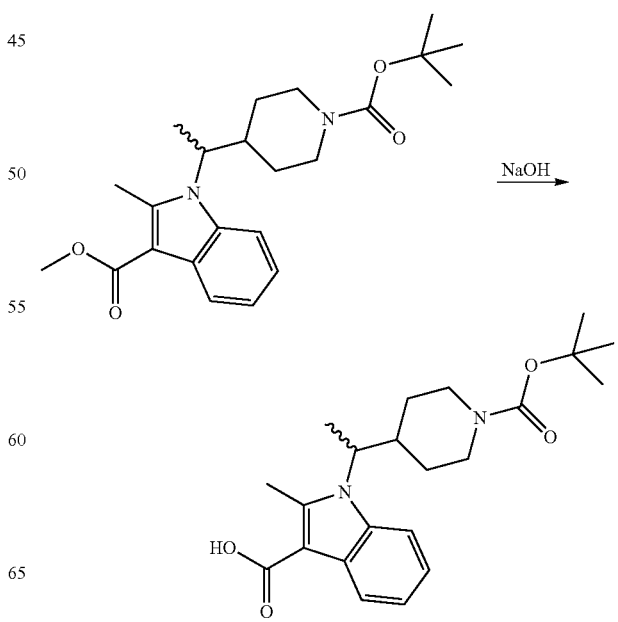

A 1 L round bottom flask was charged with a magnetic stir bar, (R or S)-methyl 2-methyl-1-(1-(tetrahydro-2H-pyran-4-yl)ethyl)-1H-indole-3-carboxylate (11.60 g, 38.5 mmol), ethanol (96 ml, 38.5 mmol), and 6 N aqueous NaOH (64.1 ml, 385 mmol). The flask was fitted with a reflux condenser and heated to reflux for 6 h before being allowed to cool to rt. The volatiles were removed in vacuo and the resulting mixture was poured into 10% HCl (~300 mL). A precipitate formed which was collected via vacuum filtration using a Buchner funnel. The filter cake was rinsed with an additional portion of water (~200 mL), collected, and dried under vacuum to afford the title compound (10.87 g, 35.9 mmol, 93% yield) as an off-white solid.

The intermediates shown in the following table were prepared according to the general procedure outlined in Step 7 using the appropriate starting materials.

| Name | Structure | m/z |
| --- | --- | --- |
| (R or S)-2-methyl-1-(1-(tetrahydro-2H-pyran-4-yl)ethyl)-1H-indole-3-carboxylic acid | | 287 |
| (R or S)-6-chloro-2-methyl-1-(1-(tetrahydro-2H-pyran-4-yl)ethyl)-1H-indole-3-carboxylic acid | | 321 |
| (R or S)-6-methoxy-2-methyl-1-(1-(tetrahydro-2H-pyran-4-yl)ethyl)-1H-indole-3-carboxylic acid | 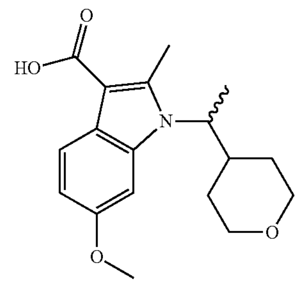 [SMILES: COc1ccc2c(C(=O)O)c(C)n(C(C)C3CCOCC3)c2c1] | 317 |
| (R or S)-6-fluoro-2-methyl-1-(1-(tetrahydro-2H-pyran-4-yl)ethyl)-1H-indole-3-carboxylic acid | 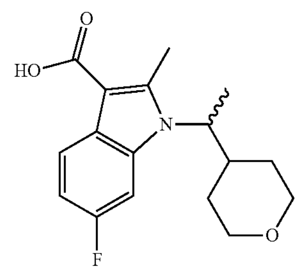 [SMILES: Cc1c(C(=O)O)c2ccc(F)cc2n1C(C)C1CCOCC1] | 306 |
| (R or S)-2-methyl-6-(pyridin-3-yl)-1-(1-(tetrahydro-2H-pyran-4-yl)ethyl)-1H-indole-3-carboxylic acid | 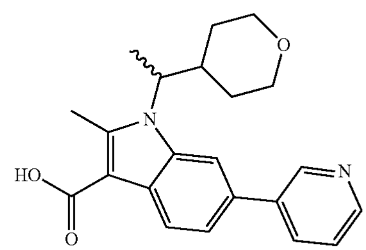 [SMILES: Cc1c(C(=O)O)c2ccc(-c3cccnc3)cc2n1C(C)C1CCOCC1] | 365 |

Step 8: (R or S)-tert-butyl 4-(1-(3-((4-methoxy-6-methyl-2-oxo-1,2-dihydropyridin-3-yl)methylcarbamoyl)-2-methyl-1H-indol-1-yl)ethyl)piperidine-1-carboxylate (Compound 327)

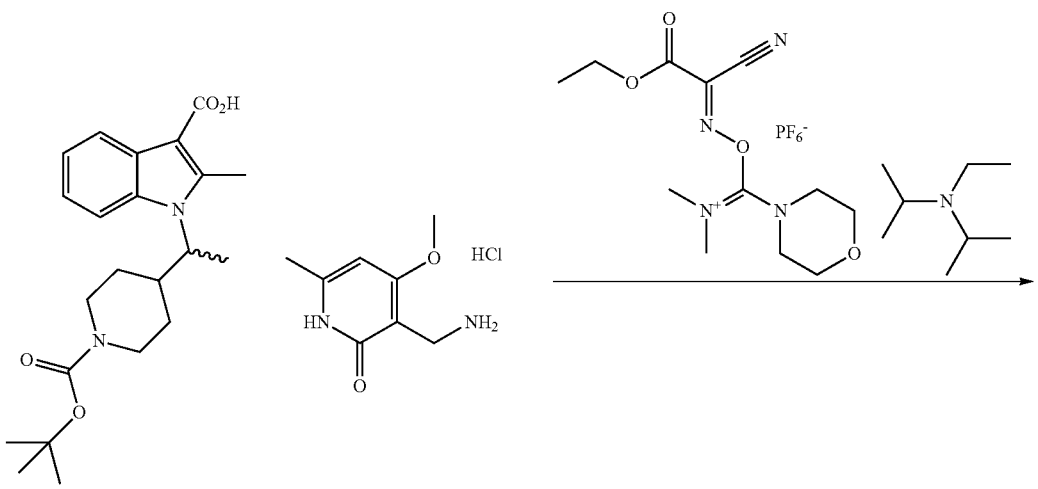

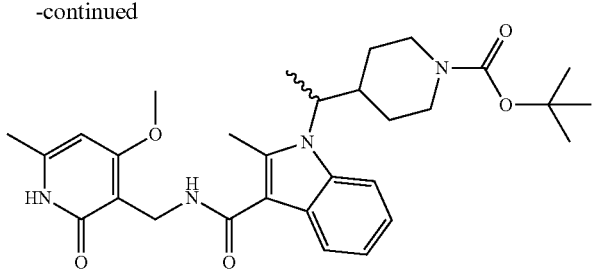

A 250 mL round bottom flask was charged with a magnetic stir bar, (R or S)-1-(1-(1-(tert-butoxycarbonyl)piperidin-4-yl)ethyl)-2-methyl-1H-indole-3-carboxylic acid (1.950 g, 5.05 mmol), 3-(aminomethyl)-4-methoxy-6-methylpyridin-2(1H)-one hydrochloride (2.065 g, 10.09 mmol), DMF (25.2 ml, 5.05 mmol), Hunig's base (3.52 ml, 20.18 mmol). The reaction mixture was cooled to 0° C. and COMU (2.16 g, 5.05 mmol) was added. The reaction was allowed to stir overnight to room temperature. The reaction mixture was diluted with water and extracted with EtOAc. The combined organic extract was washed with brine, dried with MgSO$_4$, filtered and conc. in vacuo to afford the crude material which was purified via silica gel chromatography (120 g) using MeOH/ethyl acetate (1:5) as eluent to afford the title compound (1.86 g, 3.29 mmol, 65.3% yield). LCMS 537 (M+1)[+1] $^1$H NMR (400 MHz, DMSO-d$_6$) δ=11.83-11.71 (m, 1H), 7.80 (br. s., 1H), 7.73 (d, J=7.6 Hz, 1H), 7.62 (d, J=7.8 Hz, 1H), 7.06 (td, J=7.1, 14.4 Hz, 2H), 6.21 (s, 1H), 4.32 (br. s., 2H), 4.16 (br. s., 1H), 4.02 (br. s., 1H), 3.85 (s, 3H), 3.75 (br. s., 1H), 2.70 (br. s., 1H), 2.58 (s, 3H), 2.37 (br. s., 1H), 2.21 (s, 3H), 1.90 (d, J=12.9 Hz, 1H), 1.53 (d, J=6.9 Hz, 3H), 1.35 (s, 10H), 1.21 (br. s., 1H), 0.89 (d, J=8.7 Hz, 1H), 0.67 (d, J=11.8 Hz, 1H).

The compounds shown in the following table were prepared according to the general procedure outlined in Step 8 using the appropriate starting materials. The structures of the compounds are shown in FIG. 1.

| Compound Number | Name | $^1$H NMR | m/z |
|---|---|---|---|
| 435 | (R or S)-tert-butyl 4-(1-(3-(((4,6-dimethyl-2-oxo-1,2-dihydropyridin-3-yl)methyl)carbamoyl)-2-methyl-1H-indol-1-yl)ethyl)piperidine-1-carboxylate | | 521 |
| 436 | (R or S)-tert-butyl 4-(1-(3-(((4-(difluoromethoxy)-6-methyl-2-oxo-1,2-dihydropyridin-3-yl)methyl)carbamoyl)-2-methyl-1H-indol-1-yl)ethyl)piperidine-1-carboxylate | | 573 |
| 437 | (R or S)-tert-butyl 4-(1-(3-(((4-ethyl-6-methyl-2-oxo-1,2-dihydropyridin-3-yl)methyl)carbamoyl)-2-methyl-1H-indol-1-yl)ethyl)piperidine-1-carboxylate | | 535 |
| 298 | (R or S)-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-d$_6$) δ 11.60 (s, 1H), 7.73-7.62 (m, 3H), 7.60 (d, 2H) 7.07-7.05 (m, 2H), 6.15 (s, 1H) 4.33 (s, 1H), 4.21-4.11 (m, 1H), 3.92 (br. d., 1H), 3.65 (d, 1H), 3.34-3.32 (m, 1H), 3.02 (t, 1H), 2.61 (s, 3H), 2.48-2.44 (m, 1H), 2.20 (s, 3H), 1.84-1.81 (m, 1H), 1.54 (d, 3H), 1.40-1.38 (m, 12H), 1.25-1.22 (m, 1H), 1.08-1.04 (m, 1H), 0.86 (br. s., 1H), 0.58 (br. d., 1H) | 438 |
| 300 | (R or S)-6-fluoro-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-d$_6$) δ = 11.57 (br. s., 1 H), 7.75-7.67 (m, 2 H), 7.48 (d, J = 10.7 Hz, 1 H), 6.90 (t, J = 8.5 Hz, 1 H), 6.13 (s, 1 H), 4.29 (d, J = 4.5 Hz, 2 H), 4.12 (br. s., 1 H), 3.94-3.87 (m, 1 H), 3.83 (s, 3 | 456 |

-continued

| Compound Number | Name | ¹H NMR | m/z |
|---|---|---|---|
| | | H), 3.64 (dd, J = 3.6, 10.9 Hz, 1 H), 3.35 (br. s., 1 H), 3.05 (br. s., 1 H), 2.56 (s, 3 H), 2.45-2.37 (m, 1 H), 2.18 (s, 3 H), 1.81 (d, J = 12.7 Hz, 1 H), 1.50 (d, J = 6.9 Hz, 3 H), 1.40-1.29 (m, 1 H), 1.11-0.99 (m, 1 H), 0.61 (br. s., 1 H) | |
| 314 | (R or S)-6-chloro-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-d₆) δ 11.57 (s, 1 H), 7.75 (s, 2 H), 7.66 (d, J = 8.9 Hz, 1 H), 7.08 (d, J = 8.5 Hz, 1 H), 6.14 (s, 1 H), 4.30 (d, J = 4.5 Hz, 2 H), 4.21-4.05 (m, 2 H), 3.91 (d, J = 11.4 Hz, 1 H), 3.85 (s, 3 H), 3.65 (d, J = 10.5 Hz, 1 H), 3.02 (t, J = 11.3 Hz, 1 H), 2.58 (s, 3 H), 2.46-2.31 (m, 1 H), 2.19 (s, 3 H), 1.82 (d, J = 12.0 Hz, 1 H), 1.59-1.45 (m, 4 H), 1.44-1.29 (m, 1 H), 0.57 (d, J = 12.9 Hz, 1 H) | 472 |
| 321 | (R or S)-6-methoxy-N-((4-methoxy-6-methyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-d₆) δ = 11.59 (s, 1 H), 7.67-7.59 (m, 2 H), 7.03 (s, 1 H), 6.75-6.68 (m, 1 H), 6.14 (s, 1 H), 4.30 (d, J = 5.1 Hz, 2 H), 4.10 (dd, J = 7.5, 10.4 Hz, 1 H), 3.91 (dd, J = 3.0, 11.3 Hz, 1 H), 3.83 (s, 3 H), 3.80-3.76 (m, 3 H), 3.68-3.60 (m, 1 H), 3.38-3.32 (m, 1 H), 3.10-3.00 (m, 1 H), 2.56 (s, 3 H), 2.19 (s, 3 H), 1.83 (d, J = 12.7 Hz, 1 H), 1.55-1.43 (m, 4 H), 1.34 (br. s., 1 H), 1.10-0.96 (m, 1 H), 0.62 (d, J = 13.4 Hz, 1 H) | 468 |
| 335 | (R or S)-N-((4-(difluoromethoxy)-6-methyl-2-oxo-1,2-dihydropyridin-3-yl)methyl)-2-methyl-1-(1-(tetrahydro-2H-pyran-4-yl)ethyl)-1H-indole-3-carboxamide | | 474 |
| 394 | (R or S)-N-((4,6-dimethyl-2-oxo-1,2-dihydropyridin-3-yl)methyl)-2-methyl-1-(1-(tetrahydro-2H-pyran-4-yl)ethyl)-1H-indole-3-carboxamide | | 422 |
| 442 | (R or S)-6-chloro-N-((4,6-dimethyl-2-oxo-1,2-dihydropyridin-3-yl)methyl)-2-methyl-1-(1-(tetrahydro-2H-pyran-4-yl)ethyl)-1H-indole-3-carboxamide | | 456 |

Step 9: (R or S)—N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (Compound 326)

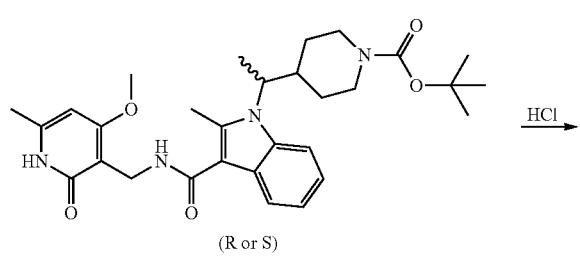

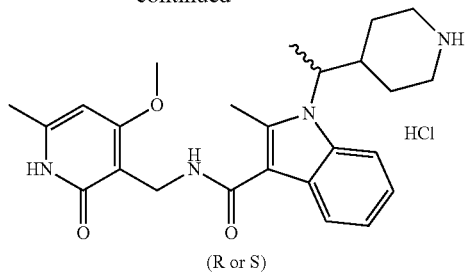

A 250 mL round bottom flask was charged with a magnetic stir bar, (R or S)-tert-butyl 4-(1-(3-((4-methoxy-6-methyl-2-oxo-1,2-dihydropyridin-3-yl)methylcarbamoyl)-2-methyl-1H-indol-1-yl)ethyl)piperidine-1-carboxylate (Compound 327) (1.850 g, 3.45 mmol), MeOH (13.79 ml, 3.45 mmol), and HCl (2.59 ml, 10.34 mmol) (4 N in dioxane). The reaction was allowed to stir at rt for 6 h before being conc. in vacuo to afford the title compound (1.65 g, 3.14 mmol, 91% yield). LCMS 437 (M+1)⁺.

The compound shown in the following table was prepared according to the general procedure outlined in Step 9 using the appropriate starting materials. The structure of this compound is shown in FIG. 1.

| Compound Number | Name | $^1$H NMR | m/z |
|---|---|---|---|
| 376 | (R or S)-1-(1-(1-(azetidin-3-yl)piperidin-4-yl)ethyl)-N-((4,6-dimethyl-2-oxo-1,2-dihydropyridin-3-yl)methyl)-2-methyl-1H-indole-3-carboxamide hydrochloride | (400 MHz, DMSO-d$_6$) δ 12.27-12.10 (m, 1 H), 11.96-11.72 (m, 1 H), 9.80 (br. s., 1 H), 9.19 (br. s., 2 H), 7.89-7.67 (m, 2 H), 7.62 (d, J = 7.6 Hz, 1 H), 7.09 (quin, J = 6.6 Hz, 2 H), 5.99 (s, 1 H), 4.59-4.36 (m, 3 H), 4.24-3.95 (m, 2 H), 3.48 (d, J = 13.2 Hz, 1 H), 3.17 (d, J = 12.0 Hz, 1 H), 2.87 (br. s., 1 H), 2.70 (br. s., 2 H), 2.58 (s, 3 H), 2.34-2.25 (m, 3 H), 2.19-2.10 (m, 3 H), 1.75 (d, J = 12.3 Hz, 1 H), 1.57 (d, J = 6.7 Hz, 3 H), 1.47 (d, J = 12.7 Hz, 2 H), 1.33-1.21 (m, 2 H), 0.85 (d, J = 13.6 Hz, 1 H) | 476 |

Step 10: (R or S)-isopropyl 4-(1-(3-(((4-methoxy-6-methyl-2-oxo-1,2-dihydropyridin-3-yl)methylcarbamoyl)-2-methyl-1H-indol-1-yl)ethyl)piperidine-1-carboxylate (Compound 346)

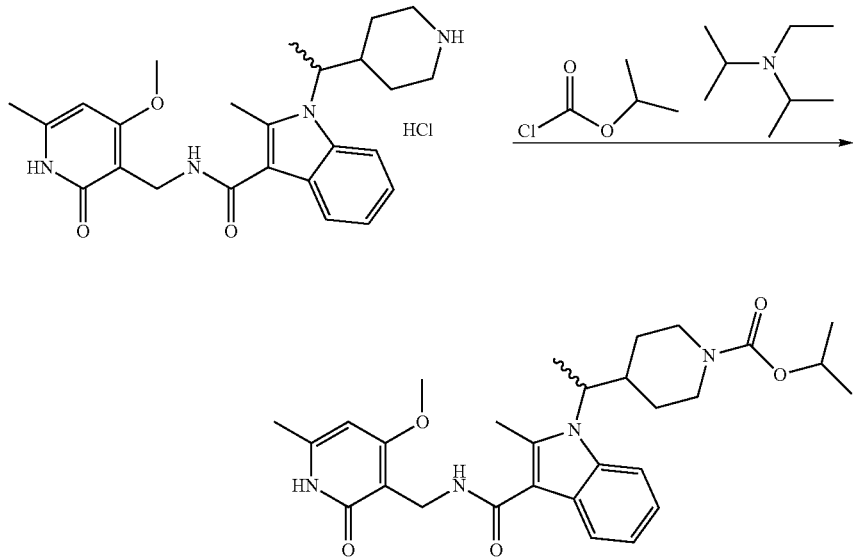

A 250 mL round bottom flask was charged with a magnetic stir bar, (R or S)—N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (0.467 g, 0.987 mmol), DMF (2.468 ml, 0.987 mmol), THF (2.468 ml, 0.987 mmol), and N-ethyl-N-isopropylpropan-2-amine (0.638 g, 4.94 mmol). The reaction was cooled to 0° C. and isopropyl carbonochloridate (0.160 ml, 1.086 mmol) was added drop wise via syringe. The reaction was allowed to stir for 2 h to rt and was then treated with 5 N LiOH for 1 h to remove any acylated pyridone. This material was extracted with ethyl acetate, washed with brine, dried with MgSO$_4$ and filtered and conc. in vacuo. The resulting material was purified via silica gel chromatography (50 g) using ethyl acetate/MeOH (5:1) as eluent to afford pure title compound as a pale yellow solid (0.300 g, 0.545 mmol, 55.2% yield). LCMS 523 (M+1)$^+$; $^1$H NMR (DMSO-d6, 400 MHz) δ 11.59 (br. s., 1H), 7.74 (d, J=7.8 Hz, 1H), 7.69 (t, J=4.9 Hz, 1H), 7.62 (d, J=7.8 Hz, 1H), 7.13-7.01 (m, 2H), 6.15 (s, 1H), 4.78-4.67 (m, 1H), 4.32 (d, J=4.9 Hz, 2H), 4.23-4.12 (m, 1H), 4.12-4.02 (m, 1H), 3.84 (s, 3H), 3.82-3.74 (m, 1H), 2.79-2.66 (m, 1H), 2.58 (s, 3H), 2.46-2.34 (m, 2H), 2.20 (s, 3H), 1.96-1.88 (m, 1H), 1.58-1.46 (m, 4H), 1.15 (d, J=6.0 Hz, 6H), 0.95-0.89 (m, 1H), 0.74-0.65 (m, 1H).

The compounds shown in the following table were prepared according to the general procedure outlined in Step 10 using the appropriate starting materials. The structures of the compounds are shown in FIG. 1.

| Compound Number | Name | ¹H NMR | m/z |
|---|---|---|---|
| 336 | (R or S)-N-((4-methoxy-6-methyl-2-oxo-1,2-dihydropyridin-3-yl)methyl)-2-methyl-1-(1-(1-(methylsulfonyl)piperidin-4-yl)ethyl)-1H-indole-3-carboxamide | (400 MHz, DMSO-d$_6$) δ = 11.59 (s, 1 H), 7.78-7.66 (m, 2 H), 7.64-7.57 (m, 1 H), 7.06 (s, 2 H), 6.14 (s, 1 H), 4.31 (d, J = 4.9 Hz, 2 H), 4.25-4.15 (m, 1 H), 3.83 (s, 3 H), 3.63 (s, 1 H), 3.40-3.33 (m, 1 H), 2.79 (s, 3 H), 2.75-2.65 (m, 1 H), 2.60 (s, 3 H), 2.45-2.27 (m, 1 H), 2.19 (s, 3 H), 2.06-1.98 (m, 1 H), 1.55 (d, J = 6.9 Hz, 3 H), 1.45-1.36 (m, 1 H), 1.28-1.18 (m, 1 H), 1.14-1.03 (m, 1 H), 0.83-0.74 (m, 1 H) | 515 |
| 337 | (R or S)-1-(1-(2-hydroxy-2-methylpropanoyl)piperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-d$_6$) δ 11.58 (br. s., 1 H), 7.77-7.67 (m, 2 H), 7.66-7.60 (m, 1 H), 7.06 (s, 2 H), 6.14 (s, 1 H), 5.32-5.23 (m, 1 H), 4.31 (d, J = 4.5 Hz, 2 H), 4.19-4.10 (m, 1 H), 3.83 (s, 3 H), 2.75-2.62 (m, 2 H), 2.58 (s, 3 H), 2.19 (s, 4 H), 2.00-1.90 (m, 2 H), 1.54 (d, J = 6.7 Hz, 3 H), 1.32-1.18 (m, 8 H), 0.87-0.78 (m, 1 H), 0.77-0.67 (m, 1 H) | 523 |
| 342 | (R or S)-1-(1-(1-isobutyrylpiperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-d$_6$) δ = 11.59 (s, 1 H), 7.75 (d, J = 7.4 Hz, 1 H), 7.72-7.67 (m, 1 H), 7.64 (d, J = 8.0 Hz, 1 H), 7.14-7.01 (m, 2 H), 6.15 (s, 1 H), 4.58-4.46 (m, 1 H), 4.32 (d, J = 4.9 Hz, 2 H), 4.09-3.99 (m, 1 H), 3.84 (s, 3 H), 3.81-3.72 (m, 1 H), 3.08-2.97 (m, 1 H), 2.92-2.81 (m, 1 H), 2.78-2.65 (m, 3 H), 2.59 (br. s., 3 H), 2.20 (s, 3 H), 2.03-1.90 (m, 1 H), 1.59-1.47 (m, 4 H), 1.02-0.86 (m, 6 H), 0.78-0.69 (m, 1 H) | 507 |
| 344 | (R or S)-N-((4-(difluoromethoxy)-6-methyl-2-oxo-1,2-dihydropyridin-3-yl)methyl)-2-methyl-1-(1-(1-(methylsulfonyl)piperidin-4-yl)ethyl)-1H-indole-3-carboxamide | (400 MHz, DMSO-d$_6$) δ 12.02-11.95 (m, 1 H), 7.74 (d, J = 8.0 Hz, 1 H), 7.66-7.57 (m, 2 H), 7.11-7.00 (m, 2 H), 6.08 (s, 1 H), 4.32 (d, J = 4.5 Hz, 2 H), 4.18 (d, J = 7.1 Hz, 1 H), 3.64 (d, J = 12.3 Hz, 1 H), 3.36 (d, J = 12.0 Hz, 1 H), 2.79 (s, 3 H), 2.75-2.65 (m, 2 H), 2.58 (s, 3 H), 2.45-2.27 (m, 2 H), 2.20 (s, 3 H), 2.07-1.98 (m, 1 H), 1.55 (d, J = 6.9 Hz, 3 H), 1.40 (d, J = 8.2 Hz, 1 H), 1.10 (d, J = 8.9 Hz, 1 H), 0.79 (d, J = 12.5 Hz, 1 H) | 551 |
| 345 | (R or S)-1-(1-(1-(ethylsulfonyl)piperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-d$_6$) δ 11.57 (s, 1 H), 7.75 (d, J = 8.0 Hz, 1 H), 7.69 (t, J = 5.0 Hz, 1 H), 7.62 (d, J = 7.4 Hz, 1 H), 7.06 (d, J = 7.1 Hz, 2 H), 6.15 (s, 1 H), 4.32 (d, J = 5.1 Hz, 2 H), 4.25-4.15 (m, 1 H), 3.84 (s, 3 H), 3.73-3.65 (m, 1 H), 3.45-3.36 (m, 1 H), 3.02-2.93 (m, J = 7.8 Hz, 2 H), 2.87-2.77 (m, 1 H), 2.75-2.66 (m, 1 H), 2.60 (s, 3 H), 2.42-2.30 (m, 1 H), 2.20 (s, 3 H), 2.06-1.97 (m, 1 H), 1.58-1.48 (m, 4 H), 1.42-1.31 (m, 1 H), 1.17 (t, J = 7.5 Hz, 3 H), 1.13-1.00 (m, 1 H), 0.83-0.73 (m, 1 H) | 529 |

-continued

| Compound Number | Name | ¹H NMR | m/z |
|---|---|---|---|
| 355 | (R or S)-1-(1-(4-(isopropylsulfonyl)cyclohexyl)ethyl)-N-((4-methoxy-6-methyl-2-oxo-1,2-dihydropyridin-3-yl)methyl)-2-methyl-1H-indole-3-carboxamide | (400 MHz, DMSO-$d_6$) δ 11.59 (s, 1H), 7.76-7.69 (m, 2H), 7.62 (d, 1H), 7.10-7.03 (m, 2H), 6.15 (s, 1H), 4.32 (d, 2H), 4.29-4.26 (m, 2H), 3.84 (s, 3H), 3.72 (br. d., 1H), 3.45 (br. d., 1H), 3.26 (tt, 1H), 2.91 (dt, 1H), 2.60 (s, 3H), 2.20 (s, 3H), 1.97 (br. d., 1H), 1.54 (d, 3H), 1.35-1.24 (m, 2H), 1.18 (d, 3H), 1.16 (d, 3H), 1.05-0.78 (m, 2H) | 543 |
| 357 | (R or S)-isobutyl 4-(1-(3-(((4-methoxy-6-methyl-2-oxo-1,2-dihydropyridin-3-yl)methyl)carbamoyl)-2-methyl-1H-indol-1-yl)ethyl)piperidine-1-carboxylate | (400 MHz, DMSO-$d_6$) δ 11.60 (br. s., 1H), 7.75-7.60 (m, 3H), 7.10-7.03 (m, 2H), 6.15 (s, 1H), 4.33 (d, 1H), 4.13-4.06 (m, 1H), 3.84 (s, 3H), 3.74 (d, 1H), 2.80-2.60 (m, 3H), 2.58 (s, 1H), 2.50-2.42 (m, 2H), 1.96-1.90 (m, 1H), 1.54 (d, 3H), 1.25-1.22 (m, 1H), 0.98-0.72 (m, 6H) | 537 |
| 368 | (R or S)-N-((4,6-dimethyl-2-oxo-1,2-dihydropyridin-3-yl)methyl)-1-(1-(1-(ethylsulfonyl)piperidin-4-yl)ethyl)-2-methyl-1H-indole-3-carboxamide | (400 MHz, DMSO-$d_6$) δ 11.59 (s, 1 H), 7.78-7.71 (m, 1 H), 7.66-7.57 (m, 2 H), 7.07 (s, 2 H), 5.89 (s, 1 H), 4.32 (s, 2 H), 4.25-4.15 (m, 1 H), 3.65-3.59 (m, 1 H), 3.19-3.10 (m, 1 H), 2.98 (d, J = 7.4 Hz, 2 H), 2.87-2.77 (m, 1 H), 2.72-2.65 (m, 1 H), 2.58 (s, 3 H), 2.27 (s, 3 H), 2.12 (s, 3 H), 1.55 (d, J = 6.9 Hz, 4 H), 1.42-1.33 (m, 2 H), 1.17 (t, J = 7.4 Hz, 3 H), 1.12-1.00 (m, 1 H), 0.84-0.74 (m, 1 H) | 513 |
| 382 | (R or S)-N-((4,6-dimethyl-2-oxo-1,2-dihydropyridin-3-yl)methyl)-2-methyl-1-(1-(1-(methylsulfonyl)piperidin-4-yl)ethyl)-1H-indole-3-carboxamide | (400 MHz, DMSO-$d_6$) δ 11.60 (s, 1 H), 7.75 (d, J = 7.1 Hz, 1 H), 7.65-7.58 (m, 2 H), 7.12-7.02 (m, 2 H), 5.89 (s, 1 H), 4.38-4.25 (m, 2 H), 4.20 (dd, J = 7.0, 10.6 Hz, 1 H), 2.80 (s, 3 H), 2.76-2.67 (m, 2 H), 2.59 (s, 3 H), 2.46-2.31 (m, 2 H), 2.27 (s, 3 H), 2.12 (s, 3 H), 1.55 (d, J = 6.9 Hz, 3 H), 1.51 (br. s., 1 H), 1.47-1.34 (m, 1 H), 1.29-1.21 (m, 1 H), 1.17-1.04 (m, 1 H), 0.80 (d, J = 12.9 Hz, 1 H) | 499 |

Example 2

Synthesis of (R or S)-1-(1-(1-isopropylpiperidin-4-yl)ethyl)-N-((4-methoxy-6-methyl-2-oxo-1,2-dihydropyridin-3-yl)methyl)-2-methyl-1H-indole-3-carboxamide (Compound 358)

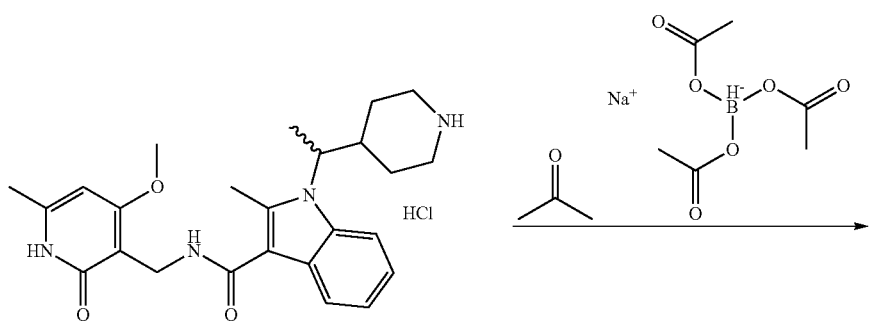

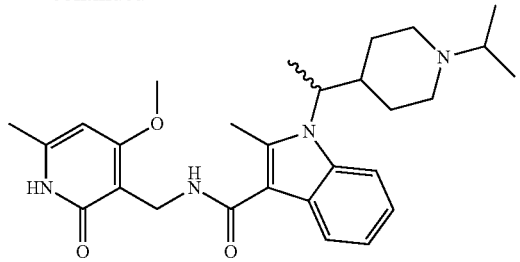

A 25 mL vial was charged with a magnetic stir bar, (R or S)—N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride, THF (2.114 ml, 0.211 mmol), propan-2-one (0.061 g, 1.057 mmol), and sodium triacetoxyborohydride (0.224 g, 1.057 mmol). The reaction was allowed to stir at rt for 12 h. The reaction was inverse quenched onto sat'd aqueous NaHCO₃, extracted with ethyl acetate and conc. in vacuo. The resulting material was treated with 10 mL 7 N ammonia in MeOH and was conc in vacuo to yield material which was purified via silica gel chromatography (10 g) using DCM/MeOH/NH₄OH (90:1: 0.1) as eluent to afford 33 mg, (0.065 mmol, 31.0% yield) of the title compound as a white solid.). LCMS 479 (M+1)⁺; ¹H NMR (DMSO-d6, 400 MHz) δ 11.59 (s., 1H), 7.64-7.82 (m, 2H), 7.59 (d, 1H), 6.95-7.17 (m, 2H), 6.15 (s, 1H), 4.32 (d, 2H), 4.04-4.24 (m, 1H), 3.84 (□, 3H), 2.77-2.93 (□, 2H), 2.68 (□, 1H), 2.60 (□, 3H), 2.20 (□, 3H), 2.08-2.15 (□, 1H), 1.92 (□, 1H), 1.83 (□p. □., 1H), 1.54 (□, 3H), 1.27-1.43 (□, 2H), 0.91 (□, 6H), 0.71-0.67 (□, 2H).

The compounds shown in the following table were prepared according to the general procedure outlined in this Example using the appropriate starting materials. The structures of the compounds are shown in FIG. 1.

| Compound Number | Name | ¹H NMR | m/z |
|---|---|---|---|
| 341 | (R or S)-N-((4-methoxy-6-methyl-2-oxo-1,2-dihydropyridin-3-yl)methyl)-2-methyl-1-(1-(1-(oxetan-3-yl)piperidin-4-yl)ethyl)-1H-indole-3-carboxamide | (400 MHz, DMSO-d₆) δ 11.58 (s, 1 H), 7.76-7.65 (m, 2 H), 7.59 (d, J = 7.8 Hz, 1 H), 7.10-6.99 (m, 2 H), 6.14 (s, 1 H), 4.49 (t, J = 6.4 Hz, 1 H), 4.43 (t, J = 6.5 Hz, 1 H), 4.37 (t, J = 6.1 Hz, 1 H), 4.34-4.28 (m, 3 H), 4.21-4.10 (m, 1 H), 3.83 (s, 3 H), 3.30-3.23 (m, 1 H), 2.75 (br. s., 1 H), 2.71-2.64 (m, 1 H), 2.60 (s, 3 H), 2.19 (s, 4 H), 1.90 (br. s., 1 H), 1.75 (br. s., 1 H), 1.53 (d, J = 6.9 Hz, 3 H), 1.42 (br. s., 2 H), 1.11-0.98 (m, 1 H), 0.72-0.63 (m, 1 H) | 493 |
| 343 | (R or S)-N-((4-methoxy-6-methyl-2-oxo-1,2-dihydropyridin-3-yl)methyl)-2-methyl-1-(1-(1-methylpiperidin-4-yl)ethyl)-1H-indole-3-carboxamide | (400 MHz, DMSO-d₆) δ 11.58 (s, 1 H), 7.76-7.65 (m, 2 H), 7.59 (d, J = 7.6 Hz, 1 H), 7.11-6.99 (m, 2 H), 6.14 (s, 1 H), 4.31 (d, J = 5.1 Hz, 2 H), 4.13 (br. s., 1 H), 3.83 (s, 3 H), 2.83 (d, J = 10.0 Hz, 1 H), 2.61-2.52 (m, 5 H), 2.19 (s, 3 H), 2.09 (s, 4 H), 1.88 (d, J = 10.7 Hz, 2 H), 1.53 (d, J = 6.7 Hz, 3 H), 1.34 (br. s., 1 H), 1.02 (d, J = 8.2 Hz, 1 H), 0.66 (br. s., 1 H) | 451 |
| 359 | (R or S)-N-((4-methoxy-6-methyl-2-oxo-1,2-dihydropyridin-3-yl)methyl)-1-(1-(1-(2-methoxyethyl)piperidin-4-yl)ethyl)-2-methyl-1H-indole-3-carboxamide | (400 MHz, DMSO-d₆) δ 11.59 (s, 1 H), 7.77-7.66 (m, 2 H), 7.60 (d, J = 7.8 Hz, 1 H), 7.12-7.01 (m, 2 H), 6.15 (s, 1 H), 4.32 (d, J = 4.9 Hz, 2 H), 4.13 (d, J = 7.1 Hz, 1 H), 3.85 (s, 3 H), 3.36 (t, J = 5.9 Hz, 2 H), 3.19 (s, 3 H), 2.94 (d, J = 10.5 Hz, 1 H), 2.71-2.56 (m, 5 H), 2.43-2.32 (m, 2 H), 2.24-2.12 (m, 4 H), 1.54 (d, J = 6.9 Hz, 4 H), 1.39-1.27 (m, 2 H), 1.02 (d, J = 8.7 Hz, 1 H), 0.65 (d, J = 12.7 Hz, 1 H) | 495 |
| 360 | (R or S)-1-(1-(1-ethylpiperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-d₆) δ 11.79-11.45 (m, 1 H), 7.78-7.65 (m, 2 H), 7.59 (d, J = 7.8 Hz, 1 H), 7.14-6.99 (m, 2 H), 6.15 (s, 1 H), 4.32 (d, J = 4.9 Hz, 2 H), 4.20-4.08 (m, 1 H), 3.84 (s, 3 H), 2.98-2.89 (m, 1 H), 2.71-2.61 (m, 2 H), 2.59 (s, 3 H), 2.27-2.21 (m, 2 H), 2.20 (s, 3 H), 1.94-1.80 (m, 2 H), 1.54 (s, 4 H), 1.38-1.28 (m, 1 H), 1.06-0.98 (m, 1 H), 0.93 (t, J = 7.1 Hz, 3 H), 0.71-0.63 (m, 1 H) | 465 |
| 363 | (R or S)-ethyl 2-(4-(1-(3-(((4-methoxy-6-methyl-2-oxo-1,2-dihydropyridin-3-yl)methyl)carbamoyl)-2-methyl-1H-indol-1- | (400 MHz, DMSO-d₆) δ 11.59 (br. s., 1 H), 7.81-7.65 (m, 2 H), 7.60 (d, J = 7.4 Hz, 1 H), 7.16-6.98 (m, 2 H), 6.15 (s, 1 H), 4.32 (d, J = 4.9 Hz, 2 H), 4.23-4.11 (m, 1 H), 4.04 (q, J = 7.0 Hz, 2 H), 3.84 (s, 3 H), 2.95-2.86 (m, 1 H), 2.60 (s, 5 H), 2.20 (s, 4 | 523 |

| Compound Number | Name | ¹H NMR | m/z |
|---|---|---|---|
| | yl)ethyl)piperidin-1-yl)acetate | H), 1.94-1.79 (m, 2 H), 1.54 (d, J = 6.9 Hz, 4 H), 1.41-1.32 (m, 1 H), 1.15 (t, J = 7.1 Hz, 3 H), 1.04 (d, J = 6.0 Hz, 2 H), 0.71-0.61 (m, 1 H) | |
| 366 | (R or S)-N-((4-ethyl-6-methyl-2-oxo-1,2-dihydropyridin-3-yl)methyl)-2-methyl-1-(1-(1-methylpiperidin-4-yl)ethyl)-1H-indole-3-carboxamide | (400 MHz, DMSO-d₆) δ 11.63 (s, 1 H), 7.74 (d, J = 7.6 Hz, 1 H), 7.65-7.56 (m, 2 H), 7.12-7.01 (m, 2 H), 5.94 (s, 1 H), 4.34 (t, J = 5.1 Hz, 2 H), 4.19-4.09 (m, 1 H), 2.88 (br. s., 1 H), 2.71-2.56 (m, 6 H), 2.14 (s, 7 H), 1.91 (d, J = 12.5 Hz, 1 H), 1.54 (d, J = 6.9 Hz, 4 H), 1.41-1.31 (m, 2 H), 1.14 (t, J = 7.6 Hz, 3 H), 1.05 (d, J = 9.1 Hz, 1 H), 0.68 (d, J = 12.7 Hz, 1 H) | 449 |
| 367 | (R or S)-N-((4,6-dimethyl-2-oxo-1,2-dihydropyridin-3-yl)methyl)-2-methyl-1-(1-(1-methylpiperidin-4-yl)ethyl)-1H-indole-3-carboxamide | (400 MHz, DMSO-d₆) δ 11.59 (s, 1 H), 7.74 (d, J = 6.9 Hz, 1 H), 7.65-7.56 (m, 2 H), 7.12-7.01 (m, 2 H), 5.89 (s, 1 H), 4.38-4.25 (m, 2 H), 4.20-4.09 (m, 1 H), 2.95 (br. s., 1 H), 2.68 (br. s., 2 H), 2.58 (s, 3 H), 2.27 (s, 3 H), 2.21 (br. s., 3 H), 2.12 (s, 3 H), 1.94 (d, J = 13.8 Hz, 1 H), 1.54 (d, J = 6.9 Hz, 4 H), 1.44-1.31 (m, 2 H), 1.07 (d, J = 12.5 Hz, 1 H), 0.71 (d, J = 13.2 Hz, 1 H) | 435 |
| 375 | (R or S)-N-((4,6-dimethyl-2-oxo-1,2-dihydropyridin-3-yl)methyl)-2-methyl-1-(1-(1-(oxetan-3-yl)piperidin-4-yl)ethyl)-1H-indole-3-carboxamide | (400 MHz, DMSO-d₆) δ 11.59 (br. s., 1 H), 7.73 (d, J = 7.6 Hz, 1 H), 7.65-7.55 (m, 2 H), 7.12-7.00 (m, 2 H), 5.89 (s, 1 H), 4.53-4.48 (m, 1 H), 4.47-4.42 (m, 1 H), 4.38 (s, 1 H), 4.31 (t, J = 5.2 Hz, 3 H), 4.21-4.10 (m, 1 H), 3.31-3.24 (m, 2 H), 2.81-2.64 (m, 2 H), 2.59 (s, 3 H), 2.26 (s, 3 H), 2.23-2.16 (m, 1 H), 2.12 (s, 3 H), 1.98-1.85 (m, 1 H), 1.81-1.70 (m, 1 H), 1.54 (d, J = 6.9 Hz, 3 H), 1.51-1.22 (m, 1 H), 1.12-0.96 (m, 2 H), 0.73-0.64 (m, 1 H) | 477 |
| 380 | (R or S)-N-((4-ethyl-6-methyl-2-oxo-1,2-dihydropyridin-3-yl)methyl)-2-methyl-1-(1-(1-(oxetan-3-yl)piperidin-4-yl)ethyl)-1H-indole-3-carboxamide | (400 MHz, DMSO-d₆) δ 11.63 (br. s., 1 H), 7.74 (d, J = 7.36 Hz, 1 H), 7.60 (d, J = 8.47 Hz, 2 H), 7.06 (quin, J = 7.13 Hz, 3 H), 5.94 (s, 1 H), 4.51 (t, J = 6.47 Hz, 1 H), 4.46 (t, J = 6.35 Hz, 1 H), 4.40 (t, J = 6.13 Hz, 1 H), 4.37-4.30 (m, 2 H), 4.28-4.11 (m, 1 H), 3.57 (s, 1 H), 3.34 (br. s., 1 H), 2.81 (d, J = 10.70 Hz, 1 H), 2.67 (d, J = 14.94 Hz, 1 H), 2.64-2.57 (m, 4 H), 2.21 (d, J = 10.93 Hz, 1 H), 2.14 (s, 3 H), 1.93 (d, J = 12.49 Hz, 1 H), 1.83 (t, J = 11.37 Hz, 1 H), 1.54 (d, J = 6.91 Hz, 3 H), 1.37 (d, J = 10.48 Hz, 1 H), 1.25 (q, J = 6.91 Hz, 1 H), 1.14 (t, J = 7.58 Hz, 3 H), 1.06 (d, J = 9.81 Hz, 1 H), 0.70 (d, J = 12.49 Hz, 1 H) | 491 |
| 381 | (R or S)-N-((4,6-dimethyl-2-oxo-1,2-dihydropyridin-3-yl)methyl)-2-methyl-1-(1-(1-(tetrahydro-2H-pyran-4-yl)piperidin-4-yl)ethyl)-1H-indole-3-carboxamide | ¹H NMR (400 MHz, DMSO-d₆) δ 11.60 (br. s., 1 H), 7.74 (d, J = 7.13 Hz, 1 H), 7.66-7.50 (m, 2 H), 7.15-6.99 (m, 2 H), 5.89 (s, 1 H), 4.40-4.24 (m, 2 H), 4.21-4.07 (m, 1 H), 3.95-3.78 (m, 2 H), 3.57 (s, 1 H), 3.32-3.17 (m, 3 H), 2.68 (br. s., 1 H), 2.58 (s, 3 H), 2.33 (br. s., 2 H), 2.27 (s, 3 H), 2.12 (s, 3 H), 2.00-1.88 (m, 2 H), 1.75 (d, J = 12.04 Hz, 1 H), 1.62 (br. s., 2 H), 1.54 (d, J = 6.91 Hz, 3 H), 1.46-1.30 (m, 2 H), 1.01 (br. s., 1 H), 0.72 (br. s., 1 H) | 505 |
| 440 | (R or S)-tert-butyl 3-(4-(1-(3-(((4,6-dimethyl-2-oxo-1,2-dihydropyridin-3-yl)methyl)carbamoyl)-2-methyl-1H-indol-1-yl)ethyl)piperidin-1-yl)azetidine-1-carboxylate | | 576 |

| Compound Number | Name | ¹H NMR | m/z |
|---|---|---|---|
| 377 | (R or S)-N-((4,6-dimethyl-2-oxo-1,2-dihydropyridin-3-yl)methyl)-2-methyl-1-(1-(1-(1-methylazetidin-3-yl)piperidin-4-yl)ethyl)-1H-indole-3-carboxamide | (400 MHz, DMSO-d₆) δ 11.63-11.56 (m, 1 H), 7.76-7.70 (m, 1 H ), 7.64-7.55 (m, 2 H), 7.05 (s, 2 H), 5.89 (s, 1 H), 4.56 (s, 4 H), 4.31 (s, 2 H), 4.19-4.09 (m, 1 H), 3.36 (d, J = 4.9 Hz, 1 H), 2.77-2.56 (m, 5 H), 2.26 (s, 3 H), 2.18 (s, 3 H), 2.12 (s, 3 H), 1.94-1.85 (m, 1 H), 1.78-1.67 (m, 1 H), 1.53 (d, J = 6.9 Hz, 3 H), 1.50-1.45 (m, 1 H), 1.44-1.22 (m, 2 H), 1.07-0.93 (m, 1 H), 0.71-0.61 (m, 1 H) | 490 |

Example 3

Synthesis of (R or S)-1-(1-(1-(2-fluoroethyl)piperidin-4-yl)ethyl)-N-((4-methoxy-6-methyl-2-oxo-1,2-dihydropyridin-3-yl)methyl)-2-methyl-1H-indole-3-carboxamide (Compound 356)

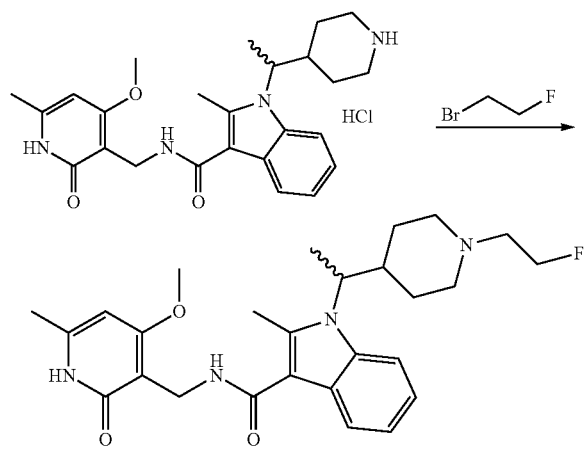

A 25 mL vial was charged with a magnetic stir bar, (R or S)—N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (0.062 g, 0.131 mmol), K₂CO₃ (0.072 g, 0.524 mmol), MeCN (0.655 ml, 0.131 mmol), DMF (0.262 ml, 0.131 mmol) and 1-bromo-2-fluoroethane (0.020 ml, 0.262 mmol). The reaction was capped and heated to 82° C. with stirring for 4 h. The reaction was allowed to cool to rt, filtered, and the filtrate was pre-absorbed onto silica gel (12 g). The material was purified via SiO₂ chromatography (25 g) using DCM/MeOH/Et₃N (85:15:0.5) as eluent to afford the title compound as an off white solid (30 mg, 0.059 mmol, 45.1% yield). LCMS 483 (M+1)⁺; ¹H NMR (DMSO-d6, 400 MHz) δ 11.59 (s, 1H), 7.75-7.68 (m, 2H), 7.60 (d, 1H) 7.09-7.03 (m, 2H), 6.15 (s, 1H) 4.53-4.51 (m, 1H), 4.42-4.39 (m, 1H), 4.32 (d, 2H), 4.24-4.2 (m, 1H), 3.84 (s, 3H), 2.98 (br. d., 1H), 2.70-2.49 (m, 4H), 2.60 (s, 3H), 2.20 (s, 3H), 2.01 (dt, 1H), 1.92-1.90 (m, 1H), 1.75-1.71 (m, 1H), 1.54 (d, 3H), 1.38-1.36 (m, 1H), 1.02-0.98 (m, 1H), 0.7-0.66 (br. d., 1H).

The compounds shown in the following table were prepared according to the general procedure outlined in this Example using the appropriate starting materials. The structures of the compounds are shown in FIG. 1.

| Compound Number | Name | ¹H NMR | m/z |
|---|---|---|---|
| 362 | (R or S)-1-(1-(1-(2,2-difluoroethyl)piperidin-4-yl)ethyl)-N-((4-methoxy-6-methyl-2-oxo-1,2-dihydropyridin-3-yl)methyl)-2-methyl-1H-indole-3-carboxamide | (400 MHz, DMSO-d₆) δ = 11.60 (br. s., 1 H), 7.77-7.66 (m, 2 H), 7.60 (d, J = 7.6 Hz, 1 H), 7.14-7.00 (m, 2H ), 6.15 (s, 1 H), 6.06 (t, J = 55.7 Hz, 1 H), 4.32 (d, J = 4.9 Hz, 2 H), 4.15 (br. s., 1 H), 3.84 (s, 3 H), 3.03-2.93 (m, 2 H), 2.73-2.62 (m, 3 H), 2.60 (s, 3 H), 2.26-2.10 (m, 4 H), 1.93-1.79 (m, 1 H), 1.59-1.46 (m, 4 H), 1.41-1.29 (m, 1 H), 1.11-0.97 (m, 1 H), 0.67 (br. s., 1 H) | 501 |
| 378 | (R or S)-N-((4-methoxy-6-methyl-2-oxo-1,2-dihydropyridin-3-yl)methyl)-2-methyl-1-(1-(1-(3,3,3-trifluoropropyl)piperidin-4-yl)ethyl)-1H-indole-3-carboxamide | (400 MHz, DMSO-d₆) δ = 11.60 (br. s., 1 H), 7.78-7.66 (m, 2 H), 7.60 (d, J = 8.2 Hz, 1 H), 7.13-7.00 (m, 2 H), 6.15 (s, 1 H), 4.32 (d, J = 4.9 Hz, 2 H), 4.22-4.09 (m, 1 H), 3.84 (s, 3 H), 3.03-2.91 (m, 1 H), 2.73-2.64 (m, 1 H), 2.60 (s, 3 H), 2.48-2.31 (m, 5 H), 2.20 (s, 3 H), 2.01-1.85 (m, 2 H), 1.58-1.46 (m, 4 H), 1.36-1.29 (m, 1 H), 1.08-0.98 (m, 1 H), 0.73-0.62 (m, 1 H) | 533 |

-continued

| Compound Number | Name | ¹H NMR | m/z |
|---|---|---|---|
| 365 | (R or S)-N-((4-methoxy-6-methyl-2-oxo-1,2-dihydropyridin-3-yl)methyl)-2-methyl-1-(1-(2,2,2-trifluoroethyl)piperidin-4-yl)ethyl)-1H-indole-3-carboxamide | (500 MHz, DMSO-d₆) δ = 11.59 (s, 1 H), 7.74 (d, J = 7.6 Hz, 1 H), 7.71-7.66 (m, 1 H), 7.61 (d, J = 7.8 Hz, 1 H), 7.13-7.01 (m, 2 H), 6.15 (s, 1 H), 4.32 (d, J = 4.9 Hz, 2 H), 4.22-4.12 (m, 1 H), 3.84 (s, 3 H), 3.15-2.95 (m, 3 H), 2.75-2.66 (m, 1 H), 2.60 (s, 3 H), 2.39-2.31 (m, 1 H), 2.20 (s, 3 H), 2.05-1.98 (m, 1 H), 1.92-1.84 (m, 1 H), 1.56-1.46 (m, 4 H), 1.42-1.32 (m, 1 H), 1.11-1.01 (m, 1 H), 0.69-0.62 (m, 1 H) | 519 |
| 441 | (R or S)-1-(1-(1-(2,2-difluoroethyl)piperidin-4-yl)ethyl)-N-((4,6-dimethyl-2-oxo-1,2-dihydropyridin-3-yl)methyl)-2-methyl-1H-indole-3-carboxamide | (400 MHz, DMSO-d₆) δ = 11.59 (s, 1 H), 7.73 (d, J = 7.8 Hz, 1 H), 7.65-7.55 (m, 2 H), 7.12-7.00 (m, 2 H), 6.22-5.90 (m, 1 H), 5.89 (s, 1 H), 4.36-4.25 (m, 2 H), 4.20-4.09 (m, 1 H), 3.01-2.93 (m, 1 H), 2.72-2.59 (m, 3 H), 2.58 (s, 3 H), 2.26 (s, 3 H), 2.21-2.13 (m, 2 H), 2.12 (s, 3 H), 1.92-1.79 (m, 2 H), 1.53 (s, 4 H), 1.41-1.29 (m, 1 H), 1.10-0.97 (m, 1 H), 0.70-0.59 (m, 1 H) | 485 |

Example 4

Synthesis of (R or S)—N-((4-methoxy-6-methyl-2-oxo-1,2-dihydropyridin-3-yl)methyl)-2-methyl-1-(1-(1-(pyrimidin-2-yl)piperidin-4-yl)ethyl)-1H-indole-3-carboxamide (Compound 361)

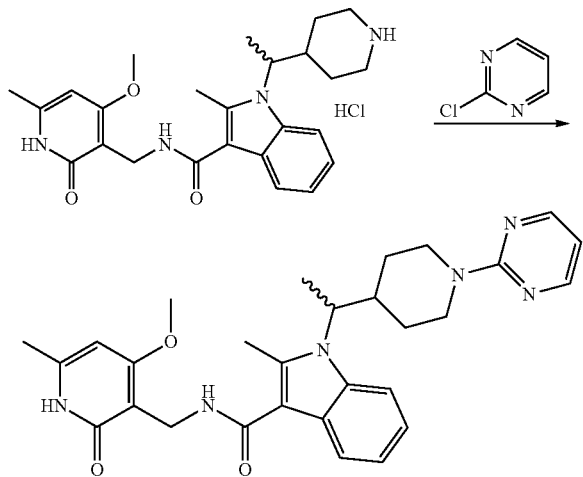

To a re-sealable vial was added 2-chloropyrimidine (185 mg, 1.611 mmol), (R or S)—N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (508 mg, 1.074 mmol), and EtOH (8 mL). To this solution was added Et₃N (449 μl, 3.22 mmol). The vial was sealed and heated to 100° C. overnight. The solution was allowed to cool to room temperature and concentrated in vacuo. The crude residue was purified via silica gel chromatography (hexanes: (3:2 DCM:IPA)) to afford the title compound as a solid (357 mg, 0.694 mmol, 64.6% yield). LCMS 515 (M+1)⁺; ¹H NMR (DMSO-d6, 400 MHz) δ 11.60 (s, 1H), 8.30 (d, J=4.7 Hz, 2H), 7.76 (d, J=7.6 Hz, 1H), 7.73-7.64 (m, 2H), 7.14-7.01 (m, 2H), 6.55 (t, J=4.7 Hz, 1H), 6.15 (s, 1H), 4.84-4.75 (m, 1H), 4.57-4.47 (m, 1H), 4.33 (d, J=4.2 Hz, 2H), 4.22-4.11 (m, 1H), 3.84 (s, 3H), 2.92-2.81 (m, 1H), 2.63-2.52 (m, 4H), 2.20 (s, 3H), 2.05-1.94 (m, 1H), 1.61-1.49 (m, 4H), 1.34-1.21 (m, 1H), 1.04-0.91 (m, 1H), 0.83-0.75 (m, 1H).

The compound shown in the following table was prepared according to the general procedure outlined in this Example using the appropriate starting materials. The structure of the compound is shown in FIG. 1.

| Compound Number | Name | ¹H NMR | m/z |
|---|---|---|---|
| 373 | (R or S)-N-((4-methoxy-6-methyl-2-oxo-1,2-dihydropyridin-3-yl)methyl)-2-methyl-1-(1-(1-(pyridin-2-yl)piperidin-4-yl)ethyl)-1H-indole-3-carboxamide | (400 MHz, DMSO-d₆) δ 11.60 (br. s., 1 H), 8.06 (d, J = 3.6 Hz, 1 H), 7.82-7.62 (m, 3 H), 7.51-7.39 (m, 1 H), 7.17-6.98 (m, 2 H), 6.75 (d, J = 8.5 Hz, 1 H), 6.61-6.49 (m, 1 H), 6.15 (s, 1 H), 4.49-4.38 (m, 1 H), 4.33 (d, J = 3.8 Hz, 2 H), 4.24-4.03 (m, 2 H), 3.85 (s, 3 H), 2.90-2.70 (m, 2 H), 2.58 (s, 3 H), 2.20 (s, 3 H), 2.06-1.91 (m, 1 H), 1.63-1.47 (m, 4 H), 1.40-1.27 (m, 1 H), 1.07-0.94 (m, 1 H), 0.82-0.72 (m, 1 H) | 514 |

Example 5

Synthesis of (R or S)-1-(1-(1-(2-hydroxyethyl)piperidin-4-yl)ethyl)-N-((4-methoxy-6-methyl-2-oxo-1,2-dihydropyridin-3-yl)methyl)-2-methyl-1H-indole-3-carboxamide (Compound 347)

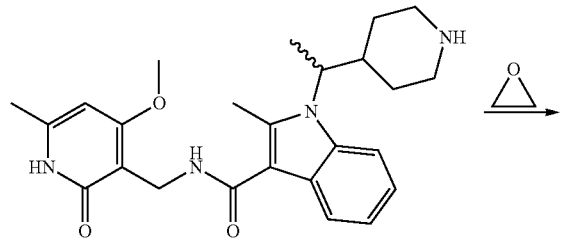

To a sealed tube charged with a magnetic stir bar was added (R or S)—N-((4-methoxy-6-methyl-2-oxo-1,2-dihydropyridin-3-yl)methyl)-2-methyl-1-(1-(piperidin-4-yl)ethyl)-1H-indole-3-carboxamide (0.1 g, 0.229 mmol) was added DCM (3 mL) and the reaction cooled to 0° C. To the cooled reaction mixture was added oxirane which was condensed into the reaction vial (~1 mL). The reaction was allowed to stir to rt over 4 h and was then conc. in vacuo to afford the crude material which was purified via silica gel chromatography (12 g) using ethyl acetate/MeOH (4:1) as eluent to afford the title compound as a white solid (50 mg). LCMS 481 (M+1)+; $^1$H NMR (DMSO-d6, 400 MHz) δ) δ 11.58 (s, 1H), 7.77-7.65 (m, 2H), 7.59 (d, J=7.8 Hz, 1H), 7.11-6.99 (m, 2H), 6.14 (s, 1H), 4.54-4.44 (m, 1H), 4.31 (d, J=5.1 Hz, 3H), 4.13 (dd, J=7.1, 10.3 Hz, 1H), 3.83 (s, 3H), 3.42 (q, J=6.0 Hz, 2H), 2.93 (br. s., 1H), 2.71-2.56 (m, 4H), 2.31 (br. s., 2H), 2.19 (s, 3H), 2.03-1.83 (m, 2H), 1.64 (br. s., 1H), 1.53 (d, J=6.9 Hz, 3H), 1.32 (d, J=11.1 Hz, 1H), 1.02 (d, J=10.3 Hz, 1H), 0.65 (d, J=11.8 Hz, 1H).

The compounds shown in the following table were prepared according to the general procedure outlined in this Example using the appropriate starting materials. The structures of the compounds are shown in FIG. 1.

| Compound Number | Name | $^1$H NMR | m/z |
| --- | --- | --- | --- |
| 352 | (R or S)-1-(1-(1-(2-hydroxy-2-methylpropyl)piperidin-4-yl)ethyl)-N-((4-methoxy-6-methyl-2-oxo-1,2-dihydropyridin-3-yl)methyl)-2-methyl-1H-indole-3-carboxamide | NMR (400 MHz, DMSO-d6) δ 11.58 (br. s., 1 H), 7.76-7.65 (m, 2 H), 7.58 (d, J = 7.8 Hz, 1 H), 7.10-6.99 (m, 2 H), 6.14 (s, 1 H), 4.31 (d, J = 4.9 Hz, 2 H), 4.14 (br. s., 1 H), 3.94 (s, 1 H), 3.83 (s, 3 H), 3.56 (s, 2 H), 3.01 (d, J = 11.4 Hz, 1 H), 2.73-2.64 (m, 1 H), 2.59 (s, 3 H), 2.19 (s, 3 H), 2.16-2.03 (m, 2 H), 1.52 (d, J = 6.9 Hz, 4 H), 1.34 (br. s., 2 H), 1.02 (d, J = 4.5 Hz, 7 H), 0.66-0.58 (m, 1 H) | 509 |
| 369 | (R or S)-N-((4,6-dimethyl-2-oxo-1,2-dihydropyridin-3-yl)methyl)-1-(1-(1-(2-hydroxy-2-methylpropyl)piperidin-4-yl)ethyl)-2-methyl-1H-indole-3-carboxamide | (400 MHz, DMSO-d6) δ 11.59 (br. s., 1 H), 7.77-7.69 (m, 1 H), 7.60 (br. s., 2 H), 7.06 (br. s., 2 H), 5.89 (s, 1 H), 4.31 (t, J = 5.7 Hz, 2 H), 4.20-4.09 (m, 1 H), 4.00-3.92 (m, 1 H), 3.58-3.55 (m, 2 H), 3.19-3.10 (m, 1 H), 3.07-2.95 (m, 1 H), 2.74-2.63 (m, 1 H), 2.59 (br. s., 3 H), 2.27 (s, 3 H), 2.12 (s, 3 H), 1.89-1.72 (m, 1 H), 1.54 (br. s., 4 H), 1.30-1.14 (m, 2 H), 1.03 (br. s., 6 H), 0.84-0.57 (m, 2 H) | 493 |

-continued

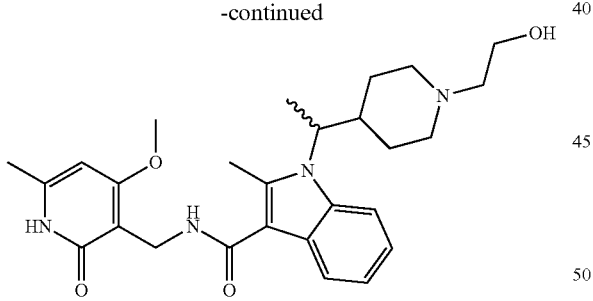

Example 6

Synthesis of (R or S)—N-((4-methoxy-6-methyl-2-oxo-1,2-dihydropyridin-3-yl)methyl)-2-methyl-6-phenyl-1-(1-(tetrahydro-2H-pyran-4-yl)ethyl)-1H-indole-3-carboxamide (Compound 374)

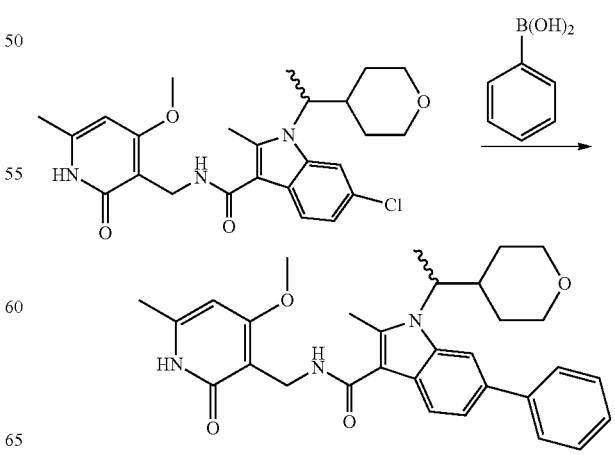

A 25 mL reaction tube was charged with a magnetic stir bar, phenyl boronic acid (72.6 mg, 0.596 mmol), K$_3$PO$_4$ (103 mg, 0.447 mmol), X-Phos pre-catalyst (Chloro(2-dicyclohexylphosphino-2',4',6'-triisopropyl-1,1'-biphenyl)[2-(2-aminoethyl)phenyl)]palladium(II)) (4.92 mg, 5.96 µmol), and the vial was sealed. The vial was evacuated/backfilled with nitrogen (3×) before the addition of methyl 6-chloro-2-methyl-1-(1-(tetrahydro-2H-pyran-4-yl)ethyl)-1H-indole-3-carboxylate (Compound 314) (100 mg, 0.298 mmol) as a solution in 1,4-dioxane (1 mL). The vial was then heated to 100° C. overnight with stirring. The vial was then allowed to cool to room temperature and the reaction concentrated in vacuo. The crude residue was purified via SiO$_2$ chromatography (10 g) using an eluent of ethyl acetate/hexanes (4:1) the title compound as a white solid (106 mg, 0.281 mmol, 94% yield).). LCMS 514 (M+1)$^+$; $^1$H NMR $^1$H NMR (400 MHz, DMSO-d$_6$) δ=11.59 (s, 1H), 7.98-7.84 (m, 2H), 7.75-7.67 (m, 3H), 7.47 (t, J=7.8 Hz, 2H), 7.39 (d, J=8.5 Hz, 1H), 7.35-7.27 (m, 1H), 6.15 (s, 1H), 4.35 (d, J=4.9 Hz, 2H), 4.25-4.12 (m, 1H), 3.93 (d, J=8.5 Hz, 1H), 3.86-3.77 (m, 3H), 3.67 (d, J=8.5 Hz, 1H), 3.39-3.32 (m, 1H), 3.10-3.00 (m, 1H), 2.62 (s, 3H), 2.21 (s, 3H), 1.85 (d, J=10.0 Hz, 1H), 1.63-1.49 (m, 4H), 1.45-1.33 (m, 1H), 1.20-0.99 (m, 1H), 0.66 (d, J=12.0 Hz, 1H).

Example 7

Synthesis of (R or S)-2-(4-(1-(3-((4-methoxy-6-methyl-2-oxo-1,2-dihydropyridin-3-yl)methylcarbamoyl)-2-methyl-1H-indol-1-yl)ethyl)piperidin-1-yl) acetic acid (Compound 364)

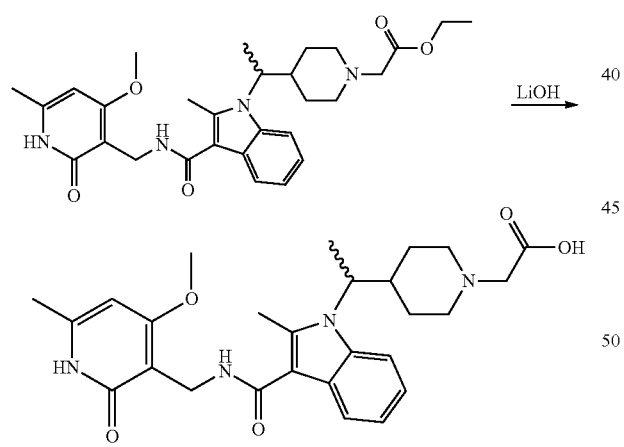

To a round bottomed flask was charged with a magnetic stir bar was added (R or S)-ethyl-2-(4-(1-(3-((4-methoxy-6-methyl-2-oxo-1,2-dihydropyridin-3-yl)methylcarbamoyl)-2-methyl-1H-indol-1-yl)ethyl)piperidin-1-yl)acetate (Compound 363) (69 mg, 0.132 mmol), THF (1.5 mL), MeOH (1.5 mL), and water (0.75 mL). To this solution was added lithium hydroxide monohydrate (5.54 mg, 0.132 mmol) and the reaction stirred at room temperature for 1 h. The organics were removed under reduced pressure and the resulting aqueous solution purified via reverse phase-HPLC (water/MeCN) 0→95% to afford the title compound (66 mg, 0.108 mmol, 82% yield). LCMS 514 (M+1)$^+$ $^1$H NMR (400 MHz, DMSO-d$_6$) δ=11.67 (s, 1H), 9.65 (s, 1H), 7.84-7.68 (m, 2H), 7.63 (d, J=7.4 Hz, 1H), 7.14-7.03 (m, 2H), 6.18 (s, 1H), 4.33 (d, J=3.6 Hz, 2H), 4.27-4.15 (m, 1H), 4.04 (br. s., 2H), 3.85 (s, 3H), 3.57 (s, 1H), 3.35-3.23 (m, 1H), 3.14-2.99 (m, 1H), 2.86-2.74 (m, 1H), 2.62 (s, 3H), 2.21 (s, 3H), 2.18-2.08 (m, 1H), 1.75 (s, 1H), 1.60-1.49 (m, 4H), 1.46-1.33 (m, 1H), 0.92-0.81 (m, 1H).

Example 8

Synthesis of (R or S)-methyl 2-methyl-6-(pyridin-3-yl)-1-(1-(tetrahydro-2H-pyran-4-yl)ethyl)-1H-indole-3-carboxylate This intermediate was used as an alternate starting material in Step 7 set forth in Example 1 for the synthesis of other compounds of the invention.

(R or S)-methyl 2-methyl-1-(1-(tetrahydro-2H-pyran-4-yl)ethyl)-6-(4,4,5,5-tetramethyl-1,3,2-dioxaborolan-2-yl)-1H-indole-3-carboxylate

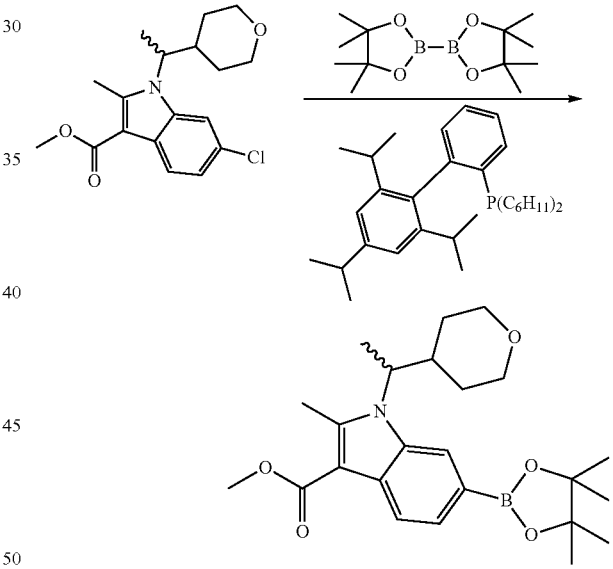

To a round bottomed flask was added Pd(OAc)$_2$ (10.03 mg, 0.045 mmol), potassium acetate (219 mg, 2.233 mmol), 4,4,4',4',5,5,5',5'-octamethyl-2,2'-bi(1,3,2-dioxaborolane) (567 mg, 2.233 mmol), and 2-dicyclohexylphosphino-2',4',6'-triisopropylbiphenyl (XPhos) (85 mg, 0.179 mmol), and the vial was sealed. To this vessel was added (R or S)-methyl 6-chloro-2-methyl-1-(1-(tetrahydro-2H-pyran-4-yl)ethyl)-1H-indole-3-carboxylate (Step 6) (500 mg, 1.489 mmol) dissolved in dioxane (3.4 mL) and the reaction evacuated/back-filled with N$_2$ (3×) before heating to 100° C. overnight. The reaction was then allowed to cool to rt and was diluted with EtOAc. The reaction was filtered through diatomaceous earth and the filtrate concentrated to afford the title compound which was used in subsequent reactions without further purification. LCMS 428 (M+1)$^+$.

(R or S)-methyl 2-methyl-6-(pyridin-3-yl)-1-(1-(tetrahydro-2H-pyran-4-yl)ethyl)-1H-indole-3-carboxylate

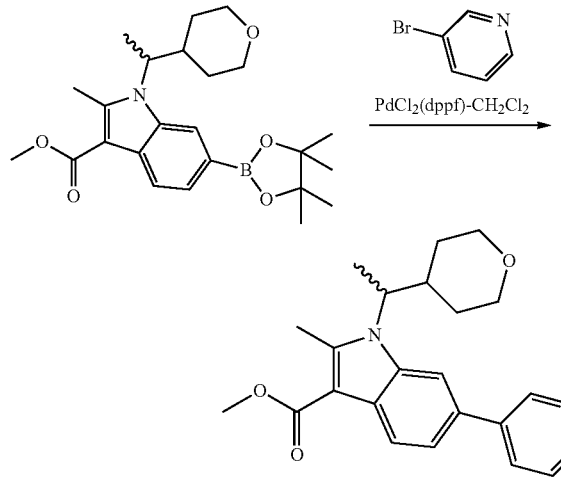

To a re-sealable vial was added K₂CO₃ (206 mg, 1.488 mmol), PdCl₂(dppf)-CH₂Cl₂ adduct (60.8 mg, 0.074 mmol), and the vial was sealed. This vial was evacuated/backfilled with N₂ (3×) before addition of (R or S)-methyl 2-methyl-1-(1-(tetrahydro-2H-pyran-4-yl)ethyl)-6-(4,4,5,5-tetramethyl-1,3,2-dioxaborolan-2-yl)-1H-indole-3-carboxylate (318 mg, 0.744 mmol) dissolved in 1,4-dioxane (4 mL), 3-bromopyridine (71.7 μl, 0.744 mmol), and water (400 μL). The reaction was evacuated/backfilled with N₂ (3×) before heating to 100° C. The solution was cooled to room temperature and diluted with EtOAc. The solution was filtered and concentrated in vacuo. The crude residue was purified via silica gel chromatography (10 g, EtOAc/hex (1:1)) to afford the title compound (101 mg, 0.267 mmol, 35.9% yield). LCMS 379 (M+1)⁺.

Example 9

Other Alkyl Carboxylate Intermediates

The following alkyl carboxylate intermediates were synthesized in an analogous manner to that set forth in Step 2 of Example 1, using an appropriate starting material and reactant.

| Name | Structure | m/z |
|---|---|---|
| (±)-ethyl 5-fluoro-1-(1-methoxypropan-2-yl)-2-methyl-1H-indole-3-carboxylate | 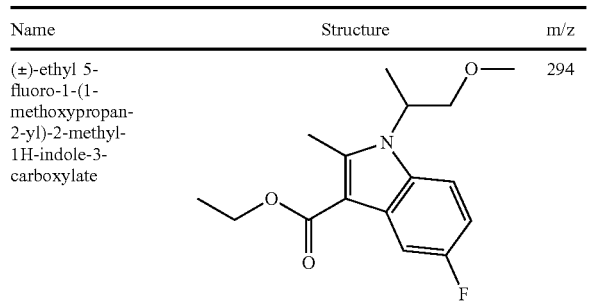 | 294 |
| (±)-ethyl 6-fluoro-1-(1-methoxypropan-2-yl)-2-methyl-1H-indole-3-carboxylate | 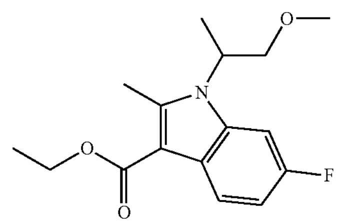 [SMILES: CCOC(=O)c1c(C)n(C(C)COC)c2cc(F)ccc12] | 294 |
| (±)-ethyl 1-(1-methoxypropan-2-yl)-2-methyl-1H-indole-3-carboxylate | 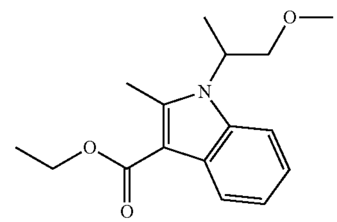 [SMILES: CCOC(=O)c1c(C)n(C(C)COC)c2ccccc12] | 276 |
| (±)-tert-butyl 1-(1-methoxypropan-2-yl)-2-methyl-1H-pyrrolo[2,3-b]pyridine-3-carboxylate | 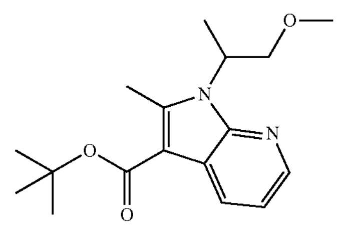 [SMILES: COCC(C)n1c(C)c(C(=O)OC(C)(C)C)c2cccnc21] | 305 |
| (±)-tert-butyl 1-(1-ethoxypropan-2-yl)-2-methyl-1H-pyrrolo[2,3-b]pyridine-3-carboxylate | 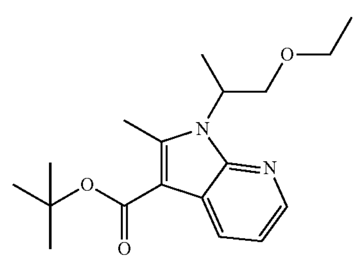 [SMILES: CCOCC(C)n1c(C)c(C(=O)OC(C)(C)C)c2cccnc21] | 319 |
| tert-butyl 1-(3-methoxybutan-2-yl)-2-methyl-1H-pyrrolo[2,3-b]pyridine-3-carboxylate | 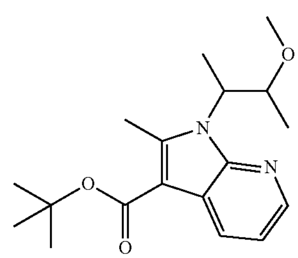 [SMILES: COC(C)C(C)n1c(C)c(C(=O)OC(C)(C)C)c2cccnc21] | 319 |
| ethyl 1-(3-methoxybutan-2-yl)-2-methyl-6-(methylsulfonyl)-1H-indole-3-carboxylate | 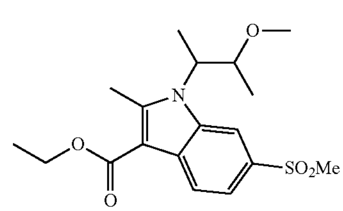 [SMILES: CCOC(=O)c1c(C)n(C(C)C(C)OC)c2cc(S(C)(=O)=O)ccc12] | 368 |

| Name | Structure | m/z |
|---|---|---|
| (±)-ethyl 1-(3-methoxypentan-2-yl)-2-methyl-1H-indole-3-carboxylate | 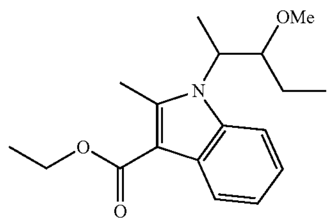 [SMILES: CCOC(=O)c1c(C)n(C(C)C(CC)OC)c2ccccc12] | 304 |

Example 10

Other Compounds of the Invention Produced from Carboxylic Acid Intermediates The following compounds were synthesized in an analogous manner to that set forth in Step 4 of Example 1, using an appropriate starting material. Structures of these compounds are set forth in FIG. 1.

| Compound | Name | $^1$H NMR | m/z |
|---|---|---|---|
| 304 | (±)-1-(1-(4,4-difluorocyclohexyl)ethyl)-N-((4-methoxy-6-methyl-2-oxo-1,2-dihydropyridin-3-yl)methyl)-2-methyl-1H-indole-3-carboxamide | (CDCl$_3$, 400 MHz) δ 12.63-12.64 (d, J = 3.2 Hz, 1H), 7.84 (s, 1H), 7.49 (s, 1H), 7.42-7.40 (d, J = 9.2 Hz, 1H), 7.06-7.00 (m, 2H), 5.90-5.89 (d, J = 3.6 Hz 1H), 4.66-4.62 (t, J = 14 Hz, 2H), 4.11-4.08 (m, 1H), 3.88-3.87 (d, J = 3.6 Hz, 3H), 2.99-2.76 (m, 3H), 2.36 (s, 1H), 2.25 (s, 3H), 2.17-2.16 (d, J = 3.2 Hz, 2H), 2.08-2.05 (m, 2H), 1.84-1.70 (m, 2H), 1.61 (s, 1H), 1.51-1.47 (m, 2H) | 427 |
| 230 | (±)-5-fluoro-N-((4-methoxy-6-methyl-2-oxo-1,2-dihydropyridin-3-yl)methyl)-1-(1-methoxypropan-2-yl)-2-methyl-1H-indole-3-carboxamide | (400 MHz, CD$_3$OD) δ 7.59-7.55 (m, 1H), 7.42-7.39 (m, 1H), 6.95-6.90 (m, 2H), 4.57 (s, 2H), 4.12 (s, 3H), 3.99-3.94 (m, 1H), 3.72-3.65 (m, 1H), 3.19 (s, 3H), 2.64 (s, 3H), 2.54 (s, 3H), 1.59-1.57 (d, 3H) | 416 |
| 231 | (±)-6-fluoro-N-((4-methoxy-6-methyl-2-oxo-1,2-dihydropyridin-3-yl)methyl)-1-(1-methoxypropan-2-yl)-2-methyl-1H-indole-3-carboxamide | (400 MHz, CD$_3$OD) δ 7.70-7.66 (m, 1H), 7.36-7.33 (m, 1H), 6.94-6.89 (m, 2H), 4.56 (s, 2H), 4.11 (s, 3H), 3.97-3.92 (m, 1H), 3.71-3.67 (m, 1H), 3.20 (s, 3H), 2.62 (s, 3H), 2.53 (s, 3H), 1.58-1.56 (d, 3H) | 416 |
| 218 | (±)-N-((4-methoxy-6-methyl-2-oxo-1,2-dihydropyridin-3-yl)methyl)-1-(1-methoxypropan-2-yl)-2-methyl-1H-indole-3-carboxamide | (400 MHz, CD$_3$OD) δ 7.69 (d, J = 7.2 Hz, 1H), 7.53 (d, J = 7.6 Hz, 1H), 7.12 (m, 2H), 6.26 (s, 1H), 4.80 (m, 1H), 4.52 (s, 2H), 3.99 (m, 4H), 3.75 (m, 1H), 3.20 (s, 3H), 2.62 (s, 3H), 2.31 (s, 3H), 1.59 (d, J = 7.2 Hz, 3H) | 398 |
| 183 | (±)-N-((4,6-dimethyl-2-oxo-1,2-dihydropyridin-3-yl)methyl)-1-(1-methoxypropan-2-yl)-2-methyl-1H-indole-3-carboxamide | (400 MHz, CD$_3$OD) δ 7.74 (m, 1H), 7.57 (d, J = 7.6 Hz, 1H), 7.15 (m, 2H), 6.14 (s, 1H), 4.86 (m, 1H), 4.55 (s, 2H), 4.02 (m, 1H), 3.77 (m, 1H), 3.22 (s, 3H), 2.65 (s, 3H), 2.43 (s, 3H), 2.26 (s, 3H), 1.62 (d, J = 7.2 Hz, 3H) | 382 |
| 204 | (±)-N-((4-methoxy-6-methyl-2-oxo-1,2-dihydropyridin-3-yl)methyl)-1-(1-methoxypropan-2-yl)-2-methyl-1H-pyrrolo[2,3-b]pyridine-3-carboxamide | (400 MHz, CDCl$_3$) δ 13.23 (s, 1H), 8.16-8.17 (m, 1H), 8.11-8.13 (m, 1H), 7.57-7.60 (t, J = 5.2 Hz, 1H), 6.93-6.96 (m, 1H), 5.92 (s, 1H), 4.82-4.83 (d, J = 2.4 Hz, 1H), 4.65-4.66 (d, J = 6.4 Hz, 2H), 3.89 (s, 3H), 3.81-3.85 (m, 1H), 3.22 (s, 3H), 2.79 (s, 3H), 2.17 (s, 3H), 1.64-1.66 (d, J = 8.0 Hz, 3H) | 399 |
| 211 | (±)-1-(1-cyclopropylethyl)-N-((4,6-dimethyl-2-oxo-1,2-dihydropyridin-3-yl)methyl)-2-methyl-1H-pyrrolo[2,3-b]pyridine-3-carboxamide | | 379 |
| 212 | (±)-1-(1-ethoxypropan-2-yl)-N-((4-methoxy-6-methyl-2-oxo-1,2-dihydropyridin-3-yl)methyl)-2-methyl-1H-pyrrolo[2,3-b]pyridine-3-carboxamide | (400 MHz, CDCl$_3$) δ 8.173-8.189 (m, 1H), 8.13-8.153 (m, 1H), 7.563 (s, 1H), 6.977-7.008 (m, 1H), 5.938 (s, 1H), 4.652-4.667 (d, 2H), 4.177 (s, 1H), 3.309-3.454 (m, 2H), 3.94-3.98 (m, 1H), 2.806 (s, 3H), 2.212 (s, 3H), 1.665-1.682 (d, 3H), 1.044 (t, 3H) | 413 |
| 235 | (±)-N-((4-ethoxy-6-methyl-2-oxo-1,2-dihydropyridin-3-yl)methyl)-1-(1- | (400 MHz, CDCl$_3$) δ 12.5 (s, 1H), 8.11-8.18 (m, 2H), 7.60 (s, 1H), 6.95-6.98 (m, 1H), 5.90 (s, 1H), 5.96 (s, 1H), 4.83 (s, 1H), 4.10-4.21 (m, 3H), | 413 |

| Compound | Name | ¹H NMR | m/z |
|---|---|---|---|
| | methoxypropan-2-yl)-2-methyl-1H-pyrrolo[2,3-b]pyridine-3-carboxamide | 3.82-3.83 (m, 1H), 3.23 (s, 3H), 3.79 (s, 3H), 2.15 (s, 3H), 1.65-1.66 (d, J = 6.8 Hz, 6H), 1.44-1.47 (t, J = 7.2 Hz, 3H). | |
| 241 | N-((4,6-dimethyl-2-oxo-1,2-dihydropyridin-3-yl)methyl)-1-(3-methoxybutan-2-yl)-2-methyl-1H-pyrrolo[2,3-b]pyridine-3-carboxamide | (400 MHz, CD₃OD): δ 8.67-8.65 (d, 1H), 8.45-8.44 (d, 1H), 7.59-7.55 (m, 1H), 6.70 (s, 1H), 4.79 (s, 1H), 4.61 (s, 2H), 4.07 (s, 1H), 3.32 (s, 3H), 2.75 (s, 3H), 2.56 (s, 3H), 2.42 (s, 3H), 1.68-1.66 (d, 3H), 1.16-1.15 (d, 3H). | 397 |
| 280 | (±)-N-((6-ethyl-4-methoxy-2-oxo-1,2-dihydropyridin-3-yl)methyl)-1-(1-methoxypropan-2-yl)-2-methyl-1H-pyrrolo[2,3-b]pyridine-3-carboxamide | ¹H NMR (400 MHz, CD₃OD) δ 8.25-8.29 (m, 2H). δ 7.28-7.31 (m, 1H). 6.89 (s, 1H), 4.93-4.95 (br, 1H), 4.58 (s, 2H), 4.2-4.25 (m, 1H), 4.13 (s, 3H), 3.77-3.81 (m, 1H), 3.24 (s, 3H), 2.79-2.84 (q, 1H), 2.72 (s, 3H), 1.66-1.68 (d, J = 7.2 Hz, 3H) 1.32-1.36 (t, 3H) | 413 |
| 288 | (R or S)-N-((4-Methoxy-6-methyl-2-oxo-1,2-dihydropyridin-3-yl)methyl)-2-methyl-1-(1-(tetrahydro-2H-pyran-4-yl)ethyl)-1H-pyrrolo[2,3-b]pyridine-3-carboxamide | (400 MHz, d6-DMSO) δ 11.57-11.65 (m, 1H), 8.18-8.23 (m, 1H), 8.07-8.12 (m, 1H), 7.83-7.91 (m, 1H), 7.07-7.15 (m, 1H), 6.15 (s, 1H), 4.31 (d, J = 4.46 Hz, 1H), 4.04-4.20 (m, 1H), 3.88-3.97 (m, 1H), 3.84 (s, 3H), 3.59-3.70 (m, 1H), 2.97-3.10 (m, 1H), 2.79-2.93 (m, 1H), 2.67 (br. S., 3H), 2.20 (s, 3H), 1.78-1.88 (m, 1H), 1.53-1.68 (m, 3H), 1.28-1.41 (m, 3H), 0.97-1.13 (m, 2H), 0.56-0.68 (m, 1H) | 439 |
| 306 | (R or S)-N-((4,6-dimethyl-2-oxo-1,2-dihydropyridin-3-yl)methyl)-2-methyl-1-(1-(tetrahydro-2H-pyran-4-yl)ethyl)-1H-indole-3-carboxamide | (400 MHz, DMSO-d₆) δ = 11.73-11.56 (m, 1 H), 8.19 (d, J = 3.1 Hz, 1 H), 8.06 (dd, J = 1.4, 7.9 Hz, 1 H), 7.82 (br. S., 1 H), 7.10 (dd, J = 4.7, 7.8 Hz, 1 H), 5.91 (s, 1 H), 4.30 (br. S., 2 H), 4.19-4.02 (m, 1 H), 3.90 (d, J = 8.5 Hz, 1 H), 3.63 (d, J = 7.8 Hz, 1 H), 3.29 (s, 1 H), 3.06 (s, 1 H), 2.92-2.74 (m, 1 H), 2.64 (br. S., 3 H), 2.25 (s, 3 H), 2.11 (s, 3 H), 1.80 (br. S., 1 H), 1.59 (br. S., 3 H), 1.41-1.24 (m, 1 H), 1.09 (s, 2 H), 0.67-0.52 (m, 1 H) | 423 |
| 277 | (±)-1-(3-methoxy-3-methylbutan-2-yl)-N-((4-methoxy-6-methyl-2-oxo-1,2-dihydropyridin-3-yl)methyl)-2-methyl-1H-indole-3-carboxamide | (400 MHz, DMSO-d₆) δ = 12.01-11.82 (m, 1 H), 7.91-7.82 (m, 2 H), 7.71-7.64 (m, 1 H), 7.06-6.96 (m, 2 H), 6.25 (s, 1 H), 4.43 (q, J = 7.1 Hz, 1 H), 4.33 (br. S., 2 H), 3.86 (s, 3 H), 3.14-3.09 (m, 3 H), 2.61 (s, 3 H), 2.23 (s, 3 H), 1.58-1.52 (m, 3 H), 1.27 (s, 3 H), 0.88 (s, 3 H) | 426 |
| 275 | (±)-N-((4,6-dimethyl-2-oxo-1,2-dihydropyridin-3-yl)methyl)-1-(3-methoxypentan-2-yl)-2-methyl-1H-indole-3-carboxamide | | 410 |
| 294 | (±)-N-((4-methoxy-6-methyl-2-oxo-1,2-dihydropyridin-3-yl)methyl)-1-(3-methoxybutan-2-yl)-2-methyl-1H-indole-3-carboxamide | (CDCl₃, 400 MHz) δ 7.85 (t, J = 6.4 Hz, 1H), 7.45 (s, 2H), 7.08-7.03 (m, 2H), 5.93 (s, 1H), 4.71-4.61 (m, 2H), 4.36 (s, 1H), 3.90 (s, 4H), 2.95 (s, 3H), 2.75 (s, 3H), 2.17 (s, 3H), 1.57 (d, J = 7.2 Hz, 3H), 1.23 (d, J = 6.0 Hz, 3H) | 412 |
| 290 | (±)-1-(3-ethoxybutan-2-yl)-N-((4-methoxy-6-methyl-2-oxo-1,2-dihydropyridin-3-yl)methyl)-2-methyl-1H-indole-3-carboxamide | (400 MHz, DMSO-d₆) δ = 11.60 (br. s., 1 H), 7.72 (d, J = 7.6 Hz, 1 H), 7.67 (d, J = 5.1 Hz, 2 H), 7.09-6.98 (m, 2 H), 6.14 (s, 1 H), 4.41-4.35 (m, 1 H), 4.32 (d, J = 4.9 Hz, 2 H), 4.03-3.93 (m, 1 H), 3.83 (s, 3 H), 3.25 (d, J = 9.4 Hz, 1 H), 2.82-2.72 (m, 1 H), 2.62 (br. s., 3 H), 2.19 (s, 3 H), 1.52 (d, J = 7.1 Hz, 3 H), 1.15 (d, J = 6.0 Hz, 3 H), 0.68 (t, J = 6.9 Hz, 3 H) | 426 |
| 293 | N-((4-methoxy-6-methyl-2-oxo-1,2-dihydropyridin-3-yl) methyl)-1-(3-methoxypentan-2-yl)-2-methyl-1H-pyrrolo [2,3-b] pyridine-3-carboxamide | (400 MHz, CDCl₃): δ 8.19-8.13 (m, 2H), 7.57-7.55 (t, 1H), 6.99-6.96 (m, 1H), 5.94 (s, 1H), 4.67-4.65 (m, 2H), 4.40 (m, 1H), 4.16 (m, 1H), 3.16 (s, 3H), 2.80 (s, 3H), 2.77 (s, 3H), 2.20 (s, 3H), 1.87-1.81 (m, 1H), 1.67-1.65 (m, 3H), 1.53-1.45 (m, 3H), 1.02-0.99 (m, 3H) | 427 |

| Compound | Name | ¹H NMR | m/z |
|---|---|---|---|
| 299 | N-((4-methoxy-6-methyl-2-oxo-1,2-dihydropyridin-3-yl)methyl)-1-(3-methoxypentan-2-yl)-2-methyl-1H-indole-3-carboxamide | (400 MHz, CDCl$_3$) δ 7.87-7.86 (d, 1H), 7.52-7.45 (m, 2H), 7.10-7.02 (m, 2H), 4.72-4.64 (dd, 2H), 4.45-4.42 (s 1H), 3.9 (s, 3H), 3.73 (s, 1H), 2.8-2.7 (d, 6H), 2.17 (s, 3H), 1.80-1.75 (m, 1H), 1.58 (s, 3H), 1.25 (m, 1H), 1.03-0.99 (t, 3H) | 425 |

Example 11

Synthesis of Methyl 1-(1-(1,4-dioxan-2-yl)ethyl)-2-methyl-1H-indole-3-carboxylate The title compound was used as an alternate alkyl carboxylate starting material in Step 3 of Example 1.

Step 1: 1-(1,4-dioxan-2-yl)ethanone

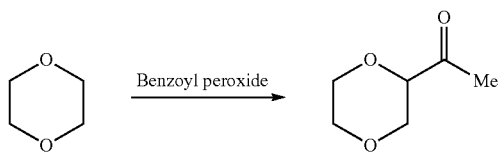 [SMILES: C1COCCO1 ; CC(=O)C1COCCO1]

To a solution of benzoic peroxide (20 g, 141 mmol) in 200 mL 1,4-dioxane at room temperature under nitrogen atmosphere was added biacetyl (24.3 g, 282 mmol). After the addition, the mixture was heated to reflux and stirred for 24 hours. The reaction mixture was cooled to 0° C. The pH was adjusted to around 9 by progressively adding 2N sodium hydroxide below 0° C., extracted with 2-methoxy-2-methylpropane (10 mL×3), and concentrated to give 1-(1,4-dioxan-2-yl)ethanone (13 g, 36%) as a yellow oil which was used directly in the next step without purification.

Step 2: 1-(1,4-dioxan-2-yl)ethanamine

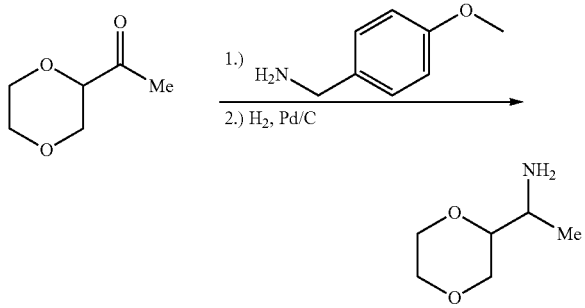

To a solution of 1-(1,4-dioxan-2-yl)ethanone (12 g, 92.2 mmol) in 1,2-dichloroethane (100 mL) was added (4-methoxyphenyl)methanamine (25 g, 184.4 mmol) at room temperature. The mixture was allowed to stir for 3 hours, and then sodium triacetoxyborohydride (39 g, 184.4 mmol) was added. The resulting mixture was allowed to stir for 48 hours at room temperature. The reaction mixture was quenched by adding water, extracted with dichloromethane (100 mL×3). The combined organic phase was dried by anhydrous sodium sulphate, and then filtered. The filtrate was concentrated and purified by column chromatograph on silica gel (elute: dichloromethane/methanol 100:1→50:1→20:1) to give 1-(1,4-dioxan-2-yl)-N-(4-methoxybenzyl) ethanamine (16.4 g, 71%) as a yellow solid. LCMS (M+H⁺) m/z: calcd. 251.15. found 251.9. To a solution of 1-(1,4-dioxan-2-yl)-N-(4-methoxybenzyl)ethanamine (5 g, 19.9 mmol) in anhydrous methanol (100 mL) was added palladium 10% on carbon (240 mg, 2 mmol), then purged with hydrogen (30 psi), the mixture was allowed to stir overnight at room temperature. The reaction mixture was filtered, and the filtrate was concentrated to afford the title compound (2.5 g, 96%) as a brown solid.

The amine intermediates shown in the following table were prepared according to the general procedure outlined above using the appropriate starting materials and modifications.

| Name | Structure | m/z |
|---|---|---|
| tert-butyl 3-(1-aminoethyl)piperidine-1-carboxylate | 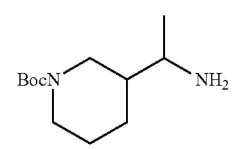 [SMILES: CC(N)C1CCCN(C(=O)OC(C)(C)C)C1] | 228 |
| (±)-1-(4,4-difluorocyclohexyl)ethanamine | 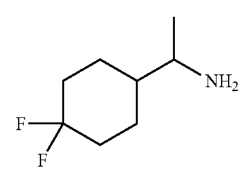 | 164 |
| (±)-1-(1-(methylsulfonyl)azetidin-3-yl)ethanamine | 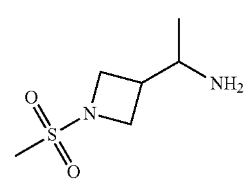 | 179 |
| (±)-tert-butyl 4-(4-(1-aminoethyl)4yridine-2-yl)piperazine-1-carboxylate | | 307 |

Step 3: (E)-methyl 3-((1-(1,4-dioxan-2-yl)ethyl)imino)-2-(2-bromophenyl)butanoate

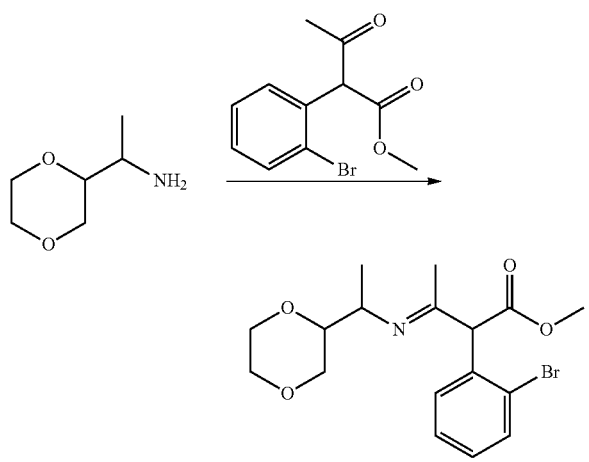

To a solution of 1-(1,4-dioxan-2-yl)ethanamine (2.5 g, 19 mmol) in methanol (100 mL) was added methyl 2-(2-bromophenyl)-3-oxobutanoate (5.4 g, 20 mmol) and acetic acid (1.8 g, 30 mmol). The resulting reaction system was warm to reflux and allowed to stir overnight. The reaction mixture was concentrated and purified by column chromatographed on silica gel (eluted: dichloromethane/methanol 50:1→20:1→5:1) the title compound (1 g, 14%) as a brown solid. LCMS (M+H$^+$) m/z: calcd. 383.07. found 384.9.

The imino-bromo intermediates shown in the following table were prepared according to the general procedure outlined above using the appropriate starting materials (e.g., one of the amines set forth in the table in Step 2 of this example) and modifications.

| Name | Structure | m/z |
|---|---|---|
| (E)-tert-butyl 3-(1-((3-(2-bromophenyl)-4-methoxy-4-oxobutan-2-ylidene)amino)ethyl)piperidine-1-carboxylate | | 482 |
| (±)-(E)-methyl 2-(2-bromophenyl)-3-((1-(4,4-difluorocyclohexyl)ethyl)imino)butanoate | | 417 |
| (E)-tert-butyl 4-((3-(2-bromophenyl)-4-methoxy-4-oxobutan-2-ylidene)amino)piperidine-1-carboxylate | | 454 |
| (Z)-methyl 2-(2-bromophenyl)-3-(quinolin-5-ylamino)but-2-enoate | 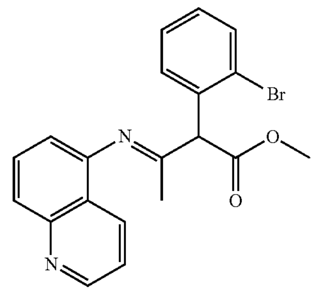 [SMILES: COC(=O)C(/C(C)=N/c1cccc2ncccc12)c1ccccc1Br] | 398 |
| (E)-methyl 2-(2-bromophenyl)-3-(cyclopentylimino)butanoate | 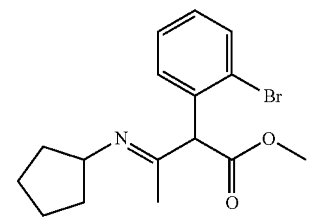 [SMILES: COC(=O)C(/C(C)=N/C1CCCC1)c1ccccc1Br] | 339 |
| (E)-methyl 2-(2-bromophenyl)-3-((6-methylquinolin-5-yl)imino)butanoate | 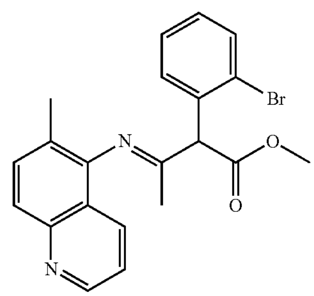 [SMILES: COC(=O)C(/C(C)=N/c1c(C)ccc2ncccc12)c1ccccc1Br] | 412 |
| (±)-(E)-methyl 2-(2-bromophenyl)-3-((1-(1-(methylsulfonyl)azetidin-3-yl)ethyl)imino)butanoate | 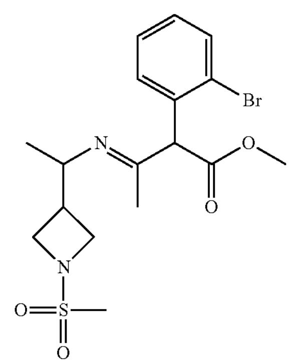 [SMILES: COC(=O)C(/C(C)=N/C(C)C1CN(S(C)(=O)=O)C1)c1ccccc1Br] | 432 |
| (±)-(E)-tert-butyl 4-(4-((3-(2-bromophenyl)-4-methoxy-4-oxobutan-2-ylidene)amino)pyridine-2-yl)piperazine-1-carboxylate | 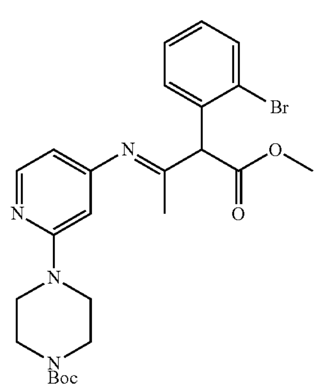 [SMILES: COC(=O)C(/C(C)=N/c1ccnc(N2CCN(C(=O)OC(C)(C)C)CC2)c1)c1ccccc1Br] | 559 |

| Name | Structure | m/z |
|---|---|---|
| (E)-methyl 2-(2-bromophenyl)-3-((2,5-dimethylphenyl)amino)but-2-enoate | 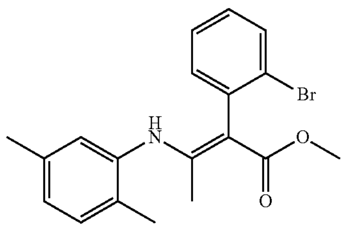 | 375 |
| (E)-methyl 2-(2-bromophenyl)-3-((2,3-dimethylphenyl)amino)but-2-enoate | 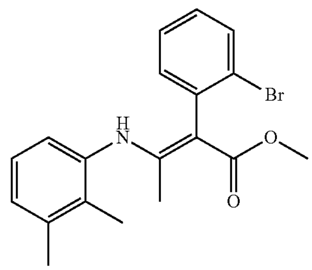 [SMILES: COC(=O)/C(=C(\C)Nc1cccc(C)c1C)c1ccccc1Br] | 375 |
| (E)-methyl 2-(2-bromophenyl)-3-(quinolin-6-ylimino)butanoate | 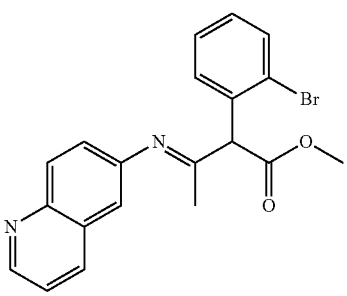 [SMILES: COC(=O)C(/C(C)=N/c1ccc2ncccc2c1)c1ccccc1Br] | 398 |

Step 4: Methyl 1-(1-(1,4-dioxan-2-yl)ethyl)-2-methyl-1H-indole-3-carboxylate

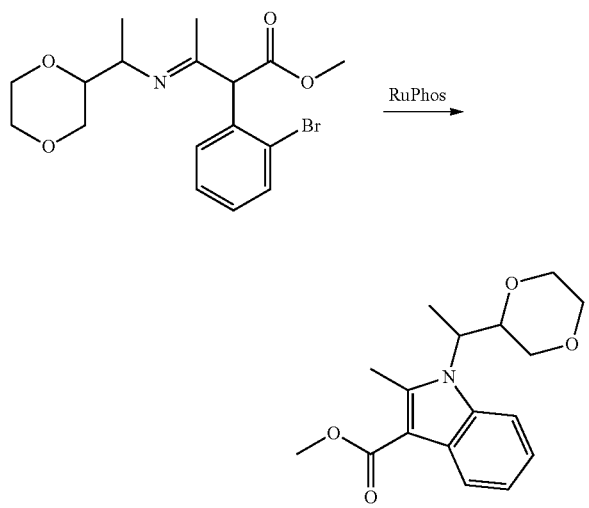

To a solution of (E)-methyl 3-((1-(1,4-dioxan-2-yl)ethyl)imino)-2-(2-bromophenyl)butanoate (400 mg, 1.1 mmol) in dioxane (3 mL) was added Chloro[2-(dicyclohexylphosphino)-3,6-dimethoxy-2',4',6'-triisopropylbiphenyl][2-(2-aminoethyl)phenyl]Pd(II) (160 mg, 0.2 mmol), 2-Dicyclohexyphosphino-2',6'-diisopropoxybiphenyl (93 mg, 0.2 mmol) and sodium tert-butoxide (192 mg, 2 mmol). The resulting reaction mixture was heated to 120° C. with stirring for 30 mins in a microwave. The reaction mixture was quenched by adding water and was extracted with ethyl acetate (25 mL×3). The combined organic phase was dried by anhydrous sodium sulphate, and then filtered. The filtrate was concentrated and purified by column chromatograph on silica gel (eluted: petrol ether/acetic ester 10:1→5:1→2:1) to afford the title compound (282 mg, 89%) as yellow solid. LCMS (M+H$^+$) m/z: calcd. 303.15. found 303.9.

The compound shown in the following table was prepared according to the general procedure outlined above using the appropriate starting materials (e.g., one of the imino-bromo intermediates shown in the table in Step 3 of this example) and modifications.

| Name | Structure | m/z |
|---|---|---|
| (±)-methyl 1-(1-(4,4-difluorocyclohexyl)ethyl)-2-methyl-1H-indole-3-carboxylate | 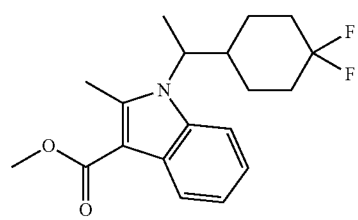 [SMILES: COC(=O)c1c(C)n(C(C)C2CCC(F)(F)CC2)c2ccccc12] | 336 |

These alkyl carboxylates were also used as starting material in Step 3 of Example 1 in the synthesis of certain compounds of the invention.

Example 12

Chiral Separation of Compound 219 to Afford Compounds 223 and 224

N-((4-methoxy-6-methyl-2-oxo-1,2-dihydropyridin-3-yl)methyl)-1-(1-methoxypropan-2-yl)-2-methyl-1H-indole-3-carboxamide (200 mg) (Compound 219) was subjected to chiral chromatography via supercritical fluid chromatography (SFC) (A: C$_2$H$_5$OH, B: NH$_3$—H$_2$O. A:B=55:45 AD column) to afford the separate enantiomers 223 (peak 1) and 224 (Peak 2) (60 mg each) LCMS 398 (M+1)$^+$ $^1$H NMR (400 MHz, CD$_3$OD) δ 7.69 (d, J=7.2 Hz, 1H), 7.53 (d, J=7.6 Hz, 1H), 7.12 (m, 2H), 6.26 (s, 1H), 4.80 (m, 1H), 4.52 (s, 2H), 3.99 (m, 4H), 3.75 (m, 1H), 3.20 (s, 3H), 2.62 (s, 3H), 2.31 (s, 3H), 1.59 (d, J=7.2 Hz, 3H). The optical rotation of each enantiomer was not determined.

The compounds shown in the following table were prepared according to the general chiral chromatography procedure outlined above. The optical rotation of the separated enantiomers was not determined, but the elution peak ("Peak 1" or "Peak 2") is indicated. Structures of each compound are shown in FIG. 1.

| Compound | Name | ¹H NMR | m/z |
|---|---|---|---|
| 217 | (R or S)-N-((4,6-dimethyl-2-oxo-1,2-dihydropyridin-3-yl)methyl)-1-(1-methoxypropan-2-yl)-2-methyl-1H-indole-3-carboxamide-PEAK 1 | (400 MHz, CD₃OD) δ 7.74 (m, 1H), 7.57 (d, J = 7.6 Hz, 1H), 7.15 (m, 2H), 6.14 (s, 1H), 4.86 (m, 1H), 4.55 (s, 2H), 4.02 (m, 1H), 3.77 (m, 1H), 3.22 (s, 3H), 2.65 (s, 3H), 2.43 (s, 3H), 2.26 (s, 3H), 1.62 (d, J = 7.2 Hz, 3H) | 382 |
| 218 | (R or S)-N-((4,6-dimethyl-2-oxo-1,2-dihydropyridin-3-yl)methyl)-1-(1-methoxypropan-2-yl)-2-methyl-1H-indole-3-carboxamide-PEAK 2 | (400 MHz, CD₃OD) δ 7.74 (m, 1H), 7.57 (d, J = 7.6 Hz, 1H), 7.15 (m, 2H), 6.14 (s, 1H), 4.86 (m, 1H), 4.55 (s, 2H), 4.02 (m, 1H), 3.77 (m, 1H), 3.22 (s, 3H), 2.65 (s, 3H), 2.43 (s, 3H), 2.26 (s, 3H), 1.62 (d, J = 7.2 Hz, 3H) | 382 |
| 252 | (R or S)-(±)-1-(1-cyclopropylethyl)-N-((4,6-dimethyl-2-oxo-1,2-dihydropyridin-3-yl)methyl)-2-methyl-1H-pyrrolo[2,3-b]pyridine-3-carboxamide PEAK 1 | NMR (400 MHz, CDCl₃): δ 8.32-8.34 (d, 1H), 8.18-8.2 (d, 1H), 7.27-7.30 (m, 1H), 6.70 (s, 1H), 4.47 (s, 2H), 3.94-3.95 (d, 1H), 2.61 (s, 3H), 2.43 (s, 3H), 2.29-2.30 (s, 3H), 1.57-1.59 (d, 3H), 0.63-0.64 (t, 1H), 0.27-0.64 (m, 2H), 0.02-0.04 (t, 1H) | 379 |
| 253 | (R or S)-(±)-1-(1-cyclopropylethyl)-N-((4,6-dimethyl-2-oxo-1,2-dihydropyridin-3-yl)methyl)-2-methyl-1H-pyrrolo[2,3-b]pyridine-3-carboxamide PEAK 2 | NMR (400 MHz, CDCl₃): δ 8.32-8.34 (d, 1H), 8.18-8.2 (d, 1H), 7.27-7.30 (m, 1H), 6.70 (s, 1H), 4.47 (s, 2H), 3.94-3.95 (d, 1H), 2.61 (s, 3H), 2.43 (s, 3H), 2.29-2.30 (s, 3H), 1.57-1.59 (d, 3H), 0.63-0.64 (t, 1H), 0.27-0.64 (m, 2H), 0.02-0.04 (t, 1H) | 379 |
| 256 | (R or S)-N-((4-methoxy-6-methyl-2-oxo-1,2-dihydropyridin-3-yl)methyl)-1-(1-methoxypropan-2-yl)-2-methyl-1H-pyrrolo[2,3-b]pyridine-3-carboxamide PEAK 1 | (400 MHz, CDCl₃) δ 13.23 (s, 1H), 8.16-8.17 (m, 1H), 8.11-8.13 (m, 1H), 7.57-7.60 (t, J = 5.2 Hz, 1H), 6.93-6.96 (m, 1H), 5.92 (s, 1H), 4.82-4.83 (d, J = 2.4 Hz, 1H), 4.65-4.66 (d, J = 6.4 Hz, 2H), 3.89 (s, 3H), 3.81-3.85 (m, 1H), 3.22 (s, 3H), 2.79 (s, 3H), 2.17 (s, 3H), 1.64-1.66 (d, J = 8.0 Hz, 3H) | 399 |
| 257 | (R or S)-N-((4-methoxy-6-methyl-2-oxo-1,2-dihydropyridin-3-yl)methyl)-1-(1-methoxypropan-2-yl)-2-methyl-1H-pyrrolo[2,3-b]pyridine-3-carboxamide PEAK 2 | (400 MHz, CDCl₃) δ 13.23 (s, 1H), 8.16-8.17 (m, 1H), 8.11-8.13 (m, 1H), 7.57-7.60 (t, J = 5.2 Hz, 1H), 6.93-6.96 (m, 1H), 5.92 (s, 1H), 4.82-4.83 (d, J = 2.4 Hz, 1H), 4.65-4.66 (d, J = 6.4 Hz, 2H), 3.89 (s, 3H), 3.81-3.85 (m, 1H), 3.22 (s, 3H), 2.79 (s, 3H), 2.17 (s, 3H), 1.64-1.66 (d, J = 8.0 Hz, 3H) | 399 |
| 307 | Trans-(R or S, R or S)-N-((4-methoxy-6-methyl-2-oxo-1,2-dihydropyridin-3-yl)methyl)-1-(3-methoxybutan-2-yl)-2-methyl-1H-indole-3-carboxamide PEAK 1 | (CDCl₃, 400 MHz) δ 7.85 (t, J = 6.4 Hz, 1H), 7.45 (s, 2H), 7.08-7.03 (m, 2H), 5.93 (s, 1H), 4.71-4.61 (m, 2H), 4.36 (s, 1H), 3.90 (s, 4H), 2.95 (s, 3H), 2.75 (s, 3H), 2.17 (s, 3H), 1.57 (d, J = 7.2 Hz, 3H), 1.23 (d, J = 6.0 Hz, 3H) | 412 |
| 308 | Trans-(R or S, R or S)-N-((4-methoxy-6-methyl-2-oxo-1,2-dihydropyridin-3-yl)methyl)-1-(3-methoxybutan-2-yl)-2-methyl-1H-indole-3-carboxamide PEAK 2 | (CDCl₃, 400 MHz) δ 7.85 (t, J = 6.4 Hz, 1H), 7.45 (s, 2H), 7.08-7.03 (m, 2H), 5.93 (s, 1H), 4.71-4.61 (m, 2H), 4.36 (s, 1H), 3.90 (s, 4H), 2.95 (s, 3H), 2.75 (s, 3H), 2.17 (s, 3H), 1.57 (d, J = 7.2 Hz, 3H), 1.23 (d, J = 6.0 Hz, 3H) | 412 |

Example 1

Synthesis of tert-butyl 1-(2,3-dihydro-1H-inden-1-yl)-2-methyl-1H-pyrrolo[2,3-b]pyridine-3-carboxylate The title compound as starting material in Step 3 of Example 36 in the synthesis of certain compounds of the invention.

Tert-butyl 2-methyl-1H-pyrrolo[2,3-b]pyridine-3-carboxylate

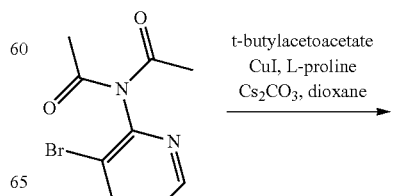

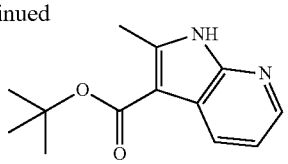

To a 500 mL round-bottom flask that contains N-acetyl-N-(3-bromopyridin-2-yl)acetamide (14.815 g, 57.6 mmol), was added copper(I) iodide (1.098 g, 5.76 mmol), L-proline (1.327 g, 11.53 mmol), cesium carbonate (28.2 g, 86 mmol), then t-butyl acetoacetate (11.47 ml, 69.2 mmol) and dioxane (100 mL). The reaction was vac/purged with $N_2$ 3× then fitted with a septum and a $N_2$ inlet and heated overnight at 70° C. The inorganic solids were removed by filtration over celite and the cake was washed with 100 mL EtOAc. This solution was concentrated and the residue was partitioned between 250 mL brine and 250 mL EtOAc. The aq. Layer was further extracted with EtOAc (2×250 mL) and the combined organic layer was dried over $Na_2SO_4$, filtered, concentrated and purified by CC using 1:1 EtOAc:Hex as eluent to provide (2.7 g, 20.2%) of tert-butyl 2-methyl-1H-pyrrolo[2,3-b]pyridine-3-carboxylate. LRMS (M+H$^+$) m/z: calc'd 233.28. found 233.1.

Tert-butyl 1-(2,3-dihydro-1H-inden-1-yl)-2-methyl-1H-pyrrolo[2,3-b]pyridine-3-carboxylate

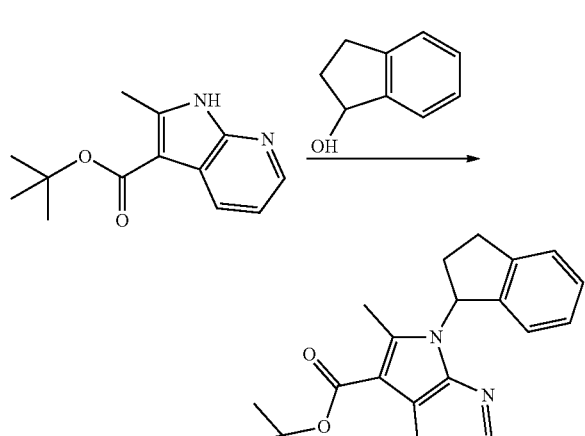

A solution of ethyl tert-butyl 2-methyl-1H-pyrrolo[2,3-b]pyridine-3-carboxylate (100 mg, 0.74 mmol), 2,3-dihydro-1H-inden-1-ol (176 mg, 0.74 mmol), $PPh_3$ (195 mg, 1.49 mmol) was stirred in dry THF (10 mL) at 0° C. under a nitrogen atmosphere. To this mixture was added drop-wise DIAD (150 mg, 1.48 mmol) over a period of 5 min, and the reaction was stirred at room temperature for 16 hours. The mixture was washed with brine, dried and concentrated to afford the crude product. The crude product was purified by silca gel chromatography (petroleum ether/ethyl acetate=5:1) to afford the tert-butyl-1-(2,3-dihydro-1H-inden-1-yl)-2-methyl-1H-pyrrolo[2,3-b]pyridine-3-carboxylate (150 mg, 60%).

The compound shown in the following table was prepared according to the general procedure outlined above using the appropriate starting materials and modifications.

| Name | Structure | m/z |
|---|---|---|
| (±)-tert-butyl 1-(1-cyclopropylethyl)-2-methyl-1H-pyrrolo[2,3-b]pyridine-3-carboxylate | 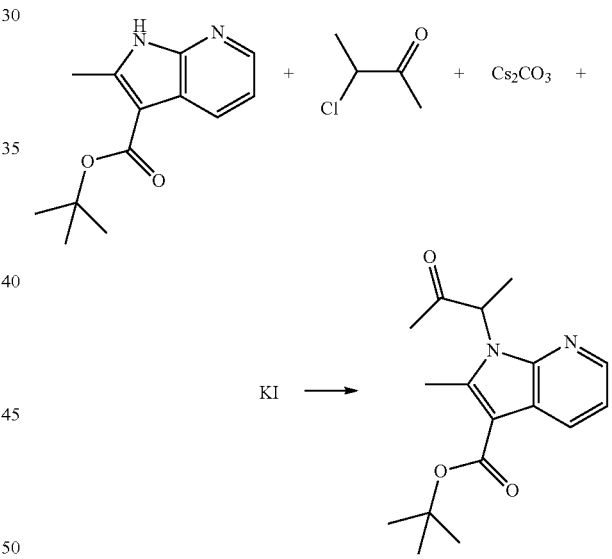 | 301 |

Each of the above alkyl carboxylates was used as starting material in Step 3 of Example 1 in the synthesis of certain compounds of the invention.

Example 13

Synthesis of isolated N-((4-methoxy-6-methyl-2-oxo-1,2-dihydropyridin-3-yl)methyl)-1-((2R or 2S, 3R or 3S)-3-methoxybutan-2-yl)-2-methyl-1H-pyrrolo[2,3-b]pyridine-3-carboxamide diastereomers (Compounds 261, 266, 267 and 302)

Step 1: Tert-butyl 2-methyl-1-(3-oxobutan-2-yl)-1H-pyrrolo[2,3-b]pyridine-3-carboxylate To a solution of tert-butyl 2-methyl-1H-pyrrolo[2,3-b]pyridine-3-carboxylate (5.0 g, 21.53 mmol) in $CH_3CN$ (50 mL) was added $Cs_2CO_3$ (21.0 g, 64.58 mmol), potassium iodide (3.57 g, 21.53 mmol). The mixture was stirred at 27° C. for 30 minutes. Then 3-chlorobutan-2-one (2.75 g, 25.83 mmol) was added and the mixture was stirred at 70° C. for 12 hours. The mixture was filtered and the filtrate was concentrated. The residue was purified by column (Elute: Petroleum ether:Ethyl acetate=50:1) to give tert-butyl 2-methyl-1-(3-oxobutan-2-yl)-1H-pyrrolo[2,3-b]pyridine-3-carboxylate as a yellow-green oil. (3.23 g, yield 50%) LCMS (M+H$^+$) m/z: calcd 303.37. found 302.9. 1H NMR (400 MHz, CDCl$_3$): δ 8.32-8.30 (m, 1H), 8.25-8.23 (m, 1H), 7.17-7.14 (m, 1H), 5.50-5.44 (m, 1H), 2.71 (s, 3H), 1.96 (s, 3H), 1.65-1.67 (d, 3H), 1.64 (s, 9H).

Step 2: Tert-butyl 1-(3-hydroxybutan-2-yl)-2-methyl-1H-pyrrolo[2,3-b]pyridine-3-carboxylate

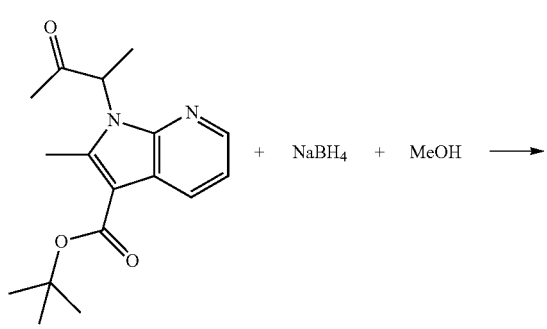    + NaBH₄ + MeOH ⟶

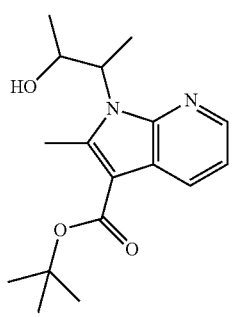

To the solution of tert-butyl 2-methyl-1-(3-oxobutan-2-yl)-1H-pyrrolo[2,3-b]pyridine-3-carboxylate (3.1 g, 10.25 mmol) in methanol (30 mL) was added sodium borohydride (0.30 g, 8.2 mmol) at 0° C. After 30 minutes, another batch of sodium borohydride (0.30 g, 8.2 mmol) was added at 0° C. After the reaction completed about 2 h later, water (30 ml) was added dropwise very carefully to quench the reaction. The mixture was extracted with CH₂Cl₂. The extraction was dried over Na₂SO₄, filtered and concentrated under vacuum to give tert-butyl 1-(3-hydroxybutan-2-yl)-2-methyl-1H-pyrrolo[2,3-b]pyridine-3-carboxylate as a yellow solid. (3.0 g, yield 96%) LCMS (M+H⁺) m/z: calcd 305.38. found 304.9. 1H NMR (400 MHz, CDCl₃): δ 8.31-8.29 (m, 1H), 8.13-8.12 (m, 1H), 7.11-7.07 (m, 1H), 4.46-4.43 (m, 1H), 4.12 (m, 1H), 2.73 (s, 3H), 1.58 (s, 9H), 1.51-1.49 (d, 3H), 0.92-0.91 (d, 3H).

Step 3: Tert-butyl-1-(3-methoxybutan-2-yl)-2-methyl-1H-pyrrolo[2,3-b]pyridine-3-carboxylate

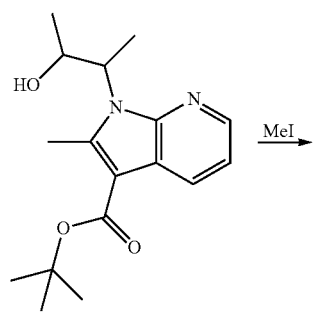  MeI ⟶

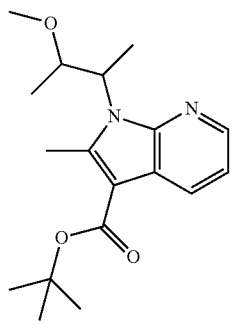

To dry THF (20 mL) was added NaH (60% in mineral oil, 2.37 g, 59.14 mmol). Then the mixture was stirred at 27° C. for 20 minutes, then tert-butyl 1-(3-hydroxybutan-2-yl)-2-methyl-1H-pyrrolo[2,3-b]pyridine-3-carboxylate (3.0 g, 9.86 mmol) was added. The mixture was stirred at 27° C. for 1 hour, then added by CH₃I (13.99 g, 98.6 mmol). The mixture was stirred for 12 hours at 27° C. and then cooled to 0° C. Sat. NH₄Cl was added and extracted with CH₂Cl₂. The extraction was dried over sodium sulfate, filtered and concentrated to give tert-butyl-1-(3-methoxybutan-2-yl)-2-methyl-1H-pyrrolo[2,3-b]pyridine-3-carboxylate as a yellow oil. (3.2 g, yield 100%) LCMS (M+H⁺) m/z: calcd. 319.41. found 318.9.

Step 4: 1-(3-methoxybutan-2-yl)-2-methyl-1H-pyrrolo[2,3-b]pyridine-3-carboxylic acid

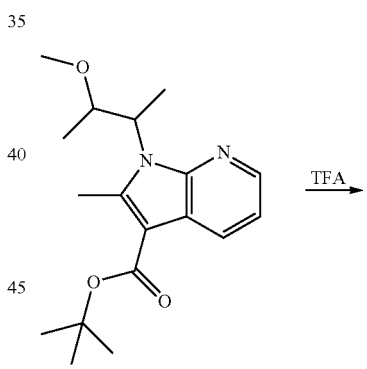  TFA ⟶

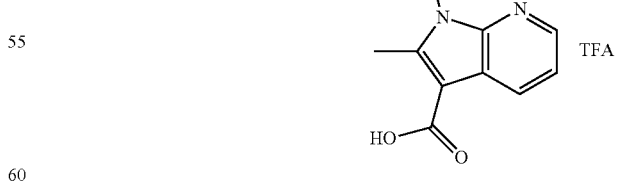

To the pre-cooled solution of tert-butyl 1-(3-methoxybutan-2-yl)-2-methyl-1H-pyrrolo[2,3-b]pyridine-3-carboxylate (3.0 g, 9.42 mmol) in CH₂Cl₂ (20 mL) was added trifluoroacetic acid (20 mL) dropwise. The solution was stirred at 27° C. for 1.5 hours. The solvent was removed under vacuum at 27° C. The residue was used for next step without purified. LCMS (M+H+) m/z: calcd 263.30. found 262.9.

Step 5: N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide

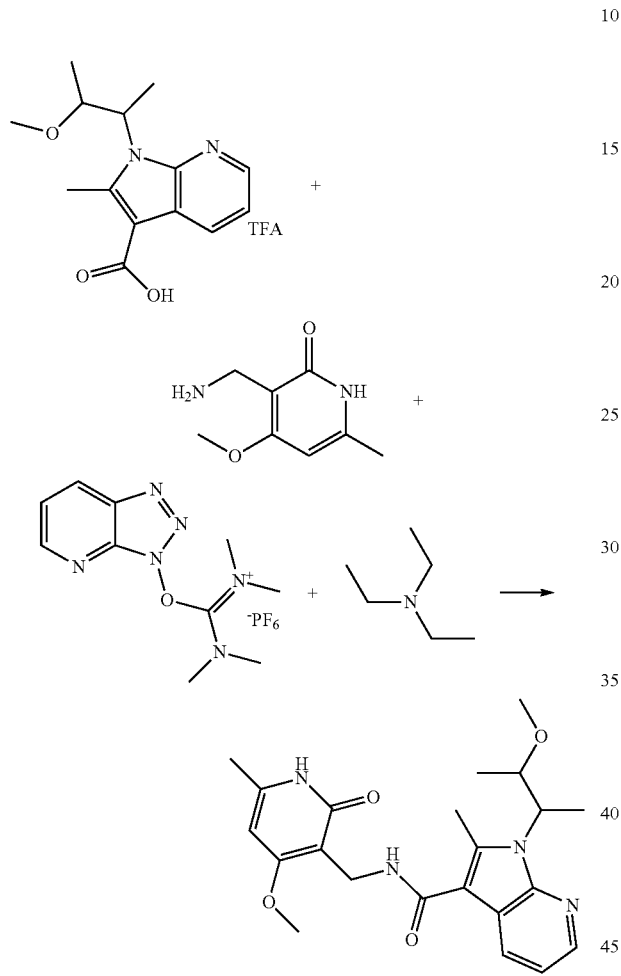

To a solution of 1-(3-methoxybutan-2-yl)-2-methyl-1H-pyrrolo[2,3-b]pyridine-3-carboxylic acid (2.4 g, 9.15 mmol) in DMF (30 mL) was added TEA (4.2 g, 41.50 mmol), 3-(aminomethyl)-4-methoxy-6-methylpyridin-2(1H)-one hydrochloride (2.1 g, 12.81 mmol) After stirred for 10 minutes at 27° C., the mixture was cooled and added HATU (5.56 g, 14.64 mmol). The mixture was stirred at 27° C. for 72 hours and 30% of S.M. remained. Then the mixture was heated at 80° C. for 5 hours. The solution was diluted with brine (100 mL) and extracted with $CH_2Cl_2$ (100 mL*3). The extractions were combined and dried over $Na_2SO_4$. The solvent was evaporated under vacuum and the residue was purified by flash column (Eluent: dichloromethane:methanol=95:5) to give N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide. (3.6 g, yield 95%)

Step 6: Separation of N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide: Isomers (Compounds 261, 266, 267, and 302)

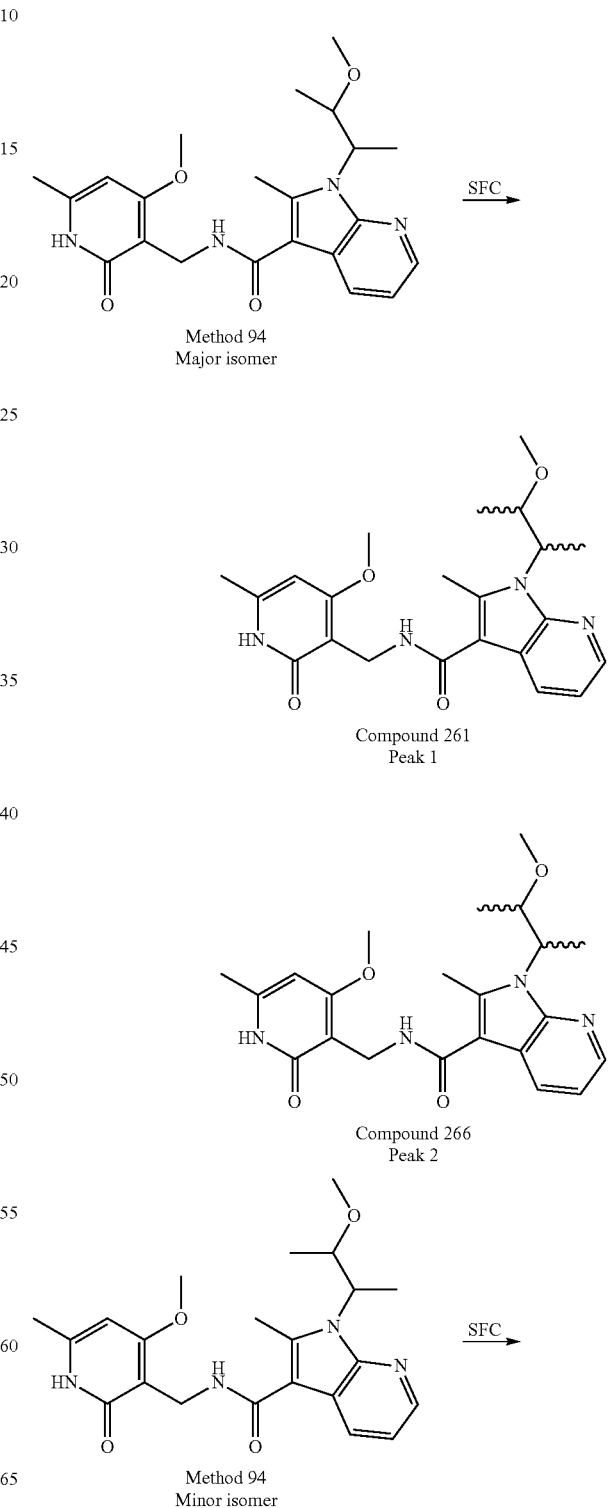

-continued

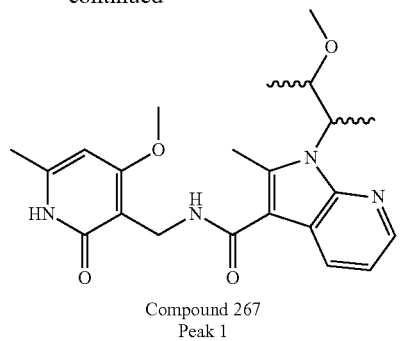

Compound 267
Peak 1

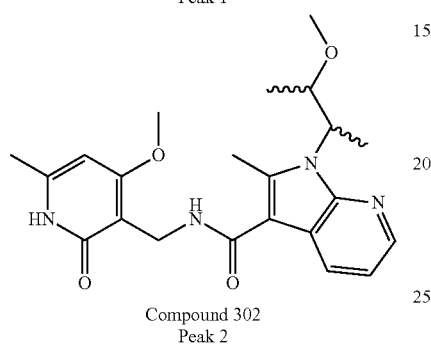

Compound 302
Peak 2

The mixture or isomers from step 5, N-((4-methoxy-6-methyl-2-oxo-1,2-dihydropyridin-3-yl)methyl)-1-(3-methoxybutan-2-yl)-2-methyl-1H-pyrrolo[2,3-b]pyridine-3-carboxamide was purified by prep-HPLC (Condition: Column: SHIMADZU LC-8A, 250*50 mm*10 um; Mobile phase A: water with 0.2% formic acid; Mobile phase B: MeCN; column temperature: 30° C.; Gradient: B in A 10-50%) to give a major isomer pair (Compound 261 and Compound 266 combined) (1.0 g, purity 98.8%) and a minor isomer pair (Compound 267 and Compound 302 combined) (180 mg, purity 63%). The resulting isomer pairs were individually separated by SFC (Condition: Column: Chiralpak AD 250*30 mm*5 um; Mobile phase A: Supercritical $CO_2$; Mobile phase B: IPA+$NH_3.H_2O$; Gradient: B/A: 75:25) to give the following individual single compounds:

Compound 261, N-((4-methoxy-6-methyl-2-oxo-1,2-dihydropyridin-3-yl)methyl)-1-((2R or 2S, 3R or 3S)-3-methoxybutan-2-yl)-2-methyl-1H-pyrrolo[2,3-b]pyridine-3-carboxamide (Major Isomer Pair; Peak 1): $^1$H NMR (400 MHz, $CDCl_3$): δ 8.173-8.157 (m, 1H), 8.140-8.116 (m, 1H), 7.582-7.555 (m, 1H), 6.968-6.936 (m, 1H), 5.927 (s, 1H), 4.707-4.609 (m, 2H), 4.348 (s, 1H), 3.892 (s, 3H), 2.869 (s, 3H), 2.788 (s, 3H), 2.173 (s, 3H), 1.644-1.627 (d, 3H), 1.263-1.249 (d, 3H).

Compound 266, N-((4-methoxy-6-methyl-2-oxo-1,2-dihydropyridin-3-yl)methyl)-1-((2R or 2S, 3R or 3S)-3-methoxybutan-2-yl)-2-methyl-1H-pyrrolo[2,3-b]pyridine-3-carboxamide (Major Isomer Pair; Peak 2): $^1$H NMR (400 MHz, $CDCl_3$): δ 8.179-8.163 (m, 1H), 8.143-8.120 (m, 1H), 7.558-7.531 (m, 1H), 6.986-6.954 (m, 1H), 5.931 (s, 1H), 4.702-4.605 (m, 2H), 3.897 (s, 3H), 2.892 (s, 3H), 2.789 (s, 3H), 2.189 (s, 3H), 1.647-1.629 (d, 3H), 1.267-1.252 (d, 3H).

Compound 267, N-((4-methoxy-6-methyl-2-oxo-1,2-dihydropyridin-3-yl)methyl)-1-((2R or 2S, 3R or 3S)-3-methoxybutan-2-yl)-2-methyl-1H-pyrrolo[2,3-b]pyridine-3-carboxamide (Minor Isomer Pair; Peak 1): $^1$H NMR (400 MHz, $CDCl_3$): δ 8.174-8.162 (d, 1H), 8.111-8.094 (d, 1H), 7.551-7.526 (m, 1H), 6.993-6.961 (m, 1H), 5.935 (s, 1H), 4.683-4.579 (m, 2H), 3.887 (s, 3H), 3.442 (s, 3H), 2.753 (s, 3H), 2.194 (s, 3H), 1.695-1.678 (d, 3H), 0.781-0.768 (d, 3H).

Compound 302, N-((4-methoxy-6-methyl-2-oxo-1,2-dihydropyridin-3-yl)methyl)-1-((2R or 2S, 3R or 3S)-3-methoxybutan-2-yl)-2-methyl-1H-pyrrolo[2,3-b]pyridine-3-carboxamide (Minor Isomer Pair; Peak 2): $^1$H NMR (400 MHz, $CDCl_3$): δ 8.177-8.166 (d, 1H), 8.122-8.104 (d, 1H), 7.587-7.562 (m, 1H), 6.984-6.952 (m, 1H), 5.933 (s, 1H), 4.698-4.591 (m, 2H), 4.426 (s, 2H), 3.983 (s, 3H), 3.448 (s, 3H), 2.764 (s, 3H), 2.180 (s, 3H), 1.701-1.684 (d, 3H), 0.786-0.772 (d, 3H).

Example 14

Synthesis of (±)-N-((4,6-dimethyl-2-oxo-1,2-dihydropyridin-3-yl)methyl)-2-methyl-1-(1-phenylethyl)-1H-pyrrolo[2,3-c]pyridine-3-carboxamide Step 1: 1-(3-methoxyphenyl)ethanol

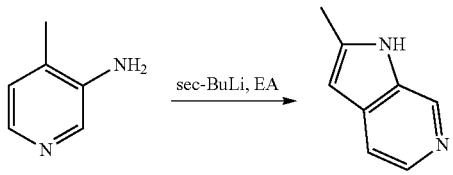

To a stirred solution of 3-Amino-4-picoline (7 g, 64.8 mmol) in anhydrous THF (200 mL), sec-BuLi (150 mL, 1.3M in cyclohexane, 194 mmol) was added dropwise over 20 minutes at −78° C. The solution was warmed to room temperature and stirred at 3 hours. Ethyl acetate (2.3 g, 25.9 mmol) was added dropwise into the reaction at −78° C. and the mixture was stirred at the same temperature for 2 hours. Methanol (50 mL) was added dropwise into the reaction over 10 minutes. The mixture was warmed to room temperature and stirred for 1 hour. A half-saturated NH4Cl (250 mL) was added. The mixture was extracted with EA. The combined organic layers were washed with brine, dried and concentrated to afford the crude product. The crude product was purified by silica gel chromatography (petroleum ether/ethyl acetate=10:1) to afford 2-methyl-1H-pyrrolo[2,3-c]pyridine (2.5 g, 73.5%).

Step 2: 2,2,2-trichloro-1-(2-methyl-1H-pyrrolo[2,3-c]pyridin-3-yl)ethanone

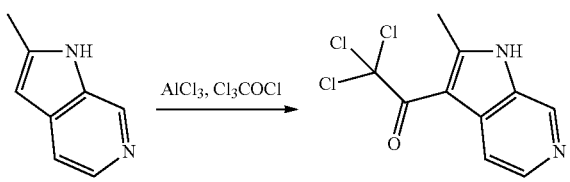

To a stirred solution of 2-methyl-1H-pyrrolo[2,3-c]pyridine (2.5 g, 18.9 mmol) and aluminum chloride (5 g, 37.8 mmol) in DCM (100 mL), trichloroacetylchloride (4.1 g, 22.7 mmol) was added dropwise into the reaction over 0.5 hours at room temperature. After stirring 2 hours, the reaction was cooled to 0° C. and was quenched with water (100 mL). The resulting precipitate was isolated by filtration to afford 2,2,2-trichloro-1-(2-methyl-1H-pyrrolo[2,3-c]pyridin-3-yl) ethanone which was used for next step without further purification. Assumed 100% yield. (5.24 g).

Step 3: Methyl 2-methyl-1H-pyrrolo[2,3-c]pyridine-3-carboxylate

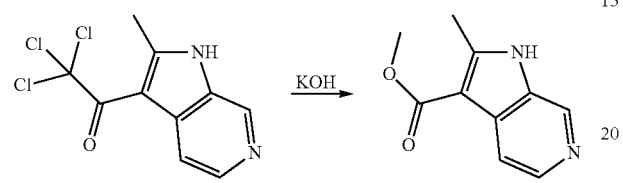

A mixture of 2,2,2-trichloro-1-(2-methyl-1H-pyrrolo[2,3-c]pyridin-3-yl)ethanone (5.24 g, 18.9 mmol) and KOH (1.2 g, 20.9 mmol) in MeOH (100 mL) was stirred at room temperature for 16 hour. The reaction mixture was concentrated to remove MeOH, the residue was partitioned between EA and Water. The organic layer was washed with brine, dried and concentrated to afford methyl 2-methyl-1H-pyrrolo[2, 3-c]pyridine-3-carboxylate (3 g, 83%).

Step 4: Methyl methyl 2-methyl-1-(1-phenylethyl)-1H-pyrrolo[2,3-c]pyridine-3-carboxylate

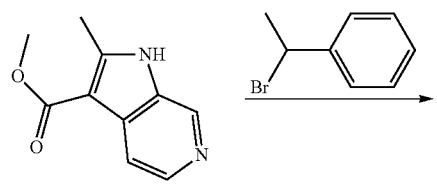

A mixture of methyl 2-methyl-1H-pyrrolo[2,3-c]pyridine-3-carboxylate (550 mg, 2.89 mmol) and sodium hydride (200 mg, 4.34 mmol) in N,N-dimethylformamide (3.0 mL) was stirred at room temperature for 0.5 hour, and then (1-bromoethyl)benzene (589 mg, 3.18 mmol) was added. The mixture was stirred at room temperature for 3 hours. The reaction mixture was poured into saturated NH$_4$Cl and extracted with ethyl acetate. Organic layers were combined and concentrated to give a residue. The residue was purified by chromatography (petroleum ether/ethyl acetate=5:1) to give methyl 2-methyl-1-(1-phenylethyl)-1H-pyrrolo[2,3-c] pyridine-3-carboxylate (800 mg, 94%).

Step 5: 2-methyl-1-(1-phenylethyl)-1H-pyrrolo[2,3-c]pyridine-3-carboxylic acid

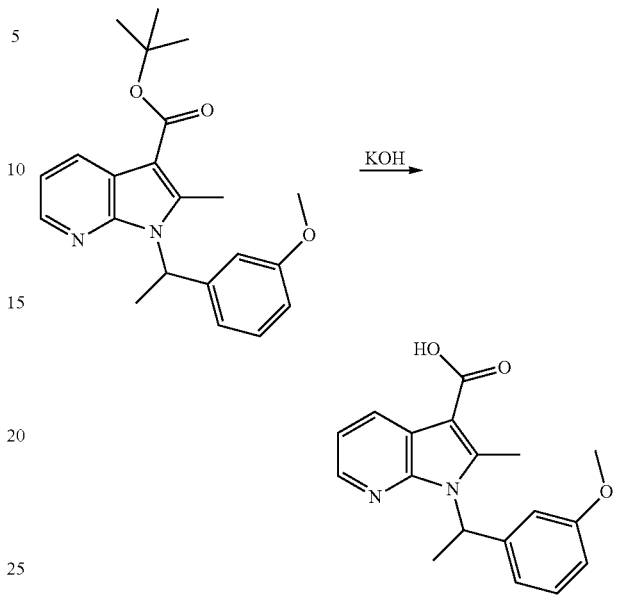

To a mixture of methyl 2-methyl-1-(1-phenylethyl)-1H-pyrrolo[2,3-c]pyridine-3-carboxylate (800 mg, 2.72 mmol) and KOH (1.5 g, 27.2 mmol) in (15 mL) and water (5 mL) was refluxed for 2 hours. The mixture was adjust PH to 2 by 10% HCl and extracted with EA. The combined organic layers were washed with brine, dried and concentrated to afford the crude product. The crude product was used into the next step without more purification. 100% yield. (760 mg).

Step 6: (±)-N-((4,6-dimethyl-2-oxo-1,2-dihydropyridin-3-yl)methyl)-2-methyl-1-(1-phenylethyl)-1H-pyrrolo[2,3-c]pyridine-3-carboxamide (Compound 203)

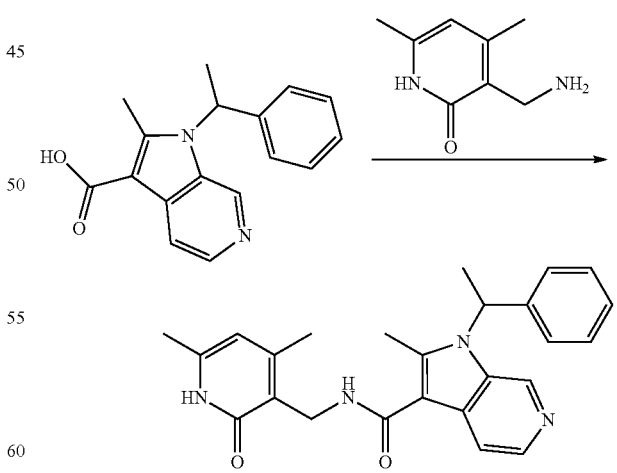

A mixture of 2-methyl-1-(1-phenylethyl)-1H-pyrrolo[2,3-c] pyridine-3-carboxylic acid (280 mg, 1.0 mmol) was added HATU (456 mg, 1.2 mmol), TEA (1 g, 10 mmol) and 3-(aminomethyl)-4,6-dimethylpyridin-2(1H)-one (182 mg, 1.2 mmol) in anhydrous dichloromethane (30 mL) was stirred at room temperature for 16 hours. To the reaction mixture was added water (10 mL), extracted with dichloromethane (30 mL×2). The organic layers were combined and concentrated to give a residue. The residue was rerystallized from MeCN to afford compound N-((4,6-dimethyl-2-oxo-1,2-dihydropyridin-3-yl)methyl)-2-methyl-1-(1-phenylethyl)-1H-pyrrolo[2,3-c]pyridine-3-carboxamide as an off-white solid (80 mg, 21.6%). LRMS (M+H$^+$) m/z: calcd 414.21. found 414. $^1$H NMR (400 MHz, Methanol-d4) δ: 8.84 (s, 1H), 8.16 (d, J=7.6 Hz, 1H), 8.03 (d, J=6.8 Hz, 1H), 7.44-7.37 (m, 5H), 6.09 (s, 1H), 6.01-5.99 (m, 1H), 4.49 (s, 2H), 2.73 (s, 3H), 2.38 (s, 3H), 2.22 (s, 3H), 2.06 (d, J=7.2 Hz, 3H).

The compounds shown in the following table were prepared according to the general procedure outlined in this example using the appropriate starting materials and modifications. Structures are shown in FIG. 1.

| Compound | Name | NMR | m/z |
|---|---|---|---|
| 240 | (±)-N-((4,6-dimethyl-2-oxo-1,2-dihydropyridin-3-yl)methyl)-1-(1-methoxypropan-2-yl)-2-methyl-1H-pyrrolo[2,3-c]pyridine-3-carboxamide | (400 MHz, CHLOROFORM-d) δ ppm 1.63 (br. s., 3 H) 2.21 (s, 3 H) 2.41 (s, 3 H) 2.73 (s, 3 H) 3.24 (s, 3 H) 3.72 (dd, J = 9.81, 5.40 Hz, 1 H) 3.80-3.88 (m, 1 H) 4.60 (d, J = 5.95 Hz, 2 H) 4.71 (dd, J = 13.23, 7.06 Hz, 1 H) 5.92 (s, 1 H) 7.31 (d, J = 5.73 Hz, 1 H) 7.38 (br. s., 1 H) 8.26 (d, J = 5.29 Hz, 1 H) 9.09 (br. s., 1 H) 11.07 (br. s., 1 H) | 383 |
| 243 | (±)-N-((4-methoxy-6-methyl-2-oxo-1,2-dihydropyridin-3-yl)methyl)-2-methyl-1-(1-phenylethyl)-1H-pyrrolo[2,3-c]pyridine-3-carboxamide | (400 MHz, CHLOROFORM-d) δ ppm 1.62 (br. s., 3 H) 2.26 (s, 3 H) 2.75 (s, 3 H) 3.25 (s, 3 H) 3.72 (dd, J = 9.81, 5.40 Hz, 1 H) 3.80-3.87 (m, 1 H) 3.90 (s, 3 H) 4.65 (d, J = 5.29 Hz, 2 H) 4.71 (dd, J = 13.78, 6.95 Hz, 1 H) 5.93 (s, 1 H) 7.32 (br. s., 1 H) 7.50 (br. s., 1 H) 8.25 (br. s., 1 H) 9.11 (br. s., 1 H) | 431 |

Example 15

General Procedures for Synthesizing Other Compounds of the Invention

General Procedure A: Indole Alkyation

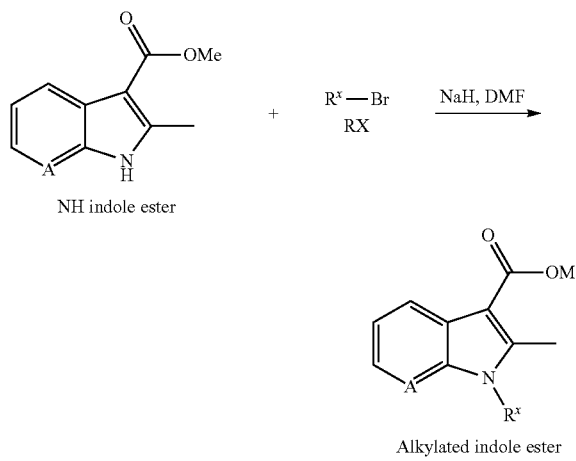

NH indole ester

Alkylated indole ester

To a cooled (0° C.) solution of NH indole ester (1 equivalent) in N,N-dimethylformamide (volume to make concentration 0.4M) was added sodium hydride (60% w/w, 1.1 equivalents relative to indole). The resultant mixture was stirred for 15 minutes. Then RX (2 equivalents) was added and the reaction was allowed to warm to room temperature. The reaction was maintained at ambient temperature for 12 hours. The reaction mixture was poured into saturated ammonium chloride solution (100 mL) with stirring. The mixture was extracted with ethyl acetate (200 mL×2) and the combined organic phase was washed with brine, dried over magnesium sulfate, filtered, and concentrated to give crude product which was purified by column chromatography (silica gel, petroleum ether/ethyl acetate=20:1) to afford the desired alkylated Indole ester product.

General Procedure B: Saponification of Alkylated Indole Ester

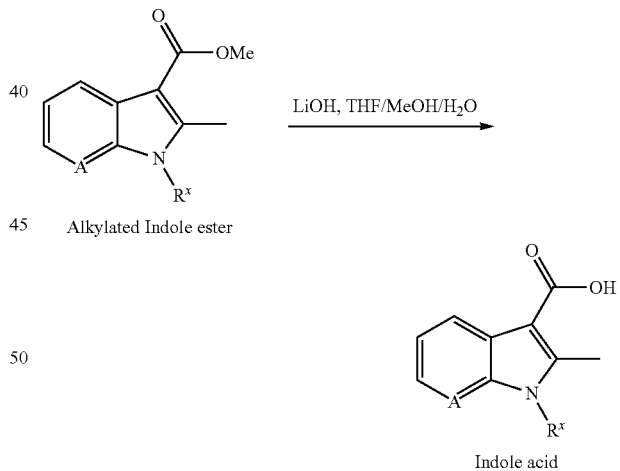

Alkylated Indole ester

Indole acid

To a solution of alkylated Indole ester (1 equivalent) in tetrahydrofuran:methanol:water (2.5:5:1, volume to make concentration 0.05M) was added lithium hydroxide (4 equivalents). The resultant reaction mixture was stirred at 60° C. for 48 hours. The mixture was concentrated in vacuo. Then the residue was diluted with water (40 mL) and slowly acidified with 1N hydrogen chloride to pH=4-5. The mixture was extracted with ethyl acetate (100 mL×3). The combined organic layers were washed with brine, dried over magnesium sulfate, filtered and concentrated to give crude indole acid, which was used in the subsequent step without additional purification.

General Procedure C: Amide Bond Formation

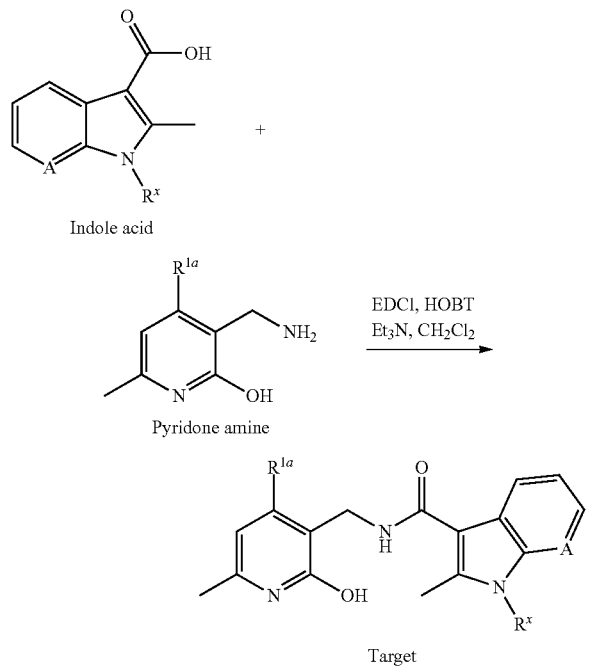

General Procedure L: Sulphonylation

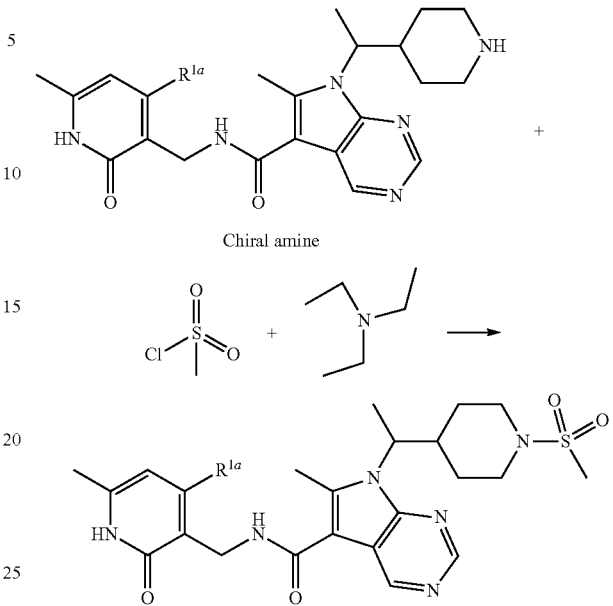

To a solution of Indole acid (1 equivalent) in dichloromethane (volume to make concentration 0.05M) were added 1-hydroxybenzotriazole (1.5 equivalents), 1-(3-dimethylaminopropyl)-3-ethylcarbodiimide hydrochloride (1.5 equiv.) and triethylamine (3 equiv.). The resultant mixture was stirred at room temperature for 30 minutes. Then Pyridone amine (1.2 equiv.) was added and the resultant mixture was stirred at room temperature for 16 hours. Water (50 mL) was added to the mixture. The mixture was extracted with dichloromethane (100 mL×2). The organic layer was concentrated in vacuo to provide crude product which was purified by column chromatography (silica gel, dichloromethane/methanol=20:1) to afford the target compound.

General Procedure D: Chiral Chromatography
Separation of chiral compounds was accomplished via normal phase HPLC or SFC (supercritical carbon dioxide fluid chromatography). Separated compounds were typically>95% ee. The absolute configuration of chiral centers was not determined.

To a solution of Chiral amine (1 equiv.) in dichloromethane (volume to make concentration 0.1M) was added triethylamine (4 equiv.) at 18° C. under $N_2$. The reaction was cooled to 0° C. and methanesulfonyl chloride (1.5 equiv.) was added. The reaction was stirred at 0° C. for 1 h. Then the mixture was concentrated in vacuo and methanol and potassium carbonate were added and the reaction was stirred for another 1 h. The mixture was filtered and the crude product was purified by preparative-HPLC.

The table below lists compounds of the invention and which of the above general methods was used in their synthesis. Structures of these compounds are set forth in FIG. 1.

| Compound | General Methods Used and Notes | Name | NMR data | m/z |
|---|---|---|---|---|
| 370 | General procedure L on (±)-N-((4-methoxy-6-methyl-2-oxo-1,2-dihydropyridin-3-yl)methyl)-6-methyl-7-(1-(piperidin-4-yl)ethyl)-7H-pyrrolo[2,3-d]pyrimidine-5-carboxamide | | $^1$H NMR (CDCl3, 400 MHz) δ 12.12 (s, 1H), 9.20 (s, 1H), 8.78 (s, 1H), 7.68 (s, 1H), 5.97 (s, 1H), 4.70-4.58 (m, 2H), 3.91 (s, 4H), 3.62 (d, J = 12.0 Hz, 1H), 2.76-2.67 (m, 7H), 2.45 (dd, $J_1$ = 2.0 Hz, $J_2$ = 11.6 Hz, 1H), 2.32 (s, 3H), 2.10 (t, J = 12.0 Hz, 1H), 1.67 (d, J = 6.8 Hz, 4H), 1.48-1.40 (m, 1H), 1.37-1.29 (m, 1H), 1.27-1.19 (m, 1H), 0.9-0.78 (m, 1H). | 517 |

Example 16

$IC_{50}$ Measurements for Inhibitors Using EZH2

EZH2 Assay:
Assays were carried out by mixing rPRC2 together with biotinylated oligonucleosome substrates in the presence of the radio-labeled enzyme co-factor, S-adenosyl-L-methionine ($^3$H SAM) (Perkin Elmer) and monitoring the enzymatically mediated transfer of tritiated methyl groups from $^3$H SAM to histone lysine residues. The amount of resulting tritiated methyl histone product was measured by first capturing the biotinylated oligonucleosomes in streptavidin (SAV) coated FlashPlates (Perkin Elmer), followed by a wash step to remove un-reacted $^3$H SAM, and then counting on a TopCount NXT 384 well plate scintillation counter (Perkin Elmer). The final assay conditions for EZH2 were as follows: 50 mM Tris Buffer pH 8.5, 1 mM DTT, 69 μM Brij-35 detergent, 5.0 mM MgCl$_2$, 0.1 mg/mL BSA, 0.2 μM $^3$H SAM, 0.2 μM biotinylated oligonucleosomes, 3.6 μM H3K27me3 peptide and 2 nM EZH2.

Compound IC$_{50}$ measurements were obtained as follows: Compounds were first dissolved in 100% DMSO as 10 mM stock solutions. Ten point dose response curves were generated by dispensing varying amounts of the 10 mM compound solution in 10 wells of the 384 well plate (Echo; Labcyte), pure DMSO was then used to backfill the wells to insure all wells have the same amount of DMSO. A 12.5 μL volume of the HMT enzyme, H3K27me3 peptide and oligonucleosome substrate in assay buffer was added to each well of the assay plate using a Multidrop Combi (Thermo-Fisher). Compounds were pre-incubated with the enzyme for 20 min, followed by initiation of the methyltransferase reaction by addition of 12.5 μL of $^3$H SAM in assay buffer (final volume=25 μL). The final concentrations of compounds ranged from a top default concentration of 80 μM down to 0.16 μM in ten 2-fold dilution steps. Reactions were carried out for 60 minutes and quenched with 20 μL per well of 1.96 mM SAH, 50 mM Tris pH 8.5, 200 mM EDTA. Stopped reactions were transferred to SAV coated Flashplates (Perkin Elmer), incubated for 120 min, washed with a plate washer, and then read on the TopCount NXT (1.0 min/well) to measure the amount of methyl histone product formed during the reaction. The amount of methyl histone product was compared with the amount of product formed in the 0% and 100% inhibition control wells allowing the calculation of % Inhibition in the presence of the individual compounds at various concentrations. IC$_{50}$'s were computed using a 4 parameter fit non-linear curve fitting software package (XLFIT, part of the database package, ActivityBase (IDBS)) where the four parameters were IC$_{50}$, Hill slope, pre-transitional baseline (0% INH), and post-transitional baseline (100% INH); with the latter two parameters being fixed to zero and 100%, respectively, by default.

Assay for Y641N EZH2 was performed as above using reconstituted H3K27Me2 oligonucleosomes as substrate.

Table 2 shows the activity of selected compounds of this invention in the EZH2 and Y641N EZH2 activity inhibition assay. IC$_{50}$ values are reported as follows: "A" indicates an IC$_{50}$ value of less than 100 nM; "B" indicates an IC$_{50}$ value of 100 nM to 1 μM; "C" indicates an IC$_{50}$ value of greater than 1 μM and less than 10 μM for each enzyme; "D" indicates an IC$_{50}$ value of greater than 10 μM for each enzyme; and "*(X μM)" indicates that no inhibition was observed at the highest concentration (i.e., X μM) of compound tested.

TABLE 2

IC50 Values for Compounds of Formula I against EZH2 and Y641N EZH2 Mutant Enzymes.

| Compound No. | EZH2 IC$_{50}$ | Y641N EZH2 IC$_{50}$ |
|---|---|---|
| 183 | A | A |
| 204 | A | B |
| 211 | A | B |
| 212 | A | B |
| 217 | B | B |
| 218 | A | A |
| 219 | A | A |
| 223 | A | B |
| 224 | A | A |
| 229 | C | D |
| 230 | A | B |
| 231 | A | B |
| 234 | C | D |
| 235 | B | C |
| 236 | *(0.5 μM) | *(10 μM) |
| 240 | A | B |
| 241 | A | B |
| 243 | A | B |
| 252 | A | B |
| 253 | A | B |
| 256 | A | B |
| 257 | B | C |
| 261 | A | A |
| 266 | B | B |
| 267 | A | B |
| 273 | A | A |
| 275 | A | A |
| 277 | A | A |
| 280 | B | C |
| 284 | A | B |
| 288 | A | A |
| 290 | A | B |
| 293 | A | B |
| 294 | A | A |
| 298 | A | A |
| 299 | A | A |
| 300 | A | A |
| 302 | B | C |
| 304 | A | A |
| 306 | A | A |
| 307 | A | A |
| 308 | B | B |
| 310 | A | A |
| 313 | A | A |
| 314 | A | A |
| 316 | A | A |
| 317 | A | A |
| 321 | A | A |
| 327 | A | A |
| 335 | A | A |
| 336 | A | A |
| 337 | A | A |
| 341 | A | A |
| 342 | A | A |
| 343 | A | A |
| 344 | A | A |
| 345 | A | A |
| 346 | A | A |
| 347 | A | A |
| 352 | A | A |
| 355 | A | A |
| 356 | A | A |
| 357 | A | A |
| 358 | A | A |
| 359 | A | A |
| 360 | A | A |
| 362 | A | A |
| 363 | A | A |
| 364 | A | B |
| 365 | A | A |
| 366 | A | A |
| 367 | A | A |
| 368 | A | A |
| 369 | A | A |

TABLE 2-continued

IC50 Values for Compounds of Formula I against
EZH2 and Y641N EZH2 Mutant Enzymes.

| Compound No. | EZH2 IC$_{50}$ | Y641N EZH2 IC$_{50}$ |
|---|---|---|
| 370 | A | A |
| 373 | A | A |
| 375 | A | A |
| 376 | A | A |
| 377 | A | A |

Example 17

EC50 Measurements for Inhibitors in HeLa Cell Assays

H3K27me3 MSD Hela Assay.

Trypsinized HeLa cells were counted and diluted in 10% DMEM (Life Technologies, Cat. #10569) to 5000 cells/75 µL. Seventy-five µL of cells were place in each well of a 96-well flat-bottomed plate and incubated at 37° C. for 4 hours. Twenty-five µL of test compound (at various concentrations) was added to the cells and incubation continued at 37° C. for 96 hours. Media was then removed and the cells rinsed once with ice cold PBS. Forty µL of ice-cold MSD Buffer AT (10 mM HEPES, pH 7.9, 5 mM MgCl$_2$, 0.25M sucrose, Benzonase 1:10000), 1% Triton X-100 supplemented with fresh 1× Protease Inhibitor cocktail and 1 mM 4-(2-Aminoethyl)benzenesulfonyl fluoride hydrochloride (AEBSF)) was added to each well and the plates placed on ice for 30 minutes. Ten µL of 5M NaCl was then added to each well and incubation on ice continued for another 15 minutes. The material in each well was suspended pipetting up and down and then transferred to a new 96 well plate. The emptied wells were rinsed with 150 uL ice-cold 20 mM Tris pH 7.5, 1 mM EDTA, 1 mM EGTA, supplemented with fresh 1× Protease Inhibitor cocktail and 1 mM AEBSF ("NO salt NO detergent buffer) and transferred to the respective wells in the new plate. Three hundred µL of NO Salt NO detergent buffer was then added to each well of lysates and the plates frozen at −80° C.

On the same day, an appropriate number of MSD standard bind 96-well plates were coated with 30 µL/well of total H3 capture antibody (Millipore, Cat # MAB3422) at 1 µg/mL concentration in PBS. The antibody solution was evenly distributed first by tapping gently on the sides of the plates and then by shaking the plates for a few minutes at 1000 rpm. Antibody coated plates were stored at 4° C. overnight.

The next day the lysates are thawed to RT. The antibody coated MSD plates are washed 3× with TBS-T (Tris-buffered saline (Fisher Scientific, Cat #BP2471-1)+0.2% Tween-20). One-hundred fifty µL of 5% Blocker A in TBS-T is added to each well. The wells are covered and shaken on a shaker at RT for one hour. The Blocker A step is repeated a second time. After removing the blocker, 25 µL of cell lysate is transferred into each antibody coated well. The plates are shaken for 2 hours at RT, the lysate removed and the plates again washed with Blocker A in TBS-T. Twenty-five µL of appropriate freshly prepared antibody mix (including both primary and secondary antibodies) is added to each well and the plates shaken for 1 hour at RT. The antibody mix used was one (or both) of those indicated in the table below:

| Ab | Concentration (µg/mL) | Primary Ab (µL) | Anti-rabbit detection Ab (µL) | 1% blocker A (µL) |
|---|---|---|---|---|
| H3K27me3 | 33 | 37.88 | 5.00 | 5000 |
| H3 | 12 | 52.08 | 5.00 | 5000 |

Both H3 antibodies were obtained from Cell Signalling (Cat #s 4499 and 9733). The goat anti-rabbit antibody was obtained from Meso-Scale Discovery (Cat #R32AB-1).

The antibody mix was then removed and the wells washed with Blocker A. One hundred-fifty µL of freshly prepared 1×MSD Read Buffer (Meso-Scale Discovery; Cat #R927C-2) was then added to each well and the plates read on a MSD Sector 2400 Plate Reader.

Data was analyzed using Assay Assistant (Constellation Pharmaceuticals In-house product) and Activity Base (IDBS Ltd, Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

H3K27me3 Alpha Hela Assay (AlphaLISA).

Ten different doses of each test compound (in a series of 3-fold dilutions) were plated in duplicate 384-well tissue culture treated plates (Catalog #781080; Greiner Bio One; Monroe, N.C.). Hela cells grown in culture were trypsinized and counted using a Countess® cell counter (Catalog #C10281; Life Technologies, Grand Island, N.Y.). Cell were diluted to 67,000 cells per mL in 10% DMEM (Catalog #10569-010 Life Technologies, Grand Island, N.Y.) and 15 µL (1,000 cells) were plated into each well using the Biotek MicroFlo™ Select Dispenser (BioTek Instruments, Inc. Vermont, USA),) of the 384-well plate. Plates were incubated at 37° C./5% CO$_2$ for 72 hrs. One of the duplicate plates was processed for HeLa assay and the other for viability.

To the plate processed for AlphaLISA was added 5 µL per well Cell-Histone Lysis buffer (1×) (Catalog #AL009F1 Perkin Elmer; Waltham, Mass.) and the plate was incubated at RT for 30 minutes on a plate shaker with low speed (Model #4625-Q Thermo Scientific; Waltham, Mass.). Then, 10 µL per well Histone Extraction buffer (catalog #AL009F2; Perkin Elmer; Waltham, Mass.) was added and the plate further incubated at RT for 20 min on plate shaker with low speed. To each well was then added 10 µL per well of a 5× mix of anti-K27me3 acceptor beads plus Biotinylated anti-Histone H3 (C-ter) Antibody (diluted to 3 nM final) (Catalog #AL118 Perkin Elmer; Waltham, Mass.). Dilution of the acceptor beads and then anti-Histone H3 was with 1× Histone Detection buffer (Catalog #AL009F3 Perkin Elmer; Waltham, Mass.) which was produced diluted from the 10× stock provided. The plate was sealed with an aluminum plate sealer and incubated at 23° C. for 60 min. We then added 10 µL 5× solution of Streptavidin Donor beads (Catalog #6760002 Perkin Elmer; Waltham, Mass.) (20 µg/mL final in 1× Histone Detection Buffer), sealed the plate with Aluminum plate sealer and incubated at 23° C. for 30 min. The plates were then read using an EnVision-Alpha Reader (model #2104 Perkin Elmer; Waltham, Mass.).

Cell viability was assayed by adding 15 μL of Cell Titer Glo ((Catalog #G7571 Promega Madison, Wis.) to each well with cells with media. The plates were incubated foat RT for 15-20 minutes on a plate shaker at low speed. The plates were then read using an EnVision-Alpha Reader (model #2104 Perkin Elmer; Waltham, Mass.).

Data from both assays was analyzed using Assay Assistant (Constellation Pharmaceuticals In-house product) and Activity Base (IDBS Ltd, Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

Table 3 shows the activity of selected compounds of this invention in the two different HeLa cell assays described above. $EC_{50}$ values are reported as follows: "A" indicates an $EC_{50}$ value of less than 400 nM; "B" indicates an $EC_{50}$ value of 400 nM to 2 μM; "C" indicates an $EC_{50}$ value of greater than 2 μM and less than 10 μM for each enzyme; "D" indicates an $EC_{50}$ value of greater than 10 μM for each enzyme; and "*(X μM)" indicates that no inhibition was observed at the highest concentration (i.e., X μM) of compound tested.

TABLE 3

Ec50 Values for Selected Compounds of the Invention In Hela Cells Expressing H3k27 Mutant EZH2.

| Compound No. | H3K27me3 _Alpha_ HeLa (EC50) | H3K27me3 _MSD_ HeLa_ (EC50) |
|---|---|---|
| 204 | | B |
| 211 | | B |
| 212 | | B |
| 218 | | A |
| 219 | | B |
| 224 | A | A |
| 230 | | B |
| 240 | | C |
| 241 | | B |
| 243 | | C |
| 253 | A | |
| 256 | | B |
| 261 | A | A |
| 273 | | A |
| 284 | | B |
| 288 | A | B |
| 294 | A | A |
| 298 | A | A |
| 300 | A | A |
| 304 | A | A |
| 310 | A | A |
| 313 | A | A |
| 314 | A | |
| 315 | | D |
| 316 | | B |
| 317 | | A |
| 321 | | A |
| 327 | | A |
| 335 | A | |
| 336 | A | |
| 337 | A | |
| 341 | A | |
| 342 | A | |
| 343 | B | |

TABLE 3-continued

Ec50 Values for Selected Compounds of the Invention In Hela Cells Expressing H3k27 Mutant EZH2.

| Compound No. | H3K27me3 _Alpha_ HeLa (EC50) | H3K27me3 _MSD_ HeLa_ (EC50) |
|---|---|---|
| 344 | A | |
| 345 | A | |
| 346 | A | |
| 347 | B | |
| 352 | B | |
| 355 | A | |
| 356 | A | |
| 357 | A | |
| 358 | B | |
| 359 | B | |
| 360 | C | |
| 362 | A | |
| 363 | A | |
| 364 | *(3.33 μM) | |
| 365 | A | |
| 366 | B | |
| 367 | A | |
| 368 | A | |
| 369 | A | |
| 370 | *(3.33 μM) | |
| 373 | A | |
| 374 | A | |
| 375 | A | |
| 376 | NaN | |
| 377 | B | |

Example 18

Tumor Growth Inhibition Analysis

The anti-tumor efficacy of Compound 362 and 365 in the subcutaneous Karpas422 human lymphoma xenograft model in female CB-17 SCID mice was as follows.

Animals

Species: *Mus Musculus*
Strain: CB-17 SCID mice
Age: 6-8 weeks
Sex: female
Body weight: 18-22 g
Number of animals: 50 mice plus spare
Animal supplier: Shanghai SLAC Laboratory Animal Co., LTD.

Cell Culture

The Karpas422 tumor cells were maintained in vitro as suspension culture in RPMI1640 medium supplemented with 10% heat inactivated fetal calf serum at 37° C. in an atmosphere of 5% $CO_2$ in air. The tumor cells were routinely subcultured twice weekly. The cells growing in an exponential growth phase were harvested and counted for tumor inoculation.

Tumor Inoculation

Each mouse was inoculated subcutaneously at the right flank with the Karpas422 tumor cells ($5\times10^6$) in 0.2 ml of PBS with Matrigel (1:1) for tumor development. Day 23 after tumor inoculation was as day 0 after the start of treatment when the average tumor size reached approximately 300 mm³. Each group consisted of 10 tumor-bearing mice.

Tumor Measurements

Tumor size was measured three times weekly in two dimensions using a caliper, and the volume was expressed in mm³ using the formula: $V=0.536 a \times b^2$ where a and b are the long and short diameters of the tumor, respectively. The tumor size was then used for calculations of T/C values. The T/C value (in percent) is an indication of antitumor effectiveness; T and C are the mean volumes of the treated and control groups, respectively, on a given day. TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Experimental Endpoint and Sample Collection

1). Plasma, tumor and muscle in EPZ-6438 group were collected on day 16 after the start of treatment at 6 h after dosing. Plasma, tumor and muscle in vehicle, CPI-524369, CPI-524416 and CPI-591780 groups were collected on day 25 after the start of treatment at 1 h after dosing. 2). All the blood was taken from each animal with EDTA-K2 as anticoagulant. Plasma was divided into two parts. The first part was for PK analysis; the second part was frozen for backup. 3). Tumor was divided into three parts. The first part was snap-frozen for PK; the second part was snap-frozen for PD analysis; the third part was frozen for backup. 4). Muscle was divided into two parts. The first part was snap-frozen for PK; the second part was frozen for backup.

Tumor Growth Inhibition Analysis

TABLE 4

Tumor growth inhibition calculation for Compounds 362 and 365 in the karpass422 xenograft model calculated based on tumor volume measurements on day 25 or day 16 after the start of treatment

| Treatment | Tumor Size (mm³)[a] on day 25 | T/C[b] (%) | TGI (%) | Significance[d] |
|---|---|---|---|---|
| Vehicle | 1704 ± 123 | — | — | — |
| Compound 362 (160 mg/kg) | 385 ± 66 | 22.59 | 92.75 | *** |
| Compound 365 (160 mg/kg) | 319 ± 67 | 18.72 | 97.25 | *** |

Note:
[a]Mean ± SEM.
[b]Tumor Growth Inhibition is calculated by dividing the group average tumor volume for the treated group by the group average tumor volume for the control group (T/C). For a test article to be considered to have anti-tumor activity, T/C must be 0.5 or less.
[d]Statistically significant difference (one-way ANOVA), vs vehicle:
***p < 0.001.

The invention claimed is:

1. A compound of the formula:

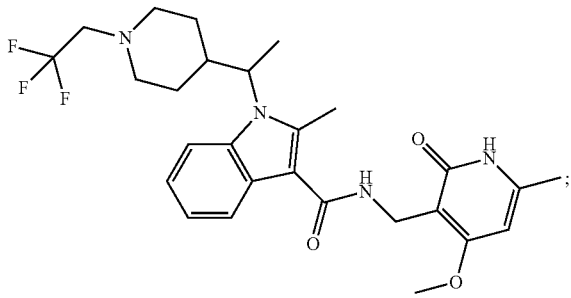 [SMILES: COc1cc(C)[nH]c(=O)c1CNC(=O)c1c(C)n(C(C)C2CCN(CC(F)(F)F)CC2)c2ccccc12]

or a pharmaceutically acceptable salt thereof.

2. The compound of claim 1, wherein the compound is of the formula:

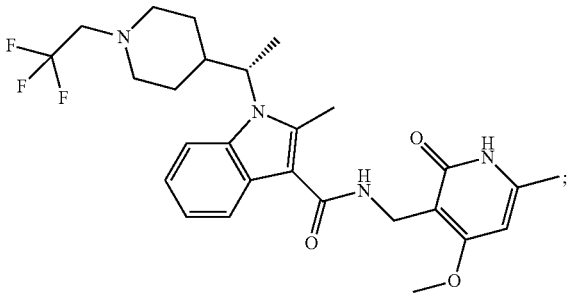

or a pharmaceutically acceptable salt thereof.

3. A pharmaceutical composition comprising a compound of the formula:

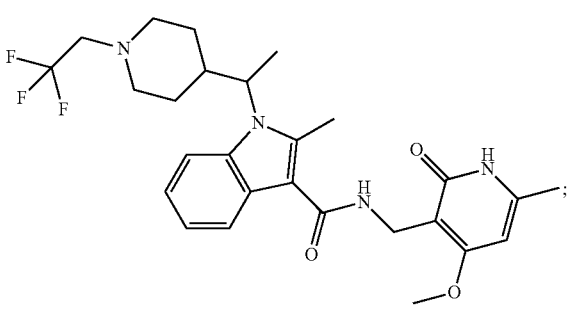

or a pharmaceutically acceptable salt thereof; and a pharmaceutically acceptable carrier.

4. The pharmaceutical composition of claim 3, wherein the compound is of the formula:

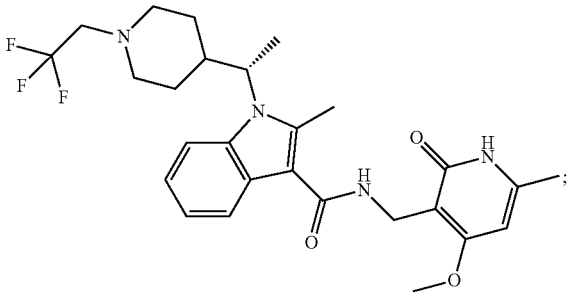 [SMILES: COc1cc(C)[nH]c(=O)c1CNC(=O)c1c(C)n([C@@H](C)C2CCN(CC(F)(F)F)CC2)c2ccccc12]

or a pharmaceutically acceptable salt thereof.

* * * * *